United States Patent
Naito et al.

(10) Patent No.: US 9,296,825 B2
(45) Date of Patent: Mar. 29, 2016

(54) MONOCLONAL ANTIBODY AGAINST EL WHICH INHIBITS ENZYME ACTIVITY OF EL

(71) Applicant: SHIONOGI & CO., LTD., Osaka-shi, Osaka (JP)

(72) Inventors: Shoichi Naito, Sapporo (JP); Junji Onoda, Toyonaka (JP); Tasuku Tsukamoto, Toyonaka (JP); Katsutoshi Yamada, Toyonaka (JP); Shoji Yamane, Toyonaka (JP); Yoshito Numata, Sapporo (JP); Kazuhiko Maekawa, Toyonaka (JP); Tatsuya Takahashi, Toyonaka (JP); Yasuhiko Sato, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/351,373

(22) PCT Filed: Oct. 11, 2012

(86) PCT No.: PCT/JP2012/076284
§ 371 (c)(1),
(2) Date: Apr. 11, 2014

(87) PCT Pub. No.: WO2013/054830
PCT Pub. Date: Apr. 18, 2013

(65) Prior Publication Data
US 2015/0025225 A1 Jan. 22, 2015

(30) Foreign Application Priority Data
Oct. 12, 2011 (JP) ................................ 2011-224846

(51) Int. Cl.
*C07K 16/40* (2006.01)
*A61K 39/395* (2006.01)
*C07K 14/47* (2006.01)

(52) U.S. Cl.
CPC ........... *C07K 16/40* (2013.01); *A61K 39/39533* (2013.01); *C07K 14/47* (2013.01); *C07K 2317/565* (2013.01); *C07K 2317/76* (2013.01)

(58) Field of Classification Search
None
See application file for complete search history.

(56) References Cited

PUBLICATIONS

Kojima et al, 2010. Cardiovascular Research. 87: 385-393.*
Rudikoff et al (Proc Natl Acad Sci USA 1982 vol. 79 pp. 1979-1983).*
MacCallum et al. (Journal of Molecular. Biology, 1996, vol. 262, pp. 732-745).*
Pascalis et al (Journal of Immunology, 2002, vol. 169, pp. 3076-3084).*
Casset et al (Biochemical and Biophysical Research Communications, 2003, vol. 307, pp. 198-205).*
Vajdos et al (Journal of Molecular biology, 2002, vol. 320, pp. 415-428).*
Holm et al (Molecular Immunology, 2007, vol. 44, pp. 1075-1084).*
Chen et al. (Journal of Molecular Biology, 1999, vol. 293, pp. 865-881).*
Wu et al. (Journal of Molecular Biology, 1999, vol. 294, pp. 151-162).*
English translation of International Preliminary Report on Patentability Written Opinion mailed Apr. 24, 2014, in PCT International Application No. PCT/JP2012/076284.
Broedl et al., "Endothelial Lipase: A Modulator of Lipoprotein Metabolism Upregulated by Inflammation", TCM, vol. 14, No. 5, 2004, pp. 202-206.
Griffon et al., "Identification of the Active Form of Endothelial Lipase, a Homodimer in a Head-to-Tail Conformation", The Journal of Biological Chemistry, vol. 284, No. 35, Aug. 28, 2009, pp. 23322-23330 (published online Jun. 30, 2009).
Ishida et al., "Endothelial Lipase Modulates Susceptibility to Atherosclerosis in Apolipoprotein-E-deficient Mice", The Journal of Biological Chemistry, vol. 279, No. 43, Issue of Oct. 22, 2004, pp. 45085-45092 (published online Aug. 9, 2004).
Jaye et al., "A novel endothelial-derived lipase that modulates HDL metabolism", Nature Genetics, vol. 21, Apr. 1999. pp. 424-428.
Jin et al., "Inhibition of endothelial lipase causes increased HDL cholesterol levels in vivo", The Journal of Clinical Investigation, vol. 111, No. 3, Feb. 2003, pp. 357-362 (downloaded on Mar. 2, 2014).

* cited by examiner

*Primary Examiner* — Zachary Howard
(74) *Attorney, Agent, or Firm* — Birch, Stewart, Kolasch & Birch, LLP

(57) ABSTRACT

Provided is a monoclonal antibody or a fragment thereof that selectively inhibits enzyme activity of EL and pharmaceutical compositions containing the same as an active ingredient useful for the treatment of arteriosclerosis or metabolic syndrome.

6 Claims, 17 Drawing Sheets

Figure 5A

```
EL    1 MSNSVPLLCFWSLCYCFAAGSPVPPGPEGRLEDKLHKPKATQLEVKPSVRFNLRTSKDPEHEGCYLSVCHSQELEDGSFN  80
LPL   1 ----------MESKALLVLTLAVWLQSLTASRGGVAAADQRRDFIDIESKFALRTPEDTAEDTCHLIPGVAESVATCHFN  70
HL    1 --MDTSPLCFSILVLCTFIQSSALGQSLKPEPFGRRAQGVELNKTLHEMKTRFLLFGETNQGQIRINHPDTLQEKGSFN  78

EL   81 MTAKTFLIIHGWTMSGIFENWLHKLVSALHTREKDA-NWVVDWLPLAHQLYTDAVNNTRVVGHSIARMLDWLQEKDDFS 159
LPL  71 HSSKTFMMIHGWTVTGMYESWVPKLVAALYKREFDS-NVIVVDWLSRAQEHYPVSAGYTKLVGQDVARFINWMEEEFNYP 149
HL   79 SSSLPLVMIIHGWSVDGVLENWIWQMVAALKSQPAQPVNVGLVDWLTLAHDHYTIAVRNTRLVGKEVAALLRWLEESVQLS 158

EL  160 LGNVHLIGYSLGAHVAGYAGNFVKGI--VGRITGLDPAGPMFEGADIHKRLSPDDADFVDVLHTNTRSF-GLSIGIQMPV 236
LPL 150 LDNVHLLGYSLGAHAAGIAGSLTNKK--MRITGLDPAGPNFEYAEAPSRLSPDDADFVDVLHTFTRGSPSRSIGIQKPV 227
HL  159 RSHVHLIGYSLGAHVSGFAGSSIGGTHKIGRITGLDAAGPLFEGSAPSNRLSPDDAKFVDAIHTFTREHMGLSVGIKQPI 238

EL  237 GHLDIYPNGGDFQPGCGLND---VLGSIAYGTITEVVKGHERAVHLFVDSIMVQDKFSFAFQCTLSNHFKKGLCLSCRK 313
LPL 228 GHVDIYPNGGTFQPGCNIGEAIRVIAERGLDVQLVKCSHERSTHLFIDSLLNEENPSKAYRCSSKEAFEKGLCLSCRK 307
HL  239 GHYEFYPNGGSFQPGCHFLELYRHIAQHGFNAITQTIKCSHERSVALFIDSLLHAGTQSMAYPCGDMNSFSQELCLSCRK 318

EL  314 NRCNSIGYNAKNMRNKRSKMYLKTRAGMPEHVYHYQMKIHVFSYKNMGELEPTFYVTLYGTNALSQTIPLEIVERIEQN 393
LPL 308 NRCNNLGYEINKMLAKRSSKMYLKTRSQMEYKVEHYQVKIHFSGTESETHTNQAFEISLYGTVADSENEPSTIPES-VSTN 386
HL  319 GRCNILGYHVRQEPRSKCKRLFLVTRAQSPFKVYHYQFKIQEIN-QTETPIDTFFTMSLGTKEKMQKCPITIGKGGASM 397

EL  394 AFNTFLVTEEPLQELHKIDIPLWEGASLQSWYLWKEFRSYLSQPRNFGREINIRRIVKSGETQRKLTFCTEDPENTSI 472
LPL 387 KTYSFLIYTEVDIGELLMLKLWK--SDSYFS-WSDWW-------SEHG--FAIQKIRVKAGETQKKVIFCSREKVSHLQ 454
HL  398 KTYSFLITLDVDIGELIMIKFWE--NSAVMAKWDTVQTIIPWSTGERHSGIVLKTLRVKAGETQQRMTFCSENTDDLL 476

EL  473 SPGRELWRKCRDGWRMKNETSPTVELP 500          ┌ - - - - - - - - - - - - - - - - - - - ┐
LPL 455 KGKAPAVEVKCHDKSLNKKSG------- 475         : Binding region of 12B10 antibody :
HL  477 RPTQEKIEVKCELKSKTSKRKIR----- 499         └ - - - - - - - - - - - - - - - - - - - ┘
                                              *:catalytic triad
```

Figure 5B

```
EL    1 MSNSVPLLCFWSLCYCFAAGSPVPPGPEGRLEDKLHKPKATQLEVKPSVRFNLRTSKDPEHEGCYLSVCHSQELEDGSFN  80
LPL   1 ----------MESKALLVLTLAVWLQSLTASRGGVAAADQRRDFIDIESKFALRTPEDTAEDTCHLIPGVAESVATCHFN  70
HL    1 --MDTSPLCFSILVLCIFIQSSALGQSLKPEPFGRRAQGVELNKTLHEMKTRFLLFGETNQGQIRINHPDTLQEKGSFN  78

EL   81 MTAKTFLIIHGWTMSGIFENWLHKLVSALHTREKDA-NWVVDWLPLAHQLYTDAVNNTRVVGHSIARMLDWLQEKDDFS 159
LPL  71 HSSKTFMMIHGWTVTGMYESWVPKLVAALYKREFDS-NVIVVDWLSRAQEHYPVSAGYTKLVGQDVARFINWMEEEFNYP 149
HL   79 SSSLPLVMIIHGWSVDGVLENWIWQMVAALKSQPAQPVNVGLVDWLTLAHDHYTIAVRNTRLVGKEVAALLRWLEESVQLS 158

EL  160 LGNVHLIGYSLGAHVAGYAGNFVKGI--VGRITGLDPAGPMFEGADIHKRLSPDDADFVDVLHTNTRSF-GLSIGIQMPV 236
LPL 150 LDNVHLLGYSLGAHAAGIAGSLTNKK--MRITGLDPAGPNFEYAEAPSRLSPDDADFVDVLHTFTRGSPSRSIGIQKPV 227
HL  159 RSHVHLIGYSLGAHVSGFAGSSIGGTHKIGRITGLDAAGPLFEGSAPSNRLSPDDAKFVDAIHTFTREHMGLSVGIKQPI 238

EL  237 GHLDIYPNGGDFQPGCGLND---VLGSIAYGTITEVVKGHERAVHLFVDSIMVQDKFSFAFQCTLSNHFKKGLCLSCRK 313
LPL 228 GHVDIYPNGGTFQPGCNIGEAIRVIAERGLDVQLVKCSHERSTHLFIDSLLNEENPSKAYRCSSKEAFEKGLCLSCRK 307
HL  239 GHYEFYPNGGSFQPGCHFLELYRHIAQHGFNAITQTIKCSHERSVALFIDSLLHAGTQSMAYPCGDMNSFSQELCLSCKK 318

EL  314 NRCRSIGYNAKNMENKRSKMYLKTRAGMPEHVYHYQMKIHVFSYKNMGELEPTFYVTLYGTNALSQTIPLEIVERIEQN 393
LPL 308 NRCNNLGYEINKMLAKRSSKMYLKTRSQMEYKVEHYQVKIHFSGTESETHTNQAFEISLYGTVADSENLPTIPES-VSTN 386
HL  319 GRCMILGYHVRQEPRSKCKRLFLVTRAQSPFKVYHYQFKIQEIN-QTETPIDTFFTMSLGTKEKMQKCPITIGKGIASM 397

EL  394 AFNTFLVTEEPLQELHKIDIPLWEGASLQSWYLWKEFRSYLSQPRNFGREINIRRIVKSGETQRKLTFCTEDPENTSI 472
LPL 387 KTYSFLIYTEVDIGELLMLKLWK--SDSYFS-WSDWW-------SEHG--FAIQKIRVKAGETQKKVIFCSREKVSHLQ 454
HL  398 KTYSFLITLDVDIGELIMIKFWE--NSAVMAKWDTVQTIIPWSTGERHSGIVLKTLRVKAGETQQRMTFCSENTDDLLL 476

EL  473 SPGRELWRKCRDGWRMKNETSPTVELP 500          ┌ - - - - - - - - - - - - - - - - - - - - - - - - - - - - - - ┐
LPL 455 KGKAPAVEVKCHDKSLNKKSG------- 475         : Binding region of antibodied of the present invention :
HL  477 RPTQEKIEVKCELKSKTSKRKIR----- 499         └ - - - - - - - - - - - - - - - - - - - - - - - - - - - - - - ┘
                                              *:catalytic triad
```

Figure 6A

Heavy chain of 12B10

```
                                        CDR1                            CDR2
QVTLKESGPGILKPSQTLSLTCSFSGFSLSTSGMGVGWIRQPSGKGLEWLAHIWWNDEKYYNPS
LKSQLTISKDTSRNQVFLKITSVDTADTATYYCARSYDGSPFPSWGQGTLVTVSA
                                                   CDR3
```

Light chain of 12B10

```
                              CDR1                       CDR2
DIQMTQSPSSLSASLGGKVTITCKASQDINKYIAWFQHKPGKGPRLLMAYPFTLQPGIPSRF
SGNGSGRDYSFSISNLEPEDIATYYCLQYDNLLWTFGGGTRLEIK
                         CDR3
```

Figure 6B
heavy chain of 47B2

```
                                        CDR1                            CDR2
QVALKESGPGILQPSQTLSLTCSFSGFSLSTSGMGVGWIRQPSGKGLEWLAHIWWHGNKYYSTG
LKSRLTISKDTSNNQVFLKIASVDTADTATYYCARISAGYPLDYWGQGTSVTVSS
                                                   CDR3
```

Light chain of 47B2

```
                              CDR1                       CDR2
DIQMTQSPSSLSASLGGKVTITCKASQDINKYIVWYQHKPGKGPRLLIHYTSTLQPGFPSRFS
GSGSGRDYSLSITNLEPEDIATYYCLQYDNLLWTFGGGTKLEIK
                         CDR3
```

Figure 6C
Heavy chain of 25E4

```
                                        CDR1                            CDR2
QVALKESGPGILQPSQTLSLTCSFSGFSLSTSGMGVGWIRQPSGKGLEWLAHIWWHGNKYYSTA
LKSRLTISKDTSNNQVFLKIASVDTADTATYYCARISDGYPLDYWGQGTSVTVSS
                                                   CDR3
```

Light chain of 25E4

```
                              CDR1                       CDR2
DIQMTQSPSSLSASLGGKVTITCKASQDINKYIVWYQQKPGKGPRLLIHYTSTLQPGFPSRFS
GSGSGRDYSLSITNLEPEDIATYYCLQYDNLLWTFGGGTKLEIK
                         CDR3
```

Figure 6D
Heavy chain of 16A11

```
                                   CDR1                       CDR2
QVTLKESGPGILQPSQTLSLTCSFSGFSLSTSGMGVGWVRQPSGKGLEWLAHIWWNDYYYYKTA
LKSRLTISKDTSNNQVFLKIASVDTVDTATYYCARMAPGTPFPSWGQGTLVTVSA
                                     CDR3
```

Light chain of 16A11

```
                             CDR1                      CDR2
DIQMTQSPSSLSASLGGKVTITCKASQDINRYIAWYQHKPGKGPRLLIHYTSTLQPGIPSRFS
GSGSGRDYSFSISNLEPEDIATYYCLQYDILLWTFGGGTKLEIK
                          CDR3
```

Figure 6E
Heavy chain of 8F5

```
                                   CDR1                       CDR2
QVTLKESGPGILQPSQTLSLTCSFSGFSLSTSNMGVGWIRQPSGKGLEWLAHIWWNDYKYYNTA
LKSRLTISKDTSNNQVFLKIASLDTADTATYYCARIGGGTPLDYWGQGTSLTVSS
                                   CDR3
```

Light chain of 8F5

```
                             CDR1                      CDR2
DIQMAQSPSSLSASLGGKVTITCKASQDIHTYIAWYQHKPGKGPRLLMLYTSTLQPGIPSRFS
GSGSGRDYSFSISNLEPEDIATYYCLQYDDLLWTFGGGTKLEIK
                          CDR3
```

Figure 6F
Heavy chain of 3B1

```
                                    CDR1                    CDR2
QVTLKESGPGILQPSQTLSLTCSFSGFSLSTSGVGVGWIRQPSGKGLEWLAHIWWNDNKYYNTA
LKSRLTISKDTSNNQVFLKIASVDTADTATYFCARSYDGYPFDYWGQGTLVTVSA
                                    CDR3
```

Light chain of 3B1

```
                              CDR1                  CDR2
DIQMTQSPSSLSASLGGKVTITCKASQDINKYIVWYQHKPGKGPRLLIHHTSTLQPGIPSRFS
ESGSGRDYSFSISNLEPEDIASYYCLQYDTLLWTFGGGTKLEIR
                    CDR3
```

Figure 6G
Heavy chain of 41H8

```
                                    CDR1                    CDR2
QVTLKESGPGILQPSQTLSLTCSFSGFSLSTYGMGVGWIRQPSGKGLEWLAHIWWNENKYYNTD
LKSRLTISKDTSNNQVFLKIASVDTADTATYYCARIGPGVPFDYWGQGTTITVSS
                                    CDR3
```

Light chain of 41H8

```
                              CDR1                  CDR2
DIQMTQSPSSLSASLGGKVTITCKASQDINKFIAWYQHKPGKGPRLLIHYTSTLQPGIPSRFN
GSGSGRDYSFTISNLEPEDIATYYCLQYDILTWTFGGGTKLEIK
                    CDR3
```

Figure 10B

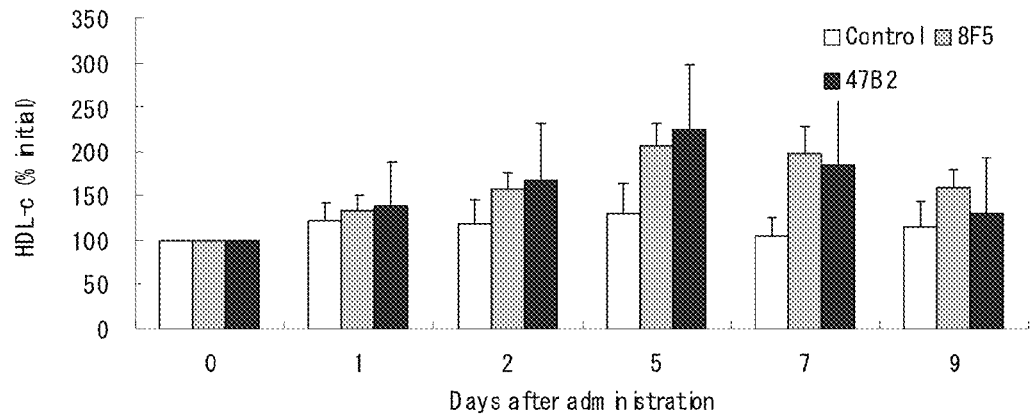

Figure 11A

Alignment of heavy chain

```
                             CDR1
12B10   1   QVTLKESGPGILKPSQTLSLTCSFSGFSLSTSGMGVGWIRQPSGKGLEWL   50
47B 2   1   QVALKESGPGILQPSQTLSLTCSFSGFSLSTSGMGVGWIRQPSGKGLEWL   50
25E 4   1   QVALKESGPGILQPSQTLSLTCSFSGFSLSTSGMGVGWIRQPSGKGLEWL   50
16A11   1   QVTLKESGPGILQPSQTLSLTCSFSGFSLSTSGMGVGWVRQPSGKGLEWL   50
8 F 5   1   QVTLKESGPGILQPSQTLSLTCSFSGFSLSTSNMGVGWIRQPSGKGLEWL   50
3 B 1   1   QVTLKESGPGILQPSQTLSLTCSFSGFSLSTSGVGVGWIRQPSGKGLEWL   50
41H 8   1   QVTLKESGPGILQPSQTLSLTCSFSGFSLSTYGMGVGWIRQPSGKGLEWL   50

CDR2
12B10   51  AHIWWNDEKYYNPSLKSQLTISKDTSRNQVFLKITSVDTADTATYYCARS  100
47B 2   51  AHIWWHGNKYYSTGLKSRLTISKDTSNNQVFLKIASVDTADTATYYCARI  100
25E 4   51  AHIWWHGNKYYSTALKSRLTISKDTSNNQVFLKIASVDTADTATYYCARI  100
16A11   51  AHIWWNDYYYKTALKSRLTISKDTSNNQVFLKIASVDTVDTATYYCARM  100
8 F 5   51  AHIWWNDYKYYNTALKSRLTISKDTSNNQVFLKIASLDTADTATYYCARI  100
3 B 1   51  AHIWWNDNKYYNTALKSRLTISKDTSNNQVFLKIASVDTADTATYFCARS  100
41H 8   51  AHIWWNENKYYNTDLKSRLTISKDTSNNQVFLKIASVDTADTATYYCARI  100

CDR3
12B10   101 YDGSPFPSWGQGTLVTVSA                                 119
47B 2   101 SAGYPLDYWGQGTSVTVSS                                 119
25E 4   101 SDGYPLDYWGQGTSVTVSS                                 119
16A11   101 APGTPFPSWGQGTLVTVSA                                 119
8 F 5   101 GGGTPLDYWGQGTSLTVSS                                 119
3 B 1   101 YDGYPFDYWGQGTLVTVSA                                 119
41H 8   101 GPGVPFDYWGQGTTITVSS                                 119
```

Figure 11B

Alignment of light chain

```
                                    CDR1
12B10   1  DIQMTQSPSSLSASLGGKVTITCKASQDINKYIAWFQHKPGKGPRLLMAY  50
47B 2   1  DIQMTQSPSSLSASLGGKVTITCKASQDINKYIVWYQHKPGKGPRLLIHY  50
25E 4   1  DIQMTQSPSSLSASLGGKVTITCKASQDINKYIVWYQQKPGKGPRLLIHY  50
16A11   1  DIQMTQSPSSLSASLGGKVTITCKASQDINRYIAWYQHKPGKGPRLLIHY  50
8 F 5   1  DIQMAQSPSSLSASLGGKVTITCKASQDIHTYIAWYQHKPGKGPRLLMLY  50
3 B 1   1  DIQMTQSPSSLSASLGGKVTITCKASQDINKYIVWYQHKPGKGPRLLIHH  50
41H 8   1  DIQMTQSPSSLSASLGGKVTITCKASQDINKFIAWYQHKPGKGPRLLIHY  50

CDR2                               CDR3
12B10  51  PFTLQPGIPSRFSGNGSGRDYSFSISNLEPEDIATYYCLQYDNLLWTFGG  100
47B 2  51  TSTLQPGFPSRFSGSGSGRDYSLSITNLEPEDIATYYCLQYDNLLWTFGG  100
25E 4  51  TSTLQPGFPSRFSGSGSGRDYSLSITNLEPEDIATYYCLQYDNLLWTFGG  00
16A11  51  TSTLQPGIPSRFSGSGSGRDYSFSISNLEPEDIATYYCLQYDILLWTFGG  100
8 F 5  51  TSTLQPGIPSRFSGSGSGRDYSFSISNLEPEDIATYYCLQYDDLLWTFGG  100
3 B 1  51  TSTLQPGIPSRFSESGSGRDYSFSISNLEPEDIASYYCLQYDTLLWTFGG  100
41H 8  51  TSTLQPGIPSRFNGSGSGRDYSFTISNLEPEDIATYYCLQYDILTWTFGG  100

12B10  101 GTRLEIK                                                 107
47B 2  101 GTKLEIK                                                 107
25E 4  101 GTKLEIK                                                 107
16A11  101 GTKLEIK                                                 107
8 F 5  101 GTKLEIK                                                 107
3 B 1  101 GTKLEIR                                                 107
41H 8  101 GTKLEIK                                                 107
```

MONOCLONAL ANTIBODY AGAINST EL WHICH INHIBITS ENZYME ACTIVITY OF EL

TECHNICAL FIELD

The present invention relates to a monoclonal antibody that inhibits enzyme activity of Endothelial Lipase (hereinafter, referred to EL) and pharmaceutical compositions containing the same. More specifically, the present invention relates to an antibody that selectively inhibits enzyme activity of EL, or a part thereof, and a pharmaceutical composition containing the same.

BACKGROUND ART

EL is a phospholipase that belongs to triglyceride lipase (hereinafter, referred to TG) family (non-patent literature: 1). Human EL is comprised of 500 amino acids (NCBI Accession number NP_006024.1, SEQ ID NO: 1) and rabbit EL is comprised of 500 amino acids (NCBI Accession number NO_001182567, SEQ ID NO: 2). TG family contains lipoprotein lipase (hereinafter, referred to LPL) and hepatic lipase (hereinafter, referred to HL).

The analysis of EL knockout mouse and EL transgenic mouse revealed that EL relates HDL cholesterol (hereinafter, referred to HDL-c) metabolism by its strong phospholipase activity, and have been a focus as a factor which controls HDL-c level in blood (non-patent literature: 2). It has been well-known that there is a negative correlation between coronary artery disease (hereinafter, referred to CAD) and HDL-c level in blood. HDL shows anti-artherogenic effect by its antioxidant effect, anti-inflammatory effect and reverse cholesterol transport and so on, low HDL-c emia is recognized one of the risk factor of CAD. Therefore, EL inhibitor could become a treatment for CAD by increasing HDL-c in blood. In fact, it was reported that lesion mouse of EL knockout showed increase in HDL-c and decrease in atherosclerotic lesions (non-patent literature: 3).

These knowledge indicates that the selective EL inhibitors have a potential of therapeutic agents for abnormality of lipid metabolism and arteriosclerosis.

The selective inhibition of EL is so useful for the treatment of abnormality of lipid metabolism and arteriosclerosis that the production of EL antibodies which inhibit EL activity is one of the important approaches. So far, it has been reported that rabbit polyclonal antibody which inhibits EL activity was prepared, HDL-c level in mouse blood increased after administration of the antibody (non-patent literature: 4).

Polyclonal antibody recognizes various region of EL and the selectivity to EL is expected to be low. Also, it is impossible to use rabbit anti-EL polyclonal antibody which is high immunogenicity to human as therapeutic agent for chronic diseases because the therapeutic agents for chronic diseases such as the abnormality of lipid metabolism and arteriosclerosis which related to EL have to be administrated for a long term. Moreover, it is difficult to manipulate immunogenicity of polyclonal antibody.

Because of these situations, monoclonal antibodies which inhibit selectively EL activity are required.

Non-patent document 1: Nature Genetics., 1999, vol. 21, p. 424
Non-patent document 2: TCM., 2004, vol. 14(5), p. 202-206
Non-patent document 3: The Journal of Biological Chemistry., 2004, vol. 279, No. 43, 22 p. 45085-45092
Non-patent document 4: J clin Invest., 2003, Vol. 111(3), p. 357

SUMMARY OF THE INVENTION

Problem to be Solved by the Invention

It is an object of the present invention to provide an antibody that selectively inhibits enzyme activity of EL, or a part thereof, and a pharmaceutical composition containing the same.

Means for Solving the Problem

As a result of diligent efforts, the present inventors have succeeded in finding a monoclonal antibody that selectively inhibits enzyme activity of EL.

To be more specific, the present invention relates to:
(1) A monoclonal antibody or a fragment thereof that binds to positions of 331 to 459 region in amino acid sequence of SEQ ID NO: 1.
(2) A monoclonal antibody or a fragment thereof according to (1) that binds to positions of 411 to 459 region in amino acid sequence of SEQ ID NO: 1.
(3) A monoclonal antibody or a fragment thereof according to (1) or (2) that inhibits enzyme activity of EL.
(4) A monoclonal antibody or a fragment thereof, selected from the group of
1) A monoclonal antibody or a fragment thereof, having a heavy chain variable region including three CDRs comprising amino acid sequence of SEQ ID NO: 7, amino acid sequence of SEQ ID NO: 8 and amino acid sequence of SEQ ID NO: 9 and
a light chain variable region including three CDRs comprising amino acid sequence of SEQ ID NO: 11, amino acid sequence of SEQ ID NO: 12 and amino acid sequence of SEQ ID NO: 13.
2) A monoclonal antibody or a fragment thereof, having a heavy chain variable region including three CDRs comprising amino acid sequence of SEQ ID NO: 7, amino acid sequence of SEQ ID NO: 8 and amino acid sequence of SEQ ID NO: 9 and
a light chain variable region including three CDRs, said three CDRs consisting of amino acids that are one or more amino acids are depleted, substituted or added in at least one of the three CDRs, said the three CDRs comprising amino acid sequence of SEQ ID NO: 11, amino acid sequence of SEQ ID NO: 12 and amino acid sequence of SEQ ID NO: 13, and inhibiting EL enzyme activity.
3) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 7, amino acid sequence of SEQ ID NO: 8 and amino acid sequence of SEQ ID NO: 9, and
a light chain variable region including three CDRs comprising amino acid sequence of SEQ ID NO: 11, amino acid sequence of SEQ ID NO: 12 and amino acid sequence of SEQ ID NO: 13,
and inhibiting EL enzyme activity.
4) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 7, amino acid sequence of SEQ ID NO: 8 and amino acid sequence of SEQ ID NO: 9, and a light chain variable region including three CDRs, said three CDRs consisting of amino acids that are one or more amino acids are depleted, substituted or added in at least one of the three CDRs, said three CDRs comprising amino acid sequence of SEQ ID NO: 11, amino acid sequence of SEQ ID NO: 12 and amino acid sequence of SEQ ID NO: 13, and inhibiting EL enzyme activity.

5) A monoclonal antibody or a fragment thereof, having a heavy chain variable region including three CDRs comprising amino acid sequence of SEQ ID NO: 19, amino acid sequence of SEQ ID NO: 20 and amino acid sequence of SEQ ID NO: 21 and a light chain variable region including three CDRs comprising amino acid sequence of SEQ ID NO: 23, amino acid sequence of SEQ ID NO: 24 and amino acid sequence of SEQ ID NO: 25.

6) A monoclonal antibody or a fragment thereof, having a heavy chain variable region including three CDRs comprising amino acid sequence of SEQ ID NO: 19, amino acid sequence of SEQ ID NO: 20 and amino acid sequence of SEQ ID NO: 21 and a light chain variable region including three CDRs, said three CDRs consisting of amino acids that are one or more amino acids are depleted, substituted or added in at least one of the three CDRs, said the three CDRs comprising amino acid sequence of SEQ ID NO: 23, amino acid sequence of SEQ ID NO: 24 and amino acid sequence of SEQ ID NO: 25, and inhibiting EL enzyme activity.

7) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 19, amino acid sequence of SEQ ID NO: 20 and amino acid sequence of SEQ ID NO: 21, and a light chain variable region including three CDRs comprising amino acid sequence of SEQ ID NO: 23, amino acid sequence of SEQ ID NO: 24 and amino acid sequence of SEQ ID NO: 25, and inhibiting EL enzyme activity.

8) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 19, amino acid sequence of SEQ ID NO: 20 and amino acid sequence of SEQ ID NO: 21, and a light chain variable region including three CDRs, said three CDRs consisting of amino acids that are one or more amino acids are depleted, substituted or added in at least one of the three CDRs, said the three CDRs comprising amino acid sequence of SEQ ID NO: 23, amino acid sequence of SEQ ID NO: 24 and amino acid sequence of SEQ ID NO: 25, and inhibiting EL enzyme activity.

9) A monoclonal antibody or a fragment thereof, having a heavy chain variable region including three CDRs comprising amino acid sequence of SEQ ID NO: 27, amino acid sequence of SEQ ID NO: 28 and amino acid sequence of SEQ ID NO: 29 and a light chain variable region including three CDRs comprising amino acid sequence of SEQ ID NO: 31, amino acid sequence of SEQ ID NO: 32 and amino acid sequence of SEQ ID NO: 33.

10) A monoclonal antibody or a fragment thereof, having a heavy chain variable region including three CDRs comprising amino acid sequence of SEQ ID NO: 27, amino acid sequence of SEQ ID NO: 28 and amino acid sequence of SEQ ID NO: 29 and a light chain variable region including three CDRs, said three CDRs consisting of amino acids that are one or more amino acids are depleted, substituted or added in at least one of the three CDRs, said the three CDRs comprising amino acid sequence of SEQ ID NO: 31, amino acid sequence of SEQ ID NO: 32 and amino acid sequence of SEQ ID NO: 33, and inhibiting EL enzyme activity.

11) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 27, amino acid sequence of SEQ ID NO: 28 and amino acid sequence of SEQ ID NO: 29, and a light chain variable region including three CDRs comprising amino acid sequence of SEQ ID NO: 31, amino acid sequence of SEQ ID NO: 32 and amino acid sequence of SEQ ID NO: 33, and inhibiting EL enzyme activity.

12) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 27, amino acid sequence of SEQ ID NO: 28 and amino acid sequence of SEQ ID NO: 29, and a light chain variable region including three CDRs, said three CDRs consisting of amino acids that are one or more amino acids are depleted, substituted or added in at least one of the three CDRs, said the three CDRs comprising amino acid sequence of SEQ ID NO: 31, amino acid sequence of SEQ ID NO: 32 and amino acid sequence of SEQ ID NO: 33, and inhibiting EL enzyme activity.

13) A monoclonal antibody or a fragment thereof, having a heavy chain variable region including three CDRs comprising amino acid sequence of SEQ ID NO: 35, amino acid sequence of SEQ ID NO: 36 and amino acid sequence of SEQ ID NO: 37 and a light chain variable region including three CDRs comprising amino acid sequence of SEQ ID NO: 39, amino acid sequence of SEQ ID NO: 40 and amino acid sequence of SEQ ID NO: 41.

14) A monoclonal antibody or a fragment thereof, having a heavy chain variable region including three CDRs comprising amino acid sequence of SEQ ID NO: 35, amino acid sequence of SEQ ID NO: 36 and amino acid sequence of SEQ ID NO: 37 and a light chain variable region including three CDRs, said three CDRs consisting of amino acids that are one or more amino acids are depleted, substituted or added in at least one of the three CDRs, said the three CDRs comprising amino acid sequence of SEQ ID NO: 39, amino acid sequence of SEQ ID NO: 40 and amino acid sequence of SEQ ID NO: 41, and inhibiting EL enzyme activity.

15) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 35, amino acid sequence of SEQ ID NO: 36 and amino acid sequence of SEQ ID NO: 37, and a light chain variable region including three CDRs comprising amino acid sequence of SEQ ID NO: 39, amino acid sequence of SEQ ID NO: 40 and amino acid sequence of SEQ ID NO: 41, and inhibiting EL enzyme activity.

16) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 35, amino acid sequence of SEQ ID NO: 36 and amino acid sequence of SEQ ID NO: 37, and a light chain variable region including three CDRs, said three CDRs consisting of amino acids that are one or more amino acids are depleted, substituted or added in at least one of the three CDRs, said the three CDRs comprising amino acid sequence of SEQ ID NO: 39, amino acid sequence of SEQ ID NO: 40 and amino acid sequence of SEQ ID NO: 41, and inhibiting EL enzyme activity.

17) A monoclonal antibody or a fragment thereof, having a heavy chain variable region including three CDRs comprising amino acid sequence of SEQ ID NO: 43, amino acid sequence of SEQ ID NO: 44 and amino acid sequence of SEQ ID NO: 45 and a light chain variable region including three CDRs comprising amino acid sequence of SEQ ID NO: 47, amino acid sequence of SEQ ID NO: 48 and amino acid sequence of SEQ ID NO: 49.

18) A monoclonal antibody or a fragment thereof, having a heavy chain variable region including three CDRs comprising amino acid sequence of SEQ ID NO: 43, amino acid sequence of SEQ ID NO: 44 and amino acid sequence of SEQ ID NO: 45 and a light chain variable region including three CDRs, said three CDRs consisting of amino acids that are one or more amino acids are depleted, substituted or added in at least one of the three CDRs, said the three CDRs comprising amino acid sequence of SEQ ID NO: 47, amino acid sequence of SEQ ID NO: 48 and amino acid sequence of SEQ ID NO: 49, and inhibiting EL enzyme activity.

19) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 43, amino acid sequence of SEQ ID NO: 44 and amino acid sequence of SEQ ID NO: 45, and a light chain variable region including three CDRs comprising amino acid sequence of SEQ ID NO: 47, amino acid sequence of SEQ ID NO: 48 and amino acid sequence of SEQ ID NO: 49, and inhibiting EL enzyme activity.

20) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 43, amino acid sequence of SEQ ID NO: 44 and amino acid sequence of SEQ ID NO: 45, and a light chain variable region including three CDRs, said three CDRs consisting of amino acids that are one or more amino acids are depleted, substituted or added in at least one of the three CDRs, said the three CDRs comprising amino acid sequence of SEQ ID NO: 47, amino acid sequence of SEQ ID NO: 48 and amino acid sequence of SEQ ID NO: 49, and inhibiting EL enzyme activity.

21) A monoclonal antibody or a fragment thereof, having a heavy chain variable region including three CDRs comprising amino acid sequence of SEQ ID NO: 51, amino acid sequence of SEQ ID NO: 52 and amino acid sequence of SEQ ID NO: 53 and a light chain variable region including three CDRs comprising amino acid sequence of SEQ ID NO: 55, amino acid sequence of SEQ ID NO: 56 and amino acid sequence of SEQ ID NO: 57.

22) A monoclonal antibody or a fragment thereof, having a heavy chain variable region including three CDRs comprising amino acid sequence of SEQ ID NO: 51, amino acid sequence of SEQ ID NO: 52 and amino acid sequence of SEQ ID NO: 53 and a light chain variable region including three CDRs, said three CDRs consisting of amino acids that are one or more amino acids are depleted, substituted or added in at least one of the three CDRs, said the three CDRs comprising amino acid sequence of SEQ ID NO: 55, amino acid sequence of SEQ ID NO: 56 and amino acid sequence of SEQ ID NO: 57, and inhibiting EL enzyme activity.

23) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 51, amino acid sequence of SEQ ID NO: 52 and amino acid sequence of SEQ ID NO: 53, and a light chain variable region including three CDRs comprising amino acid sequence of SEQ ID NO: 55, amino acid sequence of SEQ ID NO: 56 and amino acid sequence of SEQ ID NO: 57, and inhibiting EL enzyme activity.

24) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 51, amino acid sequence of SEQ ID NO: 52 and amino acid sequence of SEQ ID NO: 53, and a light chain variable region including three CDRs, said three CDRs consisting of amino acids that are one or more amino acids are depleted, substituted or added in at least one of the three CDRs, said the three CDRs comprising amino acid sequence of SEQ ID NO: 55, amino acid sequence of SEQ ID NO: 56 and amino acid sequence of SEQ ID NO: 57, and inhibiting EL enzyme activity.

25) A monoclonal antibody or a fragment thereof, having a heavy chain variable region including three CDRs comprising amino acid sequence of SEQ ID NO: 51, amino acid sequence of SEQ ID NO: 52 and amino acid sequence of SEQ ID NO: 53 and a light chain variable region including three CDRs comprising amino acid sequence of SEQ ID NO: 55, amino acid sequence of SEQ ID NO: 56 and amino acid sequence of SEQ ID NO: 57.

26) A monoclonal antibody or a fragment thereof, having a heavy chain variable region including three CDRs comprising amino acid sequence of SEQ ID NO: 51, amino acid sequence of SEQ ID NO: 52 and amino acid sequence of SEQ ID NO: 53 and a light chain variable region including three CDRs, said three CDRs consisting of amino acids that are one or more amino acids are depleted, substituted or added in at least one of the three CDRs, said the three CDRs comprising amino acid sequence of SEQ ID NO: 55, amino acid sequence of SEQ ID NO: 56 and amino acid sequence of SEQ ID NO: 57,
and inhibiting EL enzyme activity.

27) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 51, amino acid sequence of SEQ ID NO: 52 and amino acid sequence of SEQ ID NO: 53, and
a light chain variable region including three CDRs comprising amino acid sequence of SEQ ID NO: 55, amino acid sequence of SEQ ID NO: 56 and amino acid sequence of SEQ ID NO: 57,
and inhibiting EL enzyme activity.

28) A monoclonal antibody or a fragment thereof, having a heavy chain variable region including three CDRs, said three CDRs consisting of amino acids that are one or more amino acids are depleted, substituted or added in at least one of the three CDRs, said the three CDRs comprising amino acid sequence of SEQ ID NO: 51, amino acid sequence of SEQ ID NO: 52 and amino acid sequence of SEQ ID NO: 53, and
a light chain variable region including three CDRs, said three CDRs consisting of amino acids that are one or more amino acids are depleted, substituted or added in at least one of the three CDRs, said the three CDRs comprising amino acid sequence of SEQ ID NO: 55, amino acid sequence of SEQ ID NO: 56 and amino acid sequence of SEQ ID NO: 57,
and inhibiting EL enzyme activity.

(5) A monoclonal antibody or a fragment thereof, selected from the group of

1) A monoclonal antibody or a fragment thereof, having a heavy chain variable region comprising amino acid sequence of SEQ ID NO: 6, and
a light chain variable region comprising amino acid sequence of SEQ ID NO: 10.

2) A monoclonal antibody or a fragment thereof, having a heavy chain variable region comprising amino acid sequence of SEQ ID NO: 6, and
a light chain variable region comprising amino acids, said amino acids that are one or more amino acids are depleted, substituted or added in amino acids sequence of SEQ ID NO: 10,
and inhibiting EL enzyme activity.

3) A monoclonal antibody or a fragment thereof, having a heavy chain variable region comprising amino acids, said amino acids that are one or more amino acids are depleted, substituted or added in amino acids sequence of SEQ ID NO: 6, and
a light chain variable region comprising amino acid sequence of SEQ ID NO: 10
and inhibiting EL enzyme activity.

4) A monoclonal antibody or a fragment thereof, having a heavy chain variable region comprising amino acids, said amino acids that are one or more amino acids are depleted, substituted or added in amino acids sequence of SEQ ID NO: 6, and
a light chain variable region comprising amino acids, said amino acids that are one or more amino acids are depleted, substituted or added in amino acids sequence of SEQ ID NO: 10,
and inhibiting EL enzyme activity.

5) A monoclonal antibody or a fragment thereof, having a heavy chain variable region comprising amino acid sequence of SEQ ID NO: 18, and
a light chain variable region comprising amino acid sequence of SEQ ID NO: 22.

6) A monoclonal antibody or a fragment thereof, having a heavy chain variable region comprising amino acid sequence of SEQ ID NO: 18, and
a light chain variable region comprising amino acids, said amino acids that are one or more amino acids are depleted, substituted or added in amino acids sequence of SEQ ID NO: 22,
and inhibiting EL enzyme activity.

7) A monoclonal antibody or a fragment thereof, having a heavy chain variable region comprising amino acids, said amino acids that are one or more amino acids are depleted, substituted or added in amino acids sequence of SEQ ID NO: 18, and
a light chain variable region comprising amino acid sequence of SEQ ID NO: 22
and inhibiting EL enzyme activity.

8) A monoclonal antibody or a fragment thereof, having a heavy chain variable region comprising amino acids, said amino acids that are one or more amino acids are depleted, substituted or added in amino acids sequence of SEQ ID NO: 18, and
a light chain variable region comprising amino acids, said amino acids that are one or more amino acids are depleted, substituted or added in amino acids sequence of SEQ ID NO: 22,
and inhibiting EL enzyme activity.

9) A monoclonal antibody or a fragment thereof, having a heavy chain variable region comprising amino acid sequence of SEQ ID NO: 26, and
a light chain variable region comprising amino acid sequence of SEQ ID NO: 30.

10) A monoclonal antibody or a fragment thereof, having a heavy chain variable region comprising amino acid sequence of SEQ ID NO: 26, and
a light chain variable region comprising amino acids, said amino acids that are one or more amino acids are depleted, substituted or added in amino acids sequence of SEQ ID NO: 30,
and inhibiting EL enzyme activity.

11) A monoclonal antibody or a fragment thereof, having a heavy chain variable region comprising amino acids, said amino acids that are one or more amino acids are depleted, substituted or added in amino acids sequence of SEQ ID NO: 26, and
a light chain variable region comprising amino acid sequence of SEQ ID NO: 30
and inhibiting EL enzyme activity.

12) A monoclonal antibody or a fragment thereof, having a heavy chain variable region comprising amino acids, said amino acids that are one or more amino acids are depleted, substituted or added in amino acids sequence of SEQ ID NO: 26, and
a light chain variable region comprising amino acids, said amino acids that are one or more amino acids are depleted, substituted or added in amino acids sequence of SEQ ID NO: 30,
and inhibiting EL enzyme activity.

13) A monoclonal antibody or a fragment thereof, having a heavy chain variable region comprising amino acid sequence of SEQ ID NO: 34, and
a light chain variable region comprising amino acid sequence of SEQ ID NO: 38.

14) A monoclonal antibody or a fragment thereof, having a heavy chain variable region comprising amino acid sequence of SEQ ID NO: 34, and a light chain variable region comprising amino acids, said amino acids that are one or more amino acids are depleted, substituted or added in amino acids sequence of SEQ ID NO: 38,
and inhibiting EL enzyme activity.

15) A monoclonal antibody or a fragment thereof, having a heavy chain variable region comprising amino acids, said amino acids that are one or more amino acids are depleted, substituted or added in amino acids sequence of SEQ ID NO: 34, and
a light chain variable region comprising amino acid sequence of SEQ ID NO: 38
and inhibiting EL enzyme activity.

16) A monoclonal antibody or a fragment thereof, having a heavy chain variable region comprising amino acids, said amino acids that are one or more amino acids are depleted, substituted or added in amino acids sequence of SEQ ID NO: 34, and
a light chain variable region comprising amino acids, said amino acids that are one or more amino acids are depleted, substituted or added in amino acids sequence of SEQ ID NO: 38,
and inhibiting EL enzyme activity.

17) A monoclonal antibody or a fragment thereof, having a heavy chain variable region comprising amino acid sequence of SEQ ID NO: 42, and
a light chain variable region comprising amino acid sequence of SEQ ID NO: 46.

18) A monoclonal antibody or a fragment thereof, having a heavy chain variable region comprising amino acid sequence of SEQ ID NO: 42, and
a light chain variable region comprising amino acids, said amino acids that are one or more amino acids are depleted, substituted or added in amino acids sequence of SEQ ID NO: 46,
and inhibiting EL enzyme activity.

19) A monoclonal antibody or a fragment thereof, having a heavy chain variable region comprising amino acids, said amino acids that are one or more amino acids are depleted, substituted or added in amino acids sequence of SEQ ID NO: 42, and
a light chain variable region comprising amino acid sequence of SEQ ID NO: 46
and inhibiting EL enzyme activity.

20) A monoclonal antibody or a fragment thereof, having a heavy chain variable region comprising amino acids, said amino acids that are one or more amino acids are depleted, substituted or added in amino acids sequence of SEQ ID NO: 42, and
a light chain variable region comprising amino acids, said amino acids that are one or more amino acids are depleted, substituted or added in amino acids sequence of SEQ ID NO: 46,
and inhibiting EL enzyme activity.

21) A monoclonal antibody or a fragment thereof, having a heavy chain variable region comprising amino acid sequence of SEQ ID NO: 50, and
a light chain variable region comprising amino acid sequence of SEQ ID NO: 54.

22) A monoclonal antibody or a fragment thereof, having a heavy chain variable region comprising amino acid sequence of SEQ ID NO: 50, and
a light chain variable region comprising amino acids, said amino acids that are one or more amino acids are depleted, substituted or added in amino acids sequence of SEQ ID NO: 54,
and inhibiting EL enzyme activity.

23) A monoclonal antibody or a fragment thereof, having a heavy chain variable region comprising amino acids, said amino acids that are one or more amino acids are depleted, substituted or added in amino acids sequence of SEQ ID NO: 50, and
a light chain variable region comprising amino acid sequence of SEQ ID NO: 54
and inhibiting EL enzyme activity.

24) A monoclonal antibody or a fragment thereof, having a heavy chain variable region comprising amino acids, said amino acids that are one or more amino acids are depleted, substituted or added in amino acids sequence of SEQ ID NO: 50, and
a light chain variable region comprising amino acids, said amino acids that are one or more amino acids are depleted, substituted or added in amino acids sequence of SEQ ID NO: 54,
and inhibiting EL enzyme activity.

25) A monoclonal antibody or a fragment thereof, having a heavy chain variable region comprising amino acid sequence of SEQ ID NO: 58, and
a light chain variable region comprising amino acid sequence of SEQ ID NO: 62.

26) A monoclonal antibody or a fragment thereof, having a heavy chain variable region comprising amino acid sequence of SEQ ID NO: 58, and
a light chain variable region comprising amino acids, said amino acids that are one or more amino acids are depleted, substituted or added in amino acids sequence of SEQ ID NO: 62,
and inhibiting EL enzyme activity.

27) A monoclonal antibody or a fragment thereof, having a heavy chain variable region comprising amino acids, said amino acids that are one or more amino acids are depleted, substituted or added in amino acids sequence of SEQ ID NO: 58, and
a light chain variable region comprising amino acid sequence of SEQ ID NO: 62
and inhibiting EL enzyme activity.

28) A monoclonal antibody or a fragment thereof, having a heavy chain variable region comprising amino acids, said amino acids that are one or more amino acids are depleted, substituted or added in amino acids sequence of SEQ ID NO: 58, and
a light chain variable region comprising amino acids, said amino acids that are one or more amino acids are depleted, substituted or added in amino acids sequence of SEQ ID NO: 62,
and inhibiting EL enzyme activity.

(6) A pharmaceutical composition for treatment or prevention diseases related to EL comprising the antibody or a part thereof according to any one of (3) to (5), as an active ingredient.

(7) A pharmaceutical composition according to (6), wherein diseases related to EL is the arteriosclerosis.

(8) A monoclonal antibody or a fragment thereof according to any one of (3) to (5) for treatment or prevention diseases related to EL.

(9) A monoclonal antibody or a fragment thereof according to (8), wherein diseases related to EL is the arteriosclerosis.

(10) A treatment or prevention method of diseases related to EL that is characterized of administering to a monoclonal antibody or a fragment thereof according to any one of (3) to (5).

(11) A treatment or prevention method according to (10), wherein diseases related to EL is the arteriosclerosis.

(12) A screening method of a monoclonal antibody or a fragment thereof or a hybridoma producing the monoclonal antibody or the fragment thereof that is characterized of using an amino acid comprising at the position 331 to 459 in amino acid sequence of SEQ ID NO: 1 or one or more amino acids are depleted, substituted or added in the amino acid.

(13) A screening method of a monoclonal antibody or a fragment thereof or a hybridoma producing the monoclonal antibody or the fragment thereof that is characterized of using an amino acid comprising at the position 411 to 459 in amino acid sequence of SEQ ID NO: 1 or one or more amino acids are depleted, substituted or added in the amino acid.

(14) A production method of a monoclonal antibody or a fragment thereof that inhibits enzyme activity of EL comprising screening method according to (12) or (13).

(15) A monoclonal antibody or a fragment thereof that are produced by production method according to (12) or (13).

Effect of the Invention

Pharmaceutical compositions containing a monoclonal antibody of the invention are very useful as a drug, especially a drug for prevention and/or treatment of dyslipidemia, hyperlipidemia, arteriosclerosis, atherosclerosis, hypercholesterolemia, hypertriglyceridemia, diabetes, obesity and/or syndrome X because a monoclonal antibody of the invention has the activity for selectively inhibiting enzyme activity of EL.

BRIEF EXPLANATION OF DRAWINGS

FIG. 5A shows an alignment of the amino acid sequences of human EL (SEQ ID NO: 1), human LPL (SEQ ID NO: 66) and human HL (SEQ ID NO: 67). We enclose amino acids which common among two kinds in a solid frame. An amino acid of ★ sign shows catalytic triad, and we enclose amino acid sequences of the 12B10 antibody binding region in a dashed line.

FIG. 5B shows an alignment of the amino acid sequences of human EL (SEQ ID NO: 1), human LPL (SEQ ID NO: 66), and human HL (SEQ ID NO: 67). We enclose amino acids which common over two kinds in a solid frame. An amino acid of ★ sign shows catalytic triad, and we enclose amino acid sequences of an antibody of the invention binding region in a dashed line.

FIG. 6A shows amino acid sequence (SEQ ID NOS: 68 and 69) of a variable region of 1210 antibody, i.e., the heavy chain of 12B10 (SEQ ID NO: 6) and the light chain of 12B10 (SEQ ID NO: 10).

FIG. 6B shows amino acid sequence (SEQ ID NOS: 70 and 71) of a variable region of 47B2 antibody, i.e., the heavy chain of 47B2 (SEQ ID NO: 18) and the light chain of 47B2 (SEQ ID NO: 22).

FIG. 6C shows amino acid sequence (SEQ ID NOS: 72 and 73) of variable region of 25E4 antibody, i.e., the heavy chain of 25E4 (SEQ ID NO: 26) and the light chain of 25E4 (SEQ ID NO: 30).

FIG. 6D shows amino acid sequence (SEQ ID NOS: 74 and 75) of a variable region of 16A11 antibody, i.e., the heavy chain of 16A11 (SEQ ID NO: 34) and the light chain of 16A11 (SEQ ID NO: 38).

FIG. 6E shows amino acid sequence (SEQ ID NOS: 76 and 77) of a variable region of 8F5 antibody, i.e., the heavy chain of 8F5 (SEQ ID NO: 42) and the light chain of 8F5 (SEQ ID NO: 46).

FIG. 6F shows amino acid sequence (SEQ ID NOS: 78 and 79) of a variable region of 3B1 antibody, i.e., the heavy chain of 3B1 (SEQ ID NO: 50) and the light chain of 3B1 SEQ ID NO: 54).

FIG. 6G shows amino acid sequence (SEQ ID NOS: 80 and 81) of a variable region of 41H8 antibody, i.e., the heavy chain of 41H8 (SEQ ID NO: 58) and the light chain of 41H8 (SEQ ID NO: 62).

FIG. 10B shows results of measurements of HDL-c blood concentration after we administer to rabbit 47B2 and 8F5 antibody. Vertical axis of the graph shows concentration of blood HDL-c against concentration of blood HDL-c of first day, and horizontal axis of the graph shows number of days after antibody administration.

FIG. 11A (SEQ ID NOS: 82-88) shows an alignment of the amino acid sequences of seven antibody heavy chains, i.e., 12B10 (SEQ ID NO: 6), 47B2 (SEQ ID NO: 18), 25E4 (SEQ ID NO: 26), 16A11 (SEQ ID NO: 34), 8F5 (SEQ ID NO: 42), 3B1 (SEQ ID NO: 50), and 41H8 (SEQ ID NO: 58).

FIG. 11B (SEQ ID NOS: 89-95) shows an alignment of the amino acid sequence of seven antibody light chains, i.e., 12B10 (SEQ ID NO: 10), 47B2 (SEQ ID NO: 22), 25E4 (SEQ ID NO: 30), 16A11 (SEQ ID NO: 38), 8F5 (SEQ ID NO: 46), 3B1 (SEQ ID NO: 54), and 41H8 (SEQ ID NO: 62).

MODE FOR CARRYING OUT THE INVENTION

Figure 1:
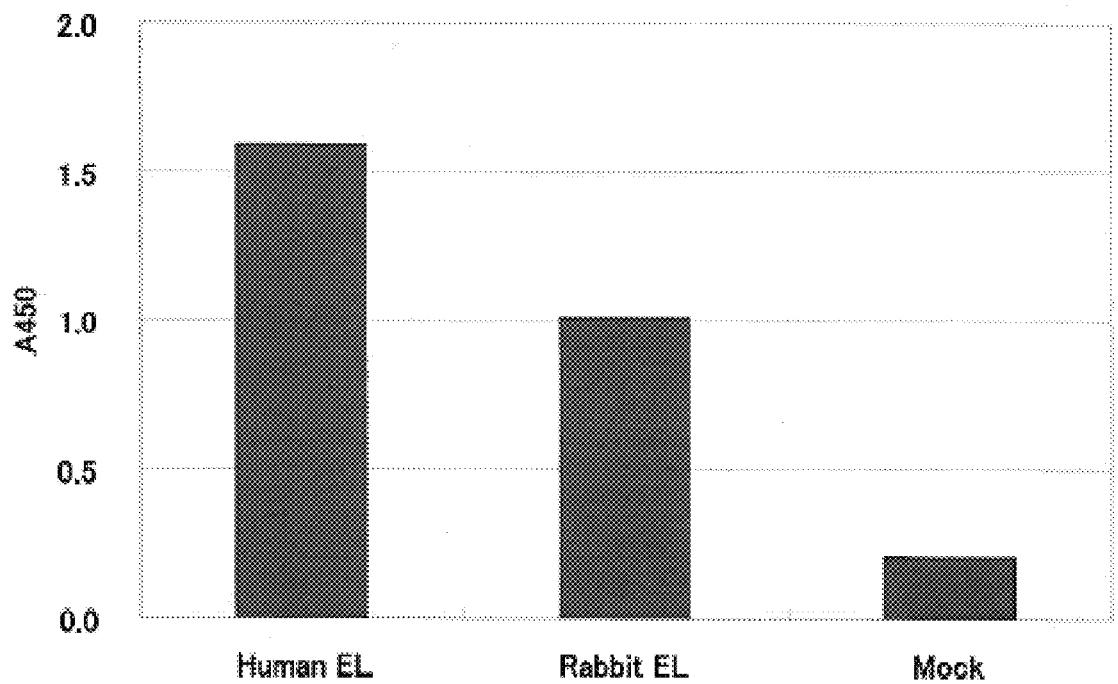
FIG. 1 shows results of measurements of the binding activity of 12B10 antibody and human or rabbit EL in the ELISA which uses human EL and rabbit EL as an antigen. It is confirmed that 12B10 antibody binds human EL and rabbit EL. Vertical axis of the graph shows absorbance in 450nm.

The present invention provides a monoclonal antibody that is characterized of selectively inhibiting enzyme activity of EL.

It is important to use consecutive amino acid residues containing amino acid sequence at positions of 331 to 459 region in amino acid sequence of SEQ ID NO: 1 to produce a monoclonal antibody of the present invention. The length is not particularly limited, but six or more residues which have immunogenicity are desired. We can use naturally or artificially highly expressed cell lines, these membrane fractions, these purified products, fusion proteins with other proteins or peptides (for examples, tag proteins such as FLAG-tag, HIS-tag, GST-tag or C2tag etc. or fluorescent proteins such as GFP or EGFP etc.), or chemically synthesized peptides as specific examples of these antibodies. In addition, preparation methods of these immunogens are known to those skilled in the art.

The monoclonal antibody of the present invention may be prepared by an existent commonly used production. Concretely, a mammal, preferably, mouse, rat, hamster, guinea pig, rabbit, cat, dog, pig, goat, sheep, donkey, horse or bovine, more preferably mouse, rat, hamster, guinea pig or rabbit is immunized with an immunogen of the present invention, together with Freund's adjuvant as necessary, by one or several times of subcutaneous, intramuscular, intravenous, intrafootpad or intraperitoneal injection. Usually, immunization is conducted once to four times every about 1 to 21 days after primary immunization, and antibody producing cells may be acquired from the immunized mammal after about 1 to 10 days from the final immunization. The number of times and time interval of immunization may be appropriately changed depending on the property of the immunogen being used.

Hybridoma that secrets monoclonal antibody may be prepared according to the Kohler and Milstein's method (Nature, 1975, vol. 256, p. 495-497) and a corresponding method. That is, hybridoma may be prepared by cell fusion between an antibody producing cell contained in spleen, lymph node, bone marrow, tonsil or the like, preferably in spleen acquired from a mammal immunized as described above, and a myeloma cell lacking autoantibody producing ability derived, preferably from a mammal such as mouse, rat, guinea pig, hamster, rabbit or human, more preferably from mouse, rat or human.

As a myeloma cell used in cell fusion, generally, cell lines obtained from mouse, for example, P3-U1, NS-1, SP-2, 653, X63, AP-1 and the like may be used.

Hybridoma that produces monoclonal antibody is screened by culturing a hybridoma, for example, in a microtiter plate, measuring reactivity to an immunogen used in mouse immunization as described above in culture supernatant in the well where proliferation is observed, by a measuring method such as RIA, ELISA or FACS and selecting a clone that produces a monoclonal antibody exhibiting specific affinity with the immunogen or hapten. Then, usually used is a method wherein an immunogen is solid-phased, and an antibody in culture supernatant that binds to the solid-phased immunogen is detected by an anti-mouse secondary antibody labeled with a radioactive substance, a fluorescent substance or an enzyme. Further in the case of using the cells expressing the immunogen, we add to the cells the hybridoma culture supernatant, then after reacting with secondary antibodies labeled with a fluorescent, we can detect a monoclonal antibody of the present invention that binds to the immunogen on the cell membrane by measuring fluorescence intensity of the cells with fluorescence detection apparatus flow cytometry or the like.

Production of monoclonal antibody from selected hybridoma may be achieved by culturing hybridoma in vitro or in ascites of mouse, rat, guinea pig, hamster or rabbit, preferably of mouse or rat, or more preferably of mouse, followed by isolation from the obtained culture supernatant or ascites of mammal. In the case of in vitro culture, the hybridoma may be cultured in a known nutrient medium or in any nutrient cultures derived and prepared from a known base medium used for proliferating, maintaining and storing hybridoma and for producing monoclonal antibody in culture supernatant, depending on various conditions such as property of cultured cell species, object of the test research and culturing method.

As a base medium, for example, low-calcium media such as Ham'F12 medium, MCDB153 medium or low-calcium MEM culture, and high-calcium media such as MCDB104 medium, MEM medium, D-MEM medium, RPMI1640 medium, AF104 medium, or RD medium can be recited, and such a base medium may contain, for example, serum, hormone, cytokine and/or various inorganic or organic substances depending on the object.

Isolation and purification of monoclonal antibody may be achieved by subjecting the culture supernatant or ascites as described above to saturated ammonium sulfate, ion exchange chromatography (e.g., DEAE or DE52), affinity column chromatography such as anti-immunoglobulin column or protein A column or the like.

As a monoclonal antibody of the present invention, a recombinant antibody that is produced using gene recombination technique in such a manner that an antibody gene is cloned from antibody producing cell, for example, hybridoma, and incorporated into an appropriate vector, and the vector is introduced into a host may be used (for example, Carl et al., THERAPEUTIC MONOCLONAL ANTIBODIES, published in 1990).

Concretely, from a hybridoma that produces an objective antibody, or from an immune cell that produces an antibody, for example, from a cell obtained by immortalizing sensitized lymphocyte or the like by cancer gene or the like, mRNA encoding a variable region (V region) of antibody is isolated. In isolation of mRNA, whole RNA is prepared by a known method, for example, by guanidine ultracentrifugation (Chirgwin, J. M. et al., Biochemistry (1979) 18, 5294-5299) or the like, and mRNA is prepared by using mRNA Purification Kit (available from Pharmacia) or the like.

From the obtained mRNA, cDNA of antibody V region is synthesized using a reverse transcriptase. Synthesis of cDNA may be conducted using AMV Reverse Transcriptase First-strand cDNA Synthesis Kit or the like. Further, for synthesis and amplification of cDNA, 5'-Ampli FINDER RACEKit (available from Clonetech) and 5'-RACE method using PCR (Frohman, M. A. et al, Proc. Natl. Acad. Sci. USA 1988, vol. 85, p. 8998) may be used. An objective DNA fragment is purified from the obtained PCR product, and connected with vector DNA. A recombinant vector is thus created and introduced into *E. coli* or the like, and a colony is selected and a desired recombinant vector is prepared. DNA base sequence of objective DNA is verified by a known method, for example, by deoxy method.

If DNA encoding V region of objective antibody is obtained, the DNA is connected with DNA encoding a desired antibody constant region (C region), and incorporated into an expression vector. Alternatively, DNA encoding V region of antibody may be incorporated into an expression vector containing DNA of antibody C region. For production of antibody used in the present invention, antibody gene is incorporated into an expression vector in such a manner that it is expressed under control of an expression control region, for example, enhancer/promoter. Next, a host cell can be transformed with this expression vector to cause expression of antibody.

For expression of antibody gene, heavy chain (H chain) or light chain (L chain) of antibody may be separately incorporated into expression vectors, or a host may be co-transformed with these expression vectors, or DNA encoding H chain and L chain may be incorporated into a single expression vector to transform a host with the resultant expression vector (see WO94/11523).

Preparation method of a monoclonal antibody of the present invention other than the above can be also used so called phage display technology. Concretely, for example antibody gene library prepared as a material human or animal (for example, rabbit, mouse, rat, hamster or the like) B lymphosate by known method or completely synthesized antibody gene library prepared from selected and modified human or animal germ line sequence is presented to the cell surface, on the ribosome or the like of bacteriophage, *Escherichia coli*, yeast, animal cells or the like. In this case, the forms of the antibody to be presented on the cell surface are listed IgG molecules, IgM molecules, Fab fragments, single chain Fv (scFv) fragments, etc.

We can obtain antibody genes by rearranging thus obtained monoclonal antibody fragment to the corresponding region of the IgG antibody gene by a known method. And we incorporate thus genes obtained in this manner into a suitable vector, introduce the vector into the host, we can prepare the antibody with recombinant DNA techniques (for examples, see Carl et. al. THERAPEUTIC MONOCLONAL ANTIBODIES, 1990 issue).

The antibody of the present invention is characterized of selectively inhibiting enzyme activity of EL. Below, we show an example of a procedure for measuring ability of inhibiting enzyme activity of EL.

The DNA encoding EL is cloned into pcDNA3.1 expression vector (Invitrogen). The expression vector is transfected into HEK293F cells and culture at 37° C., 8% CO2 for 2 days. The cell cultures are centrifuged, the cells are collected, the cells are suspended with PBS containing 20 U/mL of Heparin. The cell suspension is incubated at 37° C. for 45 min. The supernatant obtained by removing cells with centrifugation is used as human EL enzyme solution to measure inhibitory activity.

After adding a monoclonal antibody to the solution containing 20 mM Tris-HCl Buffer (pH 7.5), 0.5% bovine serum albumin, 4 mM CaCl2, 150 mM NaCl and 2 mg/mL human HDL (Athens Research&Techonology), EL enzyme solution is added. After reaction at 37° C. for 2 hr, free fatty acid (NEFA) made from HDL by EL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of the antibody. The concentration where 50% of the antibody is inhibited can be calculated from the inhibition curve.

Effective concentration (IC50) of antibody which shows 50% inhibition of EL enzyme activity inhibition is often used as an indicator of EL inhibitory activity.

And a monoclonal antibody of the present invention is characterized of selectively inhibiting enzyme activity of EL. Below, we show an example of a confirmation procedure for measuring ability of inhibiting enzyme activity of EL.

The DNA encoding HL is cloned into pcDNA3.1 expression vector (Invitrogen). The expression vector is transfected into HEK293F cells and culture at 37° C., 8% CO2 for 2 days. The cell cultures are centrifuged, the cells are collected, the cells are suspended with PBS containing 20 U/mL of Heparin. The cell suspension is incubated at 37° C. for 45 min. The supernatant obtained by removing cells with centrifugation is used as human HL enzyme solution. LPL enzyme solution is prepared by using the same procedures. After adding a monoclonal antibody to the solution containing 20 mM Tris-HCl Buffer (pH 7.5), 0.5% bovine serum albumin, 4 mM CaCl2, 150 mM NaCl and 0.5 mg/mL human VLDL (INTRACEL), HL or LPL enzyme solution is added. After reaction at 37° C. for 2 hr, free fatty acid (NEFA) made from VLDL by HL or LPL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of antibody.

In the case of inhibiting not more than 3% LPL or HL enzyme activities, when adding the monoclonal antibody corresponding to IC50 against EL, means to have a selective inhibitory activity against EL enzyme.

It is preferable that an epitope region is the region that EL has not homology with LPL or HL because a monoclonal antibody of the present invention is characterized of not inhibiting enzyme activity of LPL and HL, and is characterized of selectively inhibiting enzyme activity of EL.

A monoclonal antibody of the present invention includes gene recombinant-type monoclonal antibodies that are artificially modified for the purpose of lowering heterologous antigenicity against human, for example, chimera monoclonal antibody, humanized monoclonal antibody and human monoclonal antibody.

A monoclonal antibody of the present invention may be a conjugate antibody bound to various molecules such as polyethylene glycol (PEG), radioactive material, toxin. These conjugate antibodies can be obtained by chemically modifying obtained antibodies. These conjugate antibodies are included in a monoclonal antibody of the present invention.

And a monoclonal antibody of the present invention may fuse to the other proteins at the N terminal or C terminal of the antibody (Clinical Cancer Research, 2004, 10, 1274-1281). Those skilled in the art may properly select fusion protein.

In the present invention, "a monoclonal antibody fragment" means a part of the above-mentioned monoclonal antibody of the present invention and has the specific bindability to EL as with the monoclonal antibody, or means a fragment that has the specific bindability to EL as with the monoclonal antibody and has the effect of the inhibiting EL enzyme activity as with the monoclonal antibody. Concretely, fragments that have specific associativity against EL are listed Fab, F(ab')$_2$, Fab', single chain antibody (scFv), disulfide stabilized antibody (dsFv), dimerized V region fragment (Diabody), peptide containing CDR, etc. (Expert opinion on therapeutic patents, vol. 6, No. 5, p. 441-456, 1996).

A monoclonal antibody of the present invention or a fragment thereof is useful as a pharmaceutical composition. Therefore, a pharmaceutical composition containing a monoclonal antibody and a fragment thereof may be administered systemically or topically by in an oral or parenteral route. For parenteral administration, for example, intravenous injection such as drip infusion, intramuscular injection, intraperitoneal injection, subcutaneous injection, intranasal administration, inhalation and the like can be selected.

Also, a monoclonal antibody of the present invention is applicable to the diagnostic for dyslipidemia, hyperlipidemia, arteriosclerosis, atherosclerosis, hypercholesterolemia, hypertriglyceridemia, diabetes, obesity and/or syndrome X because a monoclonal antibody of the invention has the specific bindability to against EL.

A monoclonal antibody of the present invention or a fragment thereof is characterized of binding to positions of 331 to 459 region in amino acid sequence of SEQ ID NO: 1. Binding to positions of 331 to 459 region in amino acid sequence of SEQ ID NO: 1 means that a monoclonal antibody or a fragment thereof binds to any amino acid sequence in the region, and does not mean that a monoclonal antibody or a fragment thereof binds to all amino acid sequence in the region.

An object patient of the pharmaceutical composition of the present invention is assumed arteriosclerosis and metabolic syndrome. Effective dose is selected in the range of 0.01 mg to 100 mg per 1 kg of body weight per one time. Alternatively, a dose of 5 to 5000 mg, preferably a dose of 10 to 500 mg per a patient may be selected. However, a dose of the pharmaceutical composition containing the monoclonal antibody of the present invention or a fragment thereof is not limited to these doses. Administering duration may be also appropriately selected depending on the age, symptom and the like of the patient. The pharmaceutical composition of the present invention may also include a pharmaceutically acceptable carrier or additive as well depending on the route of administration. Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but, it is not limited thereto.

The present invention is described below in more detail by the way of examples. However, the present invention is not limited to the following examples. Unless specifying otherwise as a procedure for preparing antibody, we used methods described in Immunochemistry in Practice (Blackwell Scientific Publications). Also unless specifying otherwise as the genetic engineering techniques, we used methods described in Molecular Cloning: A Laboratory Manual, $2^{nd}$ Edition (Cold Spring Harbor Laboratory).

EXAMPLE 1

Preparation of Recombinant Adenovirus to Express Human EL

The cDNA of human EL with C2 tag (SEQ ID NO: 3) was cloned into pShuttle vector (Clontech). This sub-cloned vector and the vector carrying adenoviral backbone gene was digested by PI-SceI and I-CeuI enzyme (Adeno-x Accessory Kit, Clontech). The ligation reaction of the digested fragments was conducted at 16° C. for 3 hrs (Ligation high, TOYOBO) and the ligation products were transformed to *E. coli* (OneShot stb13 Chemically Competent, Invitrogen). After selection of Ampicillin, plasmid DNA was purified from obtained clone (QIAprep spin Miniprep Kit, QIAGEN) and was digested by PacI enzyme to cut *E. coli* growth area (New England Biolabs). With the above, plasmid DNA was acquired to generate adenovirus vector. Acquired plasmid DNA was transfected to HEK293 cells (dispensed from human science promotion foundation) using Lipofectamine 2000 (Invitrogen) and cultured in DMEM containing 10% FBS at 37° C. After transfection, we changed culture medium every 5 days and we continued to culture cells until confirming cytopathic effect (CPE). After confirming CPA, the cells and culture supernatant were collected. After the cells were subjected to five rounds of freeze/thaw with dry ice-methanol bath and warm bath, supernatant which was obtained by 15 min centrifugation was collected as cell extracts. The culture supernatant was mixed with the culture medium and used as a primary virus stock. Amplification of the virus stock was achieved by adding the virus stock to HEK293 cells and repeating same procedures. After amplification of the virus stock, the finally obtained cell extracts was treated with Benzonase (Merck-Novagen) for 30 min at 37° C., then supernatant was used for the purification of viral vector by following density gradient centrifugation. We overlaid PBS containing 1.5, 1.35, 1.25 g/cm³ cesium chloride into the centrifuging tube, then overlaid the supernatant. We centrifuged this at 35,000 rpm for 1 hr at 16° C., and collected obtained virus vector by visual. Collected viral vector was dialyzed against PBS containing 10% glycerol, and then used as purified adenoviral vectors. A part of viral vector was used for titration (Adeno-X rapid titer kit, Clontech) and self proliferative potential gain-of-emergence decision, and only used to immunize the following only those without abnormal.

EXAMPLE 2

Preparation of the Cells that Express Human EL and Human EL Lysate

We added C2 tag (SEQ ID NO: 3) to 3' end of DNA encoding human EL, added the DNA fragment to pcDNA3.1 (Invitrogen) using restriction enzyme site of HindIII and XbaI, constructed expression plasmid that expressed EL to prepare human EL-C2 tag. The human EL expression vector was transfected into HEK293 cells with Lipofectamine-2000 (Invitrogen). After 48 hr culture, HEK293 cells were collected and used as human EL-overexpressed cells. The cells were lysed with Lysis buffer containing 1% TritonX-100, 100 mM NaCl and 25 mM Tris/HCl (pH8.0). The supernatant was collected using centrifugation and used as human EL lysate. The rabbit EL lysate was prepared in the same method.

The amino acid sequence of human EL-C2 tag was described in SEQ ID NO: 1 and that of rabbi EL-C2 tag was described in SEQ ID NO: 2.

EXAMPLE 3

Preparation of Human EL Fragment 411-500 (SEQ ID NO:4) and 411-459 (SEQ ID NO:5)

We added his tag to 5' end of cDNA containing amino acids that positioned 411 to 500 in amino acid sequence of SEQ ID NO: 1 and C2 tag to 3' end end of cDNA containing amino acids that positioned 411 to 500 in amino acid sequence of SEQ ID NO: 1, this was cloned into expression vector pcDNA3.3 (Life technologies), and used as human EL_411-500 fragment expression vector. We prepared human EL_411-459 fragment expression vector in the same method. Each expression vector was transfected into HEK293 cells using Lipofectamine 2000 (Life technologies). After culturing for 48 hours, the cells were lysed with Lysis buffer (25 mM Tris/HCl, pH8.0 containing 1% TritonX-100 and 100 mM NaCl). After centrifugation, the supernatant was collected. The supernatant were used as human EL_411-500 fragment lysate and human EL_411-459 fragment lysate.

EXAMPLE 4

Immunization of Human EL Expression Adenoviral Vector 8 week-old female mice (BALB/cAnCrlCrljs spices, obtained from Nihon LSC) were immunized intravenously, subcutaneously or intramuscularly with $2 \times 10^9$ i.f.u. adenovirus vector carrying purified human EL gene. Every 7 days after administration, the blood sample was taken from tail vein and the antibody titer was measured. And, additional administration of adenovirus vector carrying human EL gene. The mice which showed high titer were booster immunized from tail vein as the final administration.

EXAMPLE 5

Production of Hybridoma Producing Antibodies

We opened the stomach of the mouse which showed high titer, extracted the spleen and collected spleen cells three days after final immunization. Spleen cells and mouse myeloma cells (p3×63-Ag8.U1, Tokyosyuyokenkyusyo) were fused using 50% polyethylene glycol 4000, and hybridoma cells were selected in a culture medium containing hypoxanthine, aminopterin and thymidine.

EXAMPLE 6

Screening of Hybridoma which Produced Anti-human EL Antibodies

Ten days after the cell fusion, hybridoma cells which produced selective antibodies were selected. Each well of 384 well microtiter plates (Nunc) was immobilized with 35 μL of Tris/HCl buffer (50 mM Tris/HCl, pH7.5) containing 0.35 μg of anti-mouse IgG Fc (Jackson Immuno Research). The plates were incubated at 4° C. for 16 hr. After washing the wells one time with 90 μL, of washing solution (saline containing 0.01% Tween20), 100 μL of Block-Ace (Dainihonsumitomo) was added to the wells and incubated at room temperature for 2 hr (immobilized plate of anti-mouse IgG-Fc antibody). After washing the wells three times with 90 μL of washing buffer, 15 μL of assay buffer containing human EL lysate (50 mM Tris/HCl, PH 7.4 containing 4% Block-Ace, 0.05% Tween20, 150 mM NaCl) were added to the wells and incubated at room temperature at 4° C. for 16 hr. After washing the wells three times with 90 μL of washing buffer, 15 μL assay buffer containing biotin-labeled anti-C2-tag antibody and HRP-labeled Streptavidin were added to the wells and incubated at room temperature for 1 hr. After washing the wells three times with 90 μL of washing buffer, 15 μL of TMB+-Substrate-Chromogen (DAKO) was added and incubated at room temperature for 30 min. The reaction was stopped with adding 15 μL of 0.05M $H_2SO_4$ and then measured absorbance 450 nm. From the result of screening, the hybridoma (12B10) which produced anti-human EL antibody was selected. The antibody which was produced by hybridoma of 12B10 was named 12B10 antibody. The IgG subclass of 12B10 antibody was determined to be IgG2a using Mouse Immunoglobulin Isotyping Kit (BD Biosciences).

EXAMPLE 7

Measurement of Binding Activity of 12B10 Antibody to Human EL and Rabbit EL

Assay buffer containing 15 μl of 12B10 antibody (1 μg/mL) was added to immobilized plate of anti-mouse IgG-Fc antibody, and incubated for 2 hr. After washing the wells three times with 90 μL of washing buffer, 15 μl of human EL lysate, rabbit EL lysate or mock lysate (negative control) was added and incubated at 4° C. for 16 hr. After washing the wells three times with 90 μL of washing buffer, 15 μl of assay buffer containing biotin-labeled anti-C2-tag antibody and HRP-labeled Streptavidin were added to the wells and incubated at room temperature for 1 hr. After washing the wells three times with 90 μL of washing buffer, 15 μL of TMB+-Substrate-Chromogen (DAKO) was added and incubated at room temperature for 30 min and then 15 μL of 0.05M $H_2SO_4$ was added and measured absorbance 450 nm. As a result, 12B10 antibody showed to bind human EL and rabbit EL (FIG. 1).

EXAMPLE 8

Measurement of Inhibitory Activity of 12B10 Antibody Against EL

The DNA encoding human EL or rabbit EL was cloned into pcDNA3.1 expression vector (Invitrogen). The expression vector was transfected into HEK293F cells and cultured at 37° C., 8% CO2 for 2 days. The cell culture was centrifuged, the cells were collected, the cells were suspended with PBS containing 20 U/mL of Heparin. The cell suspension was incubated at 37° C. for 45 min. The supernatant obtained by removing cells with centrifugation was used as human EL enzyme solution.

Figure 2:
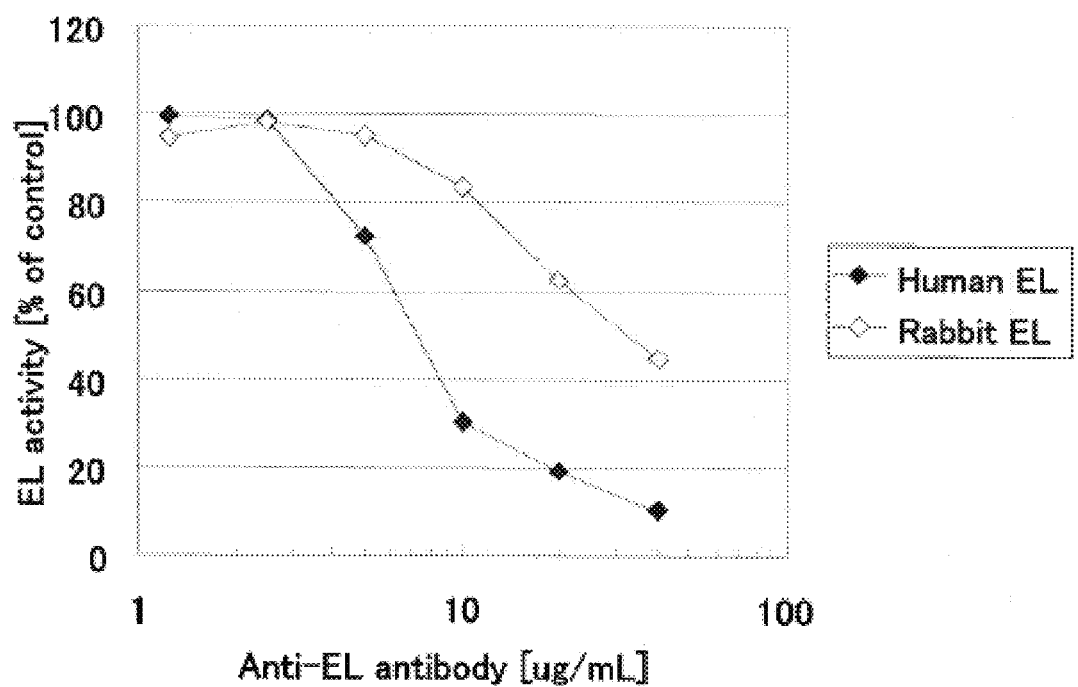
FIG. 2 shows results of measurements of the inhibiting activity of 12B10 antibody against human EL and rabbit EL. It is confirmed that human and rabbit EL activity are inhibited in a concentration-dependent manner of 12B10 antibody. Vertical axis of the graph shows specific activity (%) against the enzyme activity when 12B10 antibody is not added, and horizontal axis of the graph shows concentration (82g/ml) of the 12B10 antibody.

After adding 12B10 antibody to the solution containing 20 mM Tris-HCl Buffer (pH 7.5), 0.5% bovine serum albumin, 4 mM $CaCl_2$, 150 mM NaCl and 2 mg/mL human HDL (Athens Research&Techonology), human EL enzyme solution or rabbit EL enzyme solution was added (total volume 10 μl). After reaction at 37° C. for 2 hr, free fatty acid (NEFA) made from HDL was determined using NEFA C-test Wako (Wakojyunyakukougyo), the NFFA amount was used as enzyme activity index. Enzyme activity in the case of adding no 12B10 antibody was determined as control value and the specific activity was calculated against the control value at each concentration of the antibody. The concentration of 12B10 where 50% of EL activity was inhibited was calculated from the inhibition curve as IC50 value (FIG. 2). As a result, the IC50 values were 47 nM (human EL) and 201 nM (rabbit EL).

EXAMPLE 9

Measurement of Inhibitory Activity of 12B10 Antibody Against HL and LPL

The DNA encoding human HL was cloned into pcDNA3.1 expression vector (Invitrogen). The expression vector was transfected into HEK293F cells and cultured at 37° C., 8% $CO_2$ for 2 days. The cells were centrifuged and the cells ware collected, the cells were suspended with PBS containing 20 U/mL of Heparin (SIGMA). The cell suspension was incubated at 37° C. for 45 min. The supernatant obtained by removing cells with centrifugation was used as human HL enzyme solution. Rabbit HL, human LPL and rabbit LPL enzyme solution were prepared by using the same method.

Figure 3:
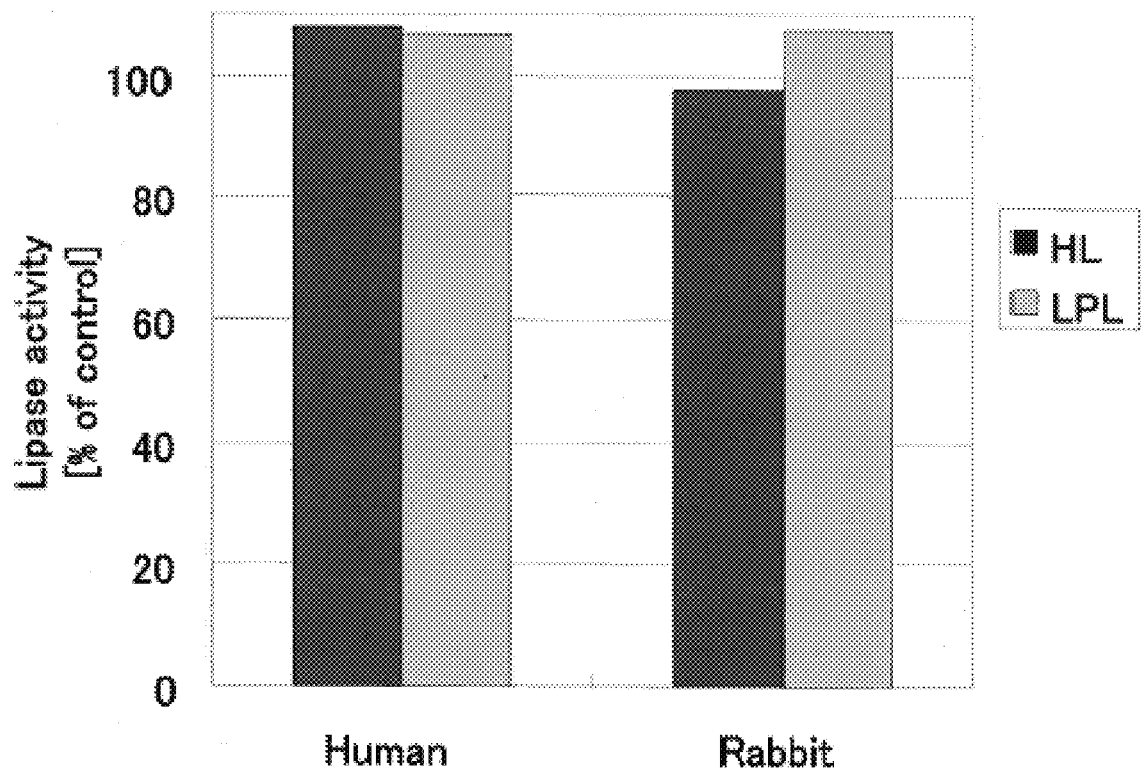
FIG. 3 shows results of measurements of the inhibiting activity of 12B10 antibody against human and rabbit HL, or against human and rabbit LPL. It is confirmed that 12B10 antibody does not inhibit human and rabbit HL and human and rabbit LPL. Vertical axis of the graph shows specific activity (%) against the enzyme activity when 12B10 antibody is not added.

After adding 12B10 antibody (final concentration 32 µg/ml) to the solution containing 20 mM Tris-HCl Buffer (pH 7.5), 0.5% bovine serum albumin, 4 mM $CaCl_2$, 150 mM NaCl and 0.5 mg/mL human VLDL (INTRACEL), human HL, rabbit HL, human LPL or rabbit LPL enzyme was added (total volume 10 µl). After reaction at 37° C. for 2 hr, free fatty acid (NEFA) made from VLDL by HL or LPL enzyme was determined using NEFA C-test Wako (Wakojyunyakukougyo), the NFFA amount was used as enzyme activity index. Enzyme activity in the case of adding no 12B10 antibody was determined as control value and the specific activity was calculated against the control value at each concentration of the antibody (FIG. 3). As a result, it was shown that 12B10 antibody didn't inhibit neither HL nor LPL enzyme activity.

EXAMPLE 10

Epitope Mapping of 12B10 Antibody

Figure 4:
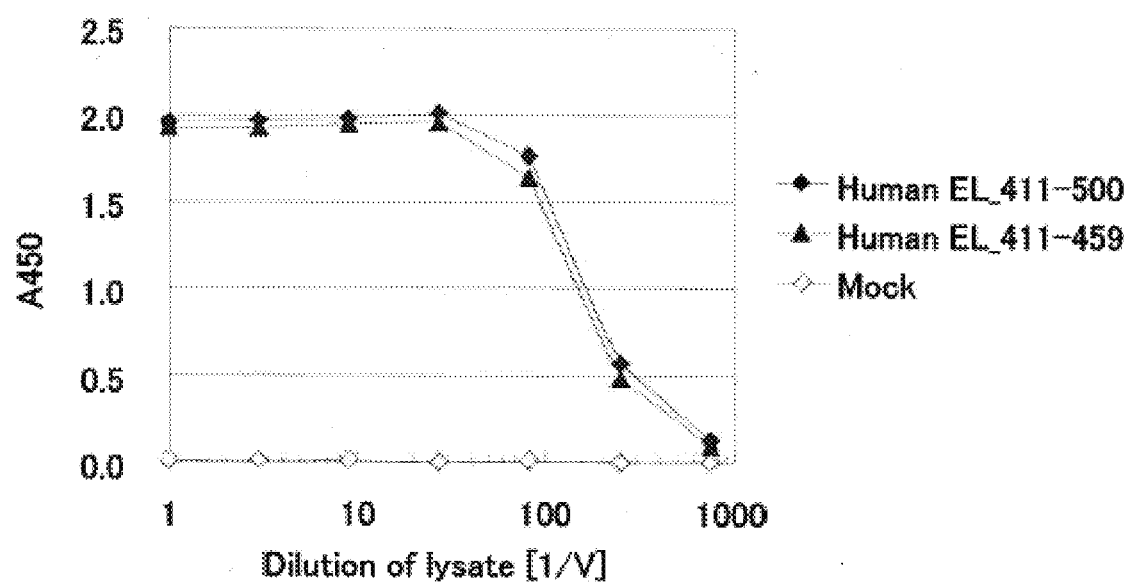
FIG. 4 shows results of measurements of the binding activity of 12B10 antibody and two kinds of human EL fragments in the ELISA which uses human EL fragments (human EL_411-500 or human EL_411-459) as an antigen. It is confirmed that 12B10 antibody binds human EL_411-500 and human EL_411-459. Vertical axis of the graph shows absorbance in 450nm, and horizontal axis of the graph shows magnification of the diluted of each lysate.

Assay buffer containing 15 µl of 12B10 antibody (5 µg/mL) was added to immobilized plate of anti-mouse IgG-Fc antibody and incubated for 2 hr. After washing the wells three times with 90 µL of washing buffer (Saline containing 0.01% Tween20), 15 µL of assay buffer (50 mM Tris/HCl, pH 7.4 containing 4% Block-Ace, 0.05% t ween20 and 150 mM NaCl) containing human EL fragment 411-500 or 411-459 lysate was added and incubated at 4° C. overnight. After washing the wells three times with 90 µl of washing buffer, 15 µL of assay buffer containing biotin-labeled anti-C2-tag (Fab) antibody and HRP-labeled Streptavidin (Thermo scientific) were added to the wells and incubated at room temperature for 1 hr. After washing the wells three times with 90 µl of washing buffer, 15 µL of TMB+-Substrate-Chromogen (DAKO) was added and incubated at room temperature for 30 min. The reaction was stopped with adding 15 µL of 0.05M $H_2SO_4$ and then measured absorbance 450 nm. As a result, it was shown that 12B10 bound both human EL 411-500 and human EL 411-459 (FIG. 4).

The alignment of human EL, human LPL and human HL was shown in FIG. 5A. The amino acids which were conserved at least 2 lipases were surrounded with solid lines. The amino acids of catalytic triad were shown with black star and the homology of surrounding areas of catalytic triad were high.

By contrast, the amino acids of the region which 12B10 antibody bound were surrounded with dashed lines and these regions showed low homology among human EL, human LPL and human HL. It was supposed that 12B10 antibody showed EL selective inhibition.

EXAMPLE 11

Analysis of Amino Acid Sequence of Variable Region of 12B10 Antibody

The amino acid sequence of variable region of 12B10 antibody was determined using common procedure (FIG. 6A). The amino acid sequence of heavy chain variable region of 12B10 antibody was shown in SEQ ID No: 6, the amino acid sequence of CDR1 of variable region was shown in SEQ ID No: 7, the amino acid sequence of CDR2 of variable region was shown in SEQ ID No: 8 and the amino acid sequence of CDR3 of variable region was shown in SEQ ID No: 9. The amino acid sequence of light chain variable region of 12B10 antibody was shown in SEQ ID No: 10, the amino acid sequence of CDR1 of variable region was shown in SEQ ID No: 11, the amino acid sequence of CDR2 of variable region was shown in SEQ ID No: 12 and the amino acid sequence of CDR3 of variable region was shown in SEQ ID No: 13.

EXAMPLE 12

Preparation of Adenovirus Expressing Baboon EL

The cDNA of baboon EL with C2 tag (SEQ ID NO: 3) was cloned into pShuttle vector (Clontech). This sub-cloned vector and the vector carrying adenoviral backbone gene was digested by PI-Scel and I-CeuI enzyme (Adeno-x Accessory Kit, Clontech). The ligation reaction of the digested fragments was conducted at 16° C. for 3 hrs (Ligation high, TOYOBO) and the ligation products were transformed to *E. coli* (OneShot stb13 Chemically Competent, Invitrogen). After selection of Ampicillin, plasmid DNA was purified from obtained clone (QIAprep spin Miniprep Kit, QIAGEN) and was digested by Pad enzyme to cut *E. coli* growth area (New England Biolabs). With the above, plasmid DNA was acquired to generate adenovirus vector. Acquired plasmid DNA was transfected to HEK293 cells (dispensed from human science promotion foundation) using Lipofectamine 2000 (Invitrogen) and cultured in DMEM containing 10% FBS at 37° C. After transfection, we changed culture medium every 5 days and we continued to culture cells until confirming cytopathic effect (CPE). After confirming CPA, the cells and culture supernatant were collected. After the cells were subjected to five rounds of freeze/thaw with dry ice-methanol bath and warm bath, supernatant which was obtained by 15 min centrifugation was collected as cell extracts. The culture supernatant was mixed with the culture medium and used as a primary virus stock. Amplification of the virus stock was achieved by adding the virus stock to HEK293 cells and repeating same procedures. After amplification of the virus stock, the finally obtained cell extracts was treated with Benzonase (Merck-Novagen) for 30 min at 37° C., then supernatant was used for the purification of viral vector by following density gradient centrifugation. We overlaid PBS containing 1.5, 1.35, 1.25 g/cm³ cesium chloride into the centrifuging tube, then overlaid the supernatant. We centrifuged this at 35,000 rpm for 1 hr at 16° C., and collected obtained virus vector by visual. Collected viral vector was dialyzed against PBS containing 10% glycerol, and then used as purified adenoviral vectors. A part of viral vector was used for titration (Adeno-X rapid titer kit, Clontech) and self proliferative potential gain-of-emergence decision, and only used to immunize the following only those without abnormal.

Baboon EL-C2 tag amino acid sequence is shown in SEQ ID No: 14.

EXAMPLE 13

Immunization of Baboon EL Expression Adenoviral Vector 8 week-old female mice (BALB/cAnCrlCrljs spices, obtained from Nihon LSC) were immunized intravenously, subcutaneously or intramuscularly with 2×10⁹ i.f.u. adenovirus vector carrying purified baboon EL gene. Every 7 days after administration, the blood sample was taken from tail vein and the antibody titer was measured. And, additional administration of adenovirus vector carrying baboon EL gene. The mice which showed high titer were booster immunized from tail vein as the final administration.

EXAMPLE 14

Production of Hybridoma Producing Antibodies

We opened the stomach of the mouse which showed high titer, extracted the spleen and collected spleen cells three days after final immunization. Spleen cells and mouse myeloma cells (p3×63-Ag8.U1, Tokyosyuyokenkyusyo) were fused using 50% polyethylene glycol 4000, and hybridoma cells were selected in a culture medium containing hypoxanthine, aminopterin and thymidine.

EXAMPLE 15

Preparation of EL Heparin Extract

The DNA encoding baboon EL was cloned into pcDNA3.1 expression vector (Invitrogen). The expression vector was transfected into HEK293F cells and cultured at 37° C., 8% $CO_2$ for 2 days. The cell culture was centrifuged, the cells were collected, the cells were suspended with PBS containing 20 U/mL of Heparin. The cell suspension was incubated at 37° C. for 45 min. The supernatant obtained by removing cells with centrifugation was used as baboon EL enzyme solution. Using the same method, cynomolgus monkey EL, rabbit EL, Mouse EL and human EL [331-459]-mouse EL heparin extract were prepared.

The amino acid sequence of cynomolgus monkey EL-C2 tag was shown in SEQ ID No: 15, mouse EL-C2 tag was shown in SEQ ID No: 16, human EL[331-459]-mouse EL-C2 tag was shown in SEQ ID No: 17.

EXAMPLE 16

Screening of a Hybridoma Cells which Produces Anti-baboonEL Antibodies

Ten days after the cell fusion, hybridoma cells which produced selective antibodies were selected. Each well of 384 well microtiter plates (Nunc) was immobilized with 35 µL of Tris/HCl buffer (50 mM Tris/HCl, pH7.5) containing 0.35 µg of anti-mouse IgG Fc (Jackson Immuno Research). The plates were incubated at 4° C. for 16 hr. After washing the wells one time with 90 µL of washing solution (saline containing 0.01% Tween20), 100 µL of Block-Ace (Dainihon-sumitomo) was added to the wells and incubated at room temperature for 2 hr (immobilized plate of anti-mouse IgG-Fc antibody). After washing the wells three times with 90 µL of washing buffer, 15 µL of assay buffer containing human EL lysate (50 mM Tris/HCl, PH 7.4 containing 4% Block-Ace, 0.05% Tween20, 150 mM NaCl) were added to the wells and incubated at room temperature at 4° C. for 16 hr. After washing the wells three times with 90 µL of washing buffer, 15 µL assay buffer containing biotin-labeled anti-C2-tag antibody and HRP-labeled Streptavidin were added to the wells and incubated at room temperature for 1 hr. After washing the wells three times with 90 µL of washing buffer, 15 µL of TMB+-Substrate-Chromogen (DAKO) was added and incubated at room temperature for 30 min. The reaction was stopped with adding 15 µL of 0.05M $H_2SO_4$ and then measured absorbance 450 nm. From the result of screening, the hybridomas (47B2, 25E4, 8F5, 3B1, 41H8) which produced anti-baboon EL antibody was selected. The antibody which was produced by hybridoma of 47B2, 25E4, 8F5, 3B1 and 41H8 were named respectively 47B2, 25E4, 8F5, 3B1 and 41H8 antibody. The IgG subclass of 47B2 antibody was determined to be IgG2a, the IgG subclass of 25E4 antibody was determined to be IgG2b, the IgG subclass of 8F5 antibody was determined to be IgG2a, the IgG subclass of 3B1 antibody was determined to be IgG1, the IgG subclass of 41H8 antibody was determined to be IgG1, using Mouse Immunoglobulin Isotyping Kit (BD Biosciences).

EXAMPLE 17

Immunization of EL C-terminal Fragment

The DNA encoding human EL C-terminal region was cloned into pGEX6P-1 expression vector (GE Healthcare). The expression vector was transfected into E. coli. BL21 Star strain (Life Technologies). The expression of EL C-terminal fragment was inducted by adding IPTG to culture medium of transformed E. coli. After overnight culture, E. coli pellet was collected, EL C-terminal fragment was purified using GSTrap column and the fragment was used as an antigen. 100 µg of the prepared EL C-terminal fragment and Freund's Complete Adjuvant were emulsified and intraperitoneally administered to 4 week-old female A/J Jms Slc spices mice as a first immunization. Afterwards, 100 µg of the prepared EL C-terminal fragment and Freund's Complete Adjuvant were administered to them 21 days, 42 days and 63 days after first immunization as additional immunizations. Further 100 µg of EL C-terminal fragment suspended in 0.1 mL saline was administered to them 84 days after first immunization as a final immunization. From the result of screening in the same way of example 16, the hybridoma (16A11) which produced anti-baboon EL antibody was selected. The antibody which was produced by hybridoma of 16A11 was named 16A11 antibody. The IgG subclass of 16A11 antibody was determined to be IgG1, using Mouse Immunoglobulin Isotyping Kit (BD Biosciences).

EXAMPLE 18

Measurement of Inhibitory Activity of Anti-EL Antibody Against EL

Figure 7A:
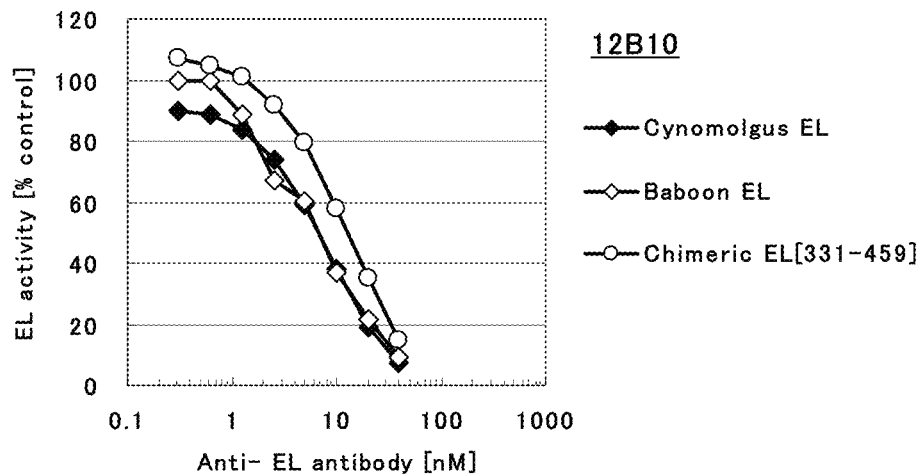
FIG. 7A shows results of measurements of the inhibiting activity of 12B10antibody against cynomolgus EL, baboon EL and human-mouse chimera EL. It is confirmed that these ELs activity are inhibited in a concentration-dependent manner of 12B10 antibody. Vertical axis of the graph shows specific activity (%) against the enzyme activity when 12B10 antibody is not added, and horizontal axis of the graph shows concentration (nM) of the 12B10 antibody.
Figure 7B:
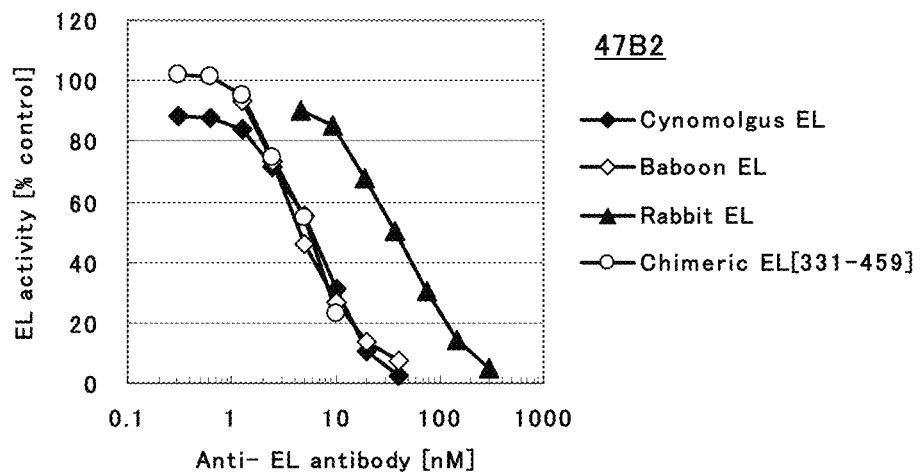
FIG. 7B shows results of measurements of the inhibiting activity of 47B2 antibody against cynomolgus EL, baboon EL, rabbit EL and human-mouse chimera EL. It is confirmed that these ELs activity are inhibited in a concentration-dependent manner of 47B2 antibody. Vertical axis of the graph shows specific activity (%) against the enzyme activity when 47B2 antibody is not added, and horizontal axis of the graph shows concentration (nM) of the 47B2 antibody.
Figure 7C:
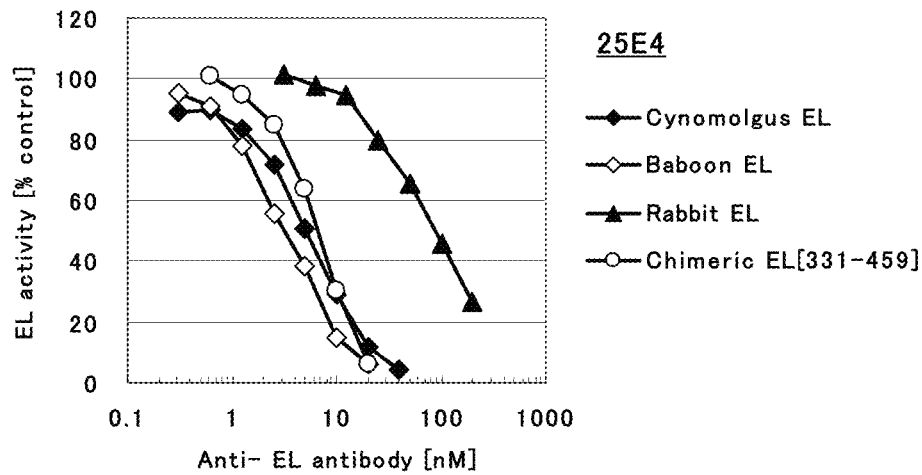
FIG. 7C shows results of measurements of the inhibiting activity of 25E4 antibody against cynomolgus EL, baboon EL, rabbit EL and human-mouse chimera EL. It is confirmed that these ELs activity are inhibited in a concentration-dependent manner of 25E4 antibody. Vertical axis of the graph shows specific activity (%) against the enzyme activity when 25E4 antibody is not added, and horizontal axis of the graph shows concentration (nM) of the 25E4 antibody.
Figure 7D:
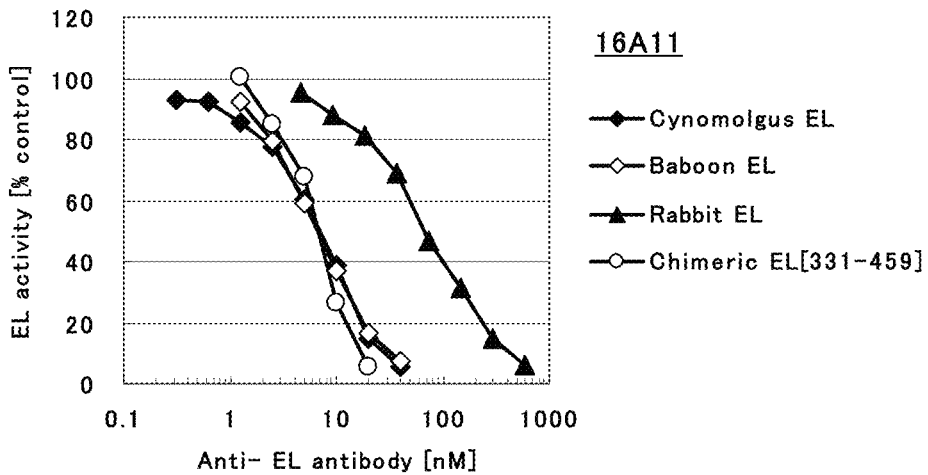
FIG. 7D shows results of measurements of the inhibiting activity of 16A11 antibody against cynomolgus EL, baboon EL, rabbit EL and human-mouse chimera EL. It is confirmed that these ELs activity are inhibited in a concentration-dependent manner of 16A11 antibody. Vertical axis of the graph shows specific activity (%) against the enzyme activity when 16A11 antibody is not added, and horizontal axis of the graph shows concentration (nM) of the 16A11 antibody.
Figure 7E:
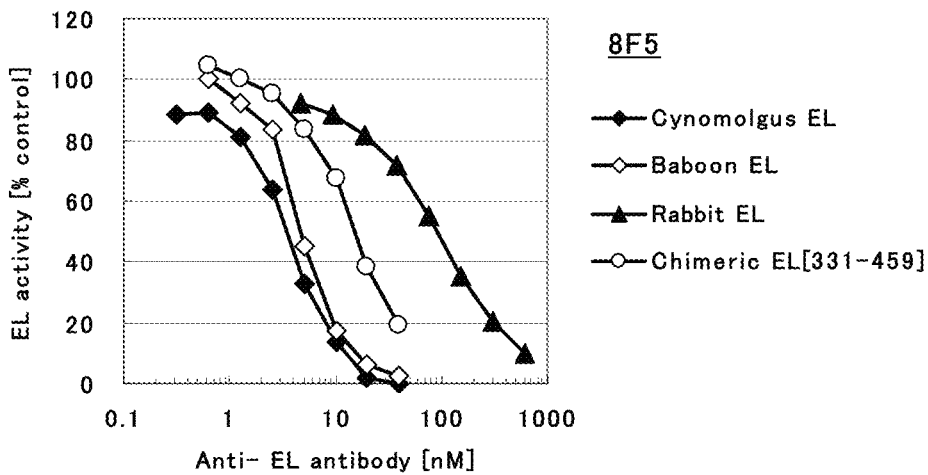
FIG. 7E shows results of measurements of the inhibiting activity of 8F5 antibody against cynomolgus EL, baboon EL, rabbit EL and human-mouse chimera EL. It is confirmed that these ELs activity are inhibited in a concentration-dependent manner of 8F5 antibody. Vertical axis of the graph shows specific activity (%) against the enzyme activity when 8F5 antibody is not added, and horizontal axis of the graph shows concentration (nM) of the 8F5 antibody.
Figure 7F:
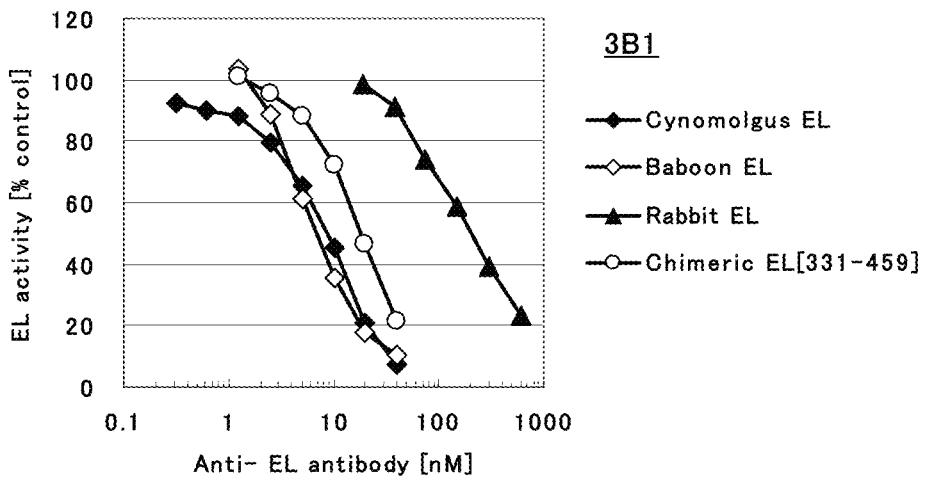
FIG. 7F shows results of measurements of the inhibiting activity of 3B1 antibody against cynomolgus EL, baboon EL, rabbit EL and human-mouse chimera EL. It is confirmed that these ELs activity are inhibited in a concentration-dependent manner of 3B1 antibody. Vertical axis of the graph shows specific activity (%) against the enzyme activity when 3B1 antibody is not added, and horizontal axis of the graph shows concentration (nM) of the 3B1 antibody.
Figure 7G:
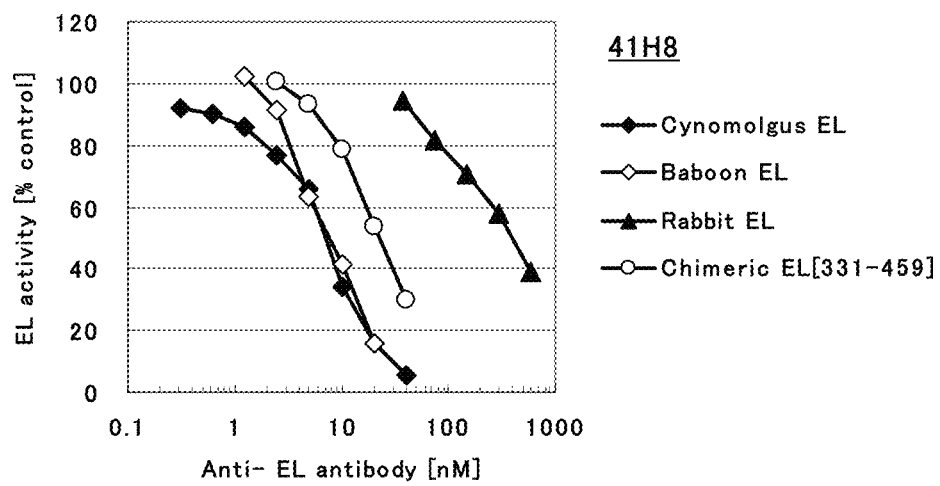
FIG. 7G shows results of measurements of the inhibiting activity of 41H8 antibody against cynomolgus EL, baboon EL, rabbit EL and human-mouse chimera EL. It is confirmed that these ELs activity are inhibited in a concentration-dependent manner of 41H8 antibody. Vertical axis of the graph shows specific activity (%) against the enzyme activity when 41H8 antibody is not added, and horizontal axis of the graph shows concentration (nM) of the 41H8 antibody.

The inhibitory activity of 12B10 antibody against cynomolgus monkey EL, baboon EL and human EL [331-459]-mouse EL was measured using the same method described Example 8. Enzyme activity in the case of adding no 12B10 antibody was determined as control value and the specific activity was calculated against the control value at each concentration of the antibody (FIG. 7A).

Also, the inhibitory activity of 47B2, 25E4, 16A11, 8F5, 3B1 and 41H8 antibody against cynomolgus monkey EL, baboon EL, rabbit EL and human EL [331-459]-mouse EL was measured using the same method described Example 8. Enzyme activity in the case of adding no antibody was determined as control value and the specific activity was calculated against the control value at each concentration of the antibody (FIG. 7B~G).

The concentration of each EL antibody where 50% of EL activity was inhibited was calculated from the inhibition curve as IC50 value and summarized in described table 1.

EXAMPLE 19

Measurement of Inhibitory Activity of Each Anti-EL Antibody Against HL and LPL

The DNA encoding human HL was cloned into pcDNA3.1 expression vector (Invitrogen). The expression vector was transfected into HEK293F cells and cultured at 37° C., 8% CO2 for 2 days. The cells were centrifuged and the cells ware collected, the cells were suspended with PBS containing 20 U/mL of Heparin (SIGMA). The cell suspension was incubated at 37° C. for 45 min. The supernatant obtained by removing cells with centrifugation was used as human HL enzyme solution. Human LPL enzyme solution was prepared by using the same method.

After adding anti-EL antibody to the solution containing 20 mM Tris-HCl Buffer (pH 7.5), 0.5% bovine serum albumin, 4 mM CaCl2, 150 mM NaCl and 0.5 mg/mL human VLDL (INTRACEL), human HL or human LPL enzyme was added (total volume 10 μl). After reaction at 37° C. for 2 hr, free fatty acid (NEFA) made from VLDL by HL or LPL enzyme was determined using NEFA C-test Wako (Wakojyu-nyakukougyo), the NFFA amount was used as enzyme activity index. Enzyme activity in the case of adding no anti-EL antibody was determined as control value and the specific activity was calculated against the control value at each concentration of the antibody (FIG. 8A~G). For comparison, the result was described side by side inhibition curve of rabbit EL. As a result, it was shown that 12B10, 47B2, 25E4, 16A11, 8F5, 3B1 and 41H8 antibodies didn't inhibit neither HL nor LPL enzyme activity.

Figure 8A:
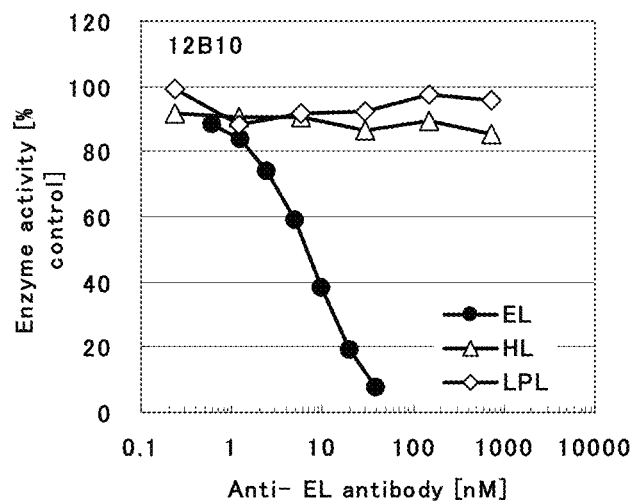
FIG. 8A shows results of measurements of the inhibiting activity of 12B10 antibody against human HL and human LPL. It is confirmed that 12B10 antibody dose not inhibit enzyme activity of human HL and human LPL, but 12B10 antibody inhibits enzyme activity of cynomolgus EL. Vertical axis of the graph shows specific activity (%) against the enzyme activity when 12B10 antibody is not added.
Figure 8B:
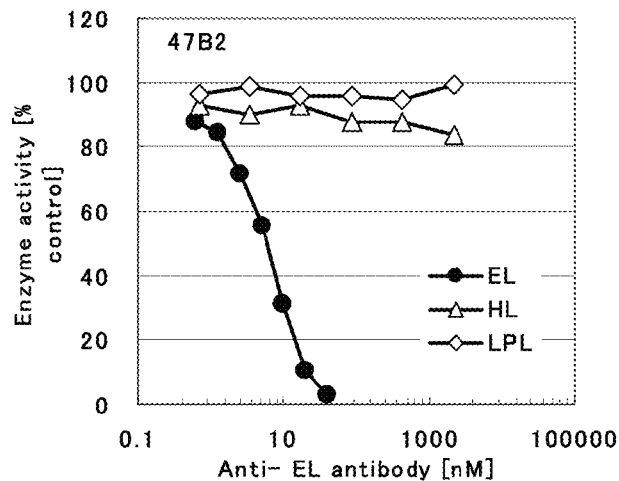
FIG. 8B shows results of measurements of the inhibiting activity of 47B2 antibody against human HL and human LPL. It is confirmed that 47B2 antibody dose not inhibit enzyme activity of human HL and human LPL, but 47B2 antibody inhibits enzyme activity of cynomolgus EL. Vertical axis of the graph shows specific activity (%) against the enzyme activity when 47B2 antibody is not added.
Figure 8C:
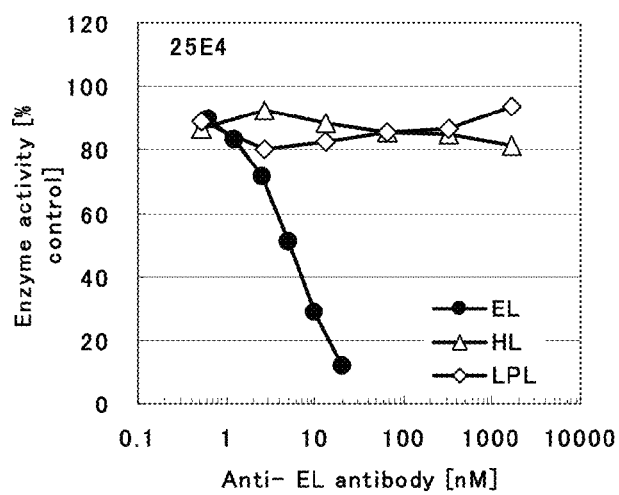
FIG. 8C shows results of measurements of the inhibiting activity of 25E4 antibody against human HL and human LPL. It is confirmed that 25E4 antibody dose not inhibit enzyme activity of human HL and human LPL, but 25E4 antibody inhibits enzyme activity of cynomolgus EL. Vertical axis of the graph shows specific activity (%) against the enzyme activity when 25E4 antibody is not added.
Figure 8D:
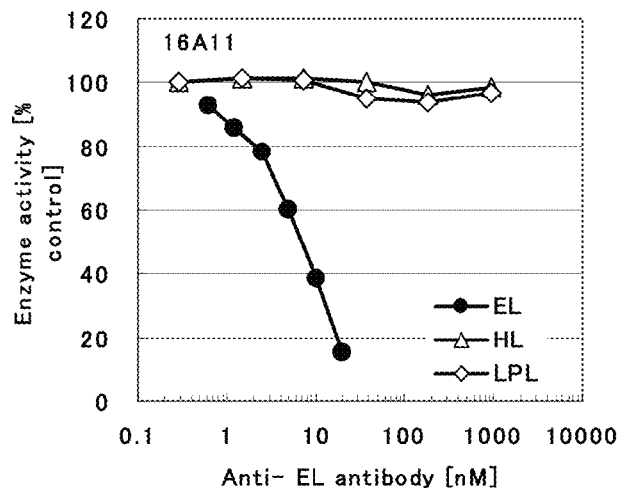
FIG. 8D shows results of measurements of the inhibiting activity of 16A11 antibody against human HL and human LPL. It is confirmed that 16A11 antibody dose not inhibit enzyme activity of human HL and human LPL, but 16A11 antibody inhibits enzyme activity of cynomolgus EL. Vertical axis of the graph shows specific activity (%) against the enzyme activity when 16A11 antibody is not added.
Figure 8E:
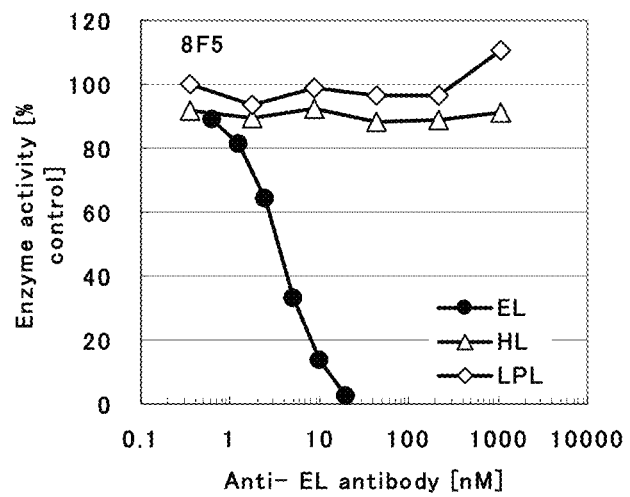
FIG. 8E shows results of measurements of the inhibiting activity of 8F5 antibody against human HL and human LPL. It is confirmed that 8F5 antibody dose not inhibit enzyme activity of human HL and human LPL, but 8F5 antibody inhibits enzyme activity of cynomolgus EL. Vertical axis of the graph shows specific activity (%) against the enzyme activity when 8F5 antibody is not added.
Figure 8F:
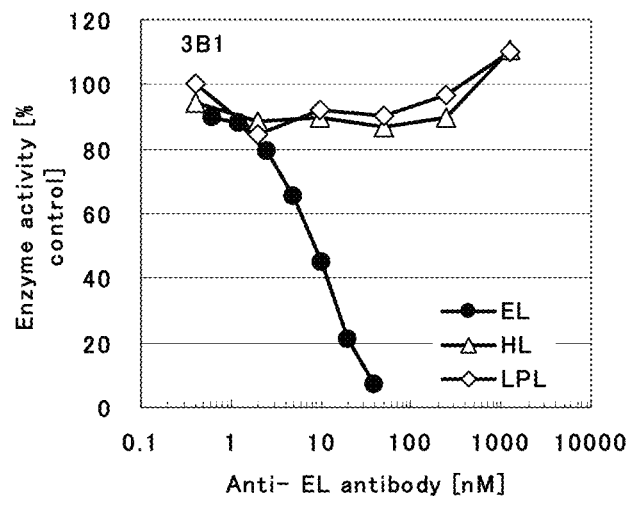
FIG. 8F shows results of measurements of the inhibiting activity of 3B1 antibody against human HL and human LPL. It is confirmed that 3B1 antibody dose not inhibit enzyme activity of human HL and human LPL, but 3B1 antibody inhibits enzyme activity of cynomolgus EL. Vertical axis of the graph shows specific activity (%) against the enzyme activity when 3B1 antibody is not added.
Figure 8G:
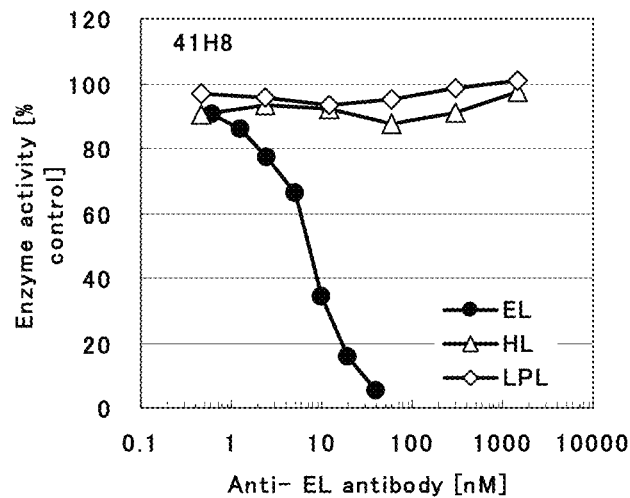
FIG. 8G shows results of measurements of the inhibiting activity of 41H8 antibody against human HL and human LPL. It is confirmed that 41H8 antibody dose not inhibit enzyme activity of human HL and human LPL, but 41H8 antibody inhibits enzyme activity of cynomolgus EL. Vertical axis of the graph shows specific activity (%) against the enzyme activity when 41H8 antibody is not added.
Figure 8H:
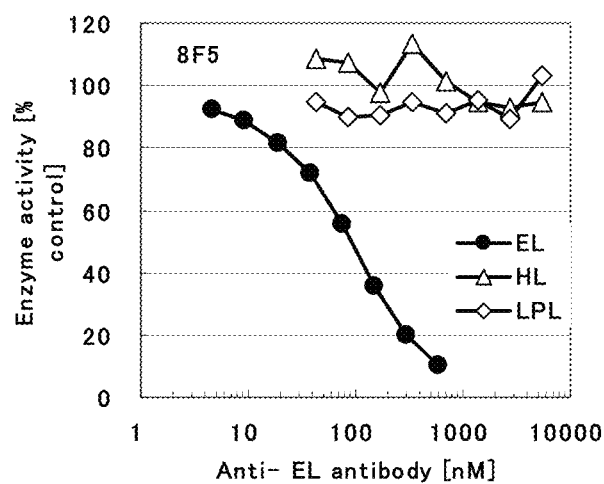
FIG. 8H shows results of measurements of the inhibiting activity of 8F5 antibody against human HL and human LPL. It is confirmed that 8F5 antibody dose not inhibit enzyme activity of human HL and human LPL, but 8F5 antibody inhibits enzyme activity of cynomolgus EL. Vertical axis of the graph shows specific activity (%) against the enzyme activity when 8F5 antibody is not added.
Figure 8I:
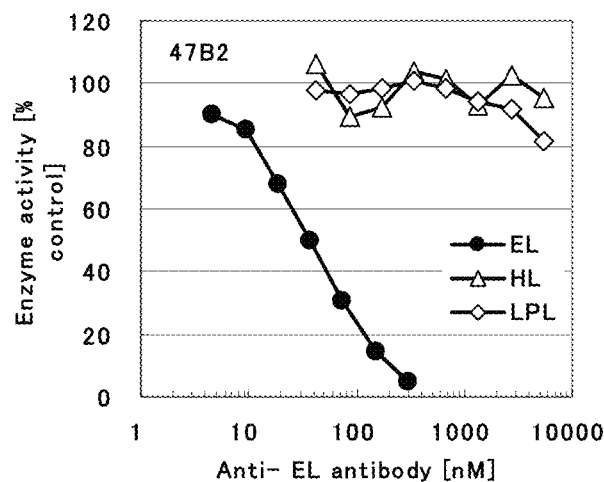
FIG. 8I shows results of measurements of the inhibiting activity of 47B2 antibody against human HL and human LPL. It is confirmed that 47B2 antibody dose not inhibit enzyme activity of human HL and human LPL, but 47B2 antibody inhibits enzyme activity of cynomolgus EL. Vertical axis of the graph shows specific activity (%) against the enzyme activity when 47B2 antibody is not added.
Figure 9A:
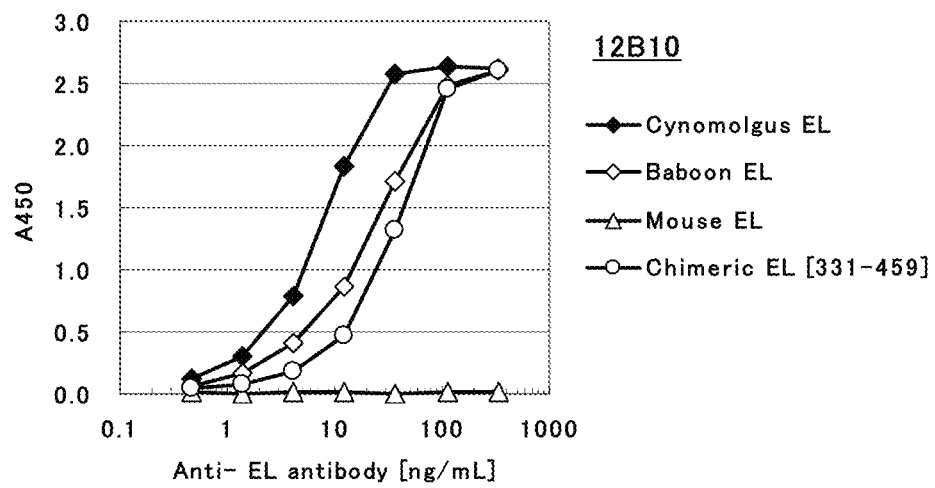
FIG. 9A shows results of measurements of the binding activity of 12B10 antibody against cynomolgus EL, baboon EL, mouse EL and human-mouse chimera EL. It is shown that 12B10 antibody binds cynomolgus EL, baboon EL and human-mouse chimera EL. Vertical axis of the graph shows absorbance, and horizontal axis of the graph shows concentration (ng/mL) of antibody.
Figure 9B:
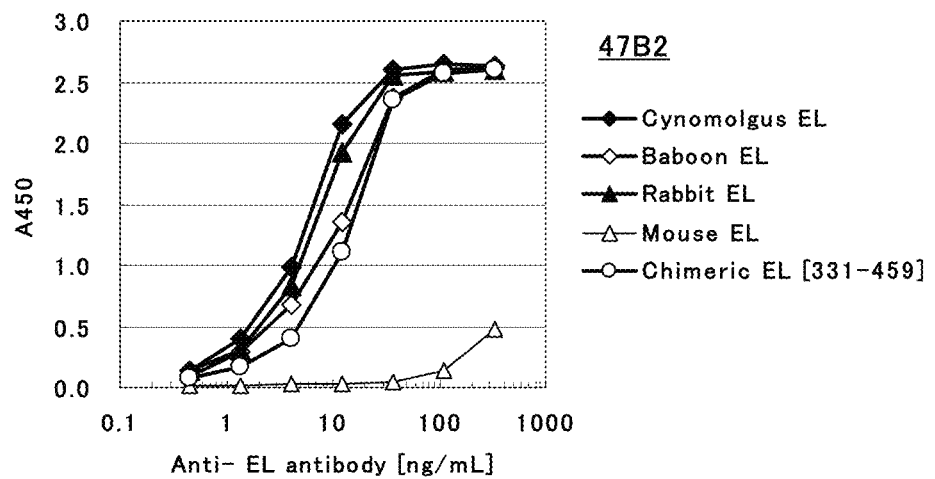
FIG. 9B shows results of measurements of the binding activity of 47B2 antibody against cynomolgus EL, baboon EL, rabbit EL, mouse EL and human-mouse chimera EL. It is shown that 47B2 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.
Figure 9C:
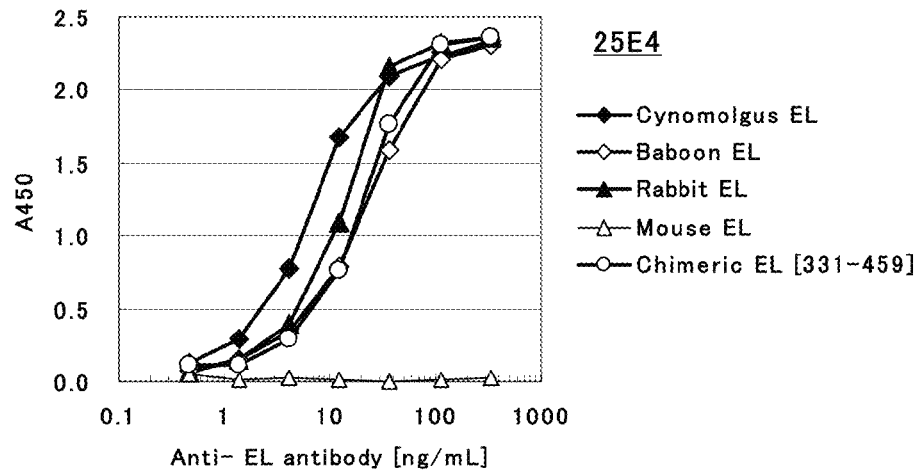
FIG. 9C shows results of measurements of the binding activity of 25E4 antibody against cynomolgus EL, baboon EL, rabbit EL, mouse EL and human-mouse chimera EL. It is shown that 25E4 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.
Figure 9D:
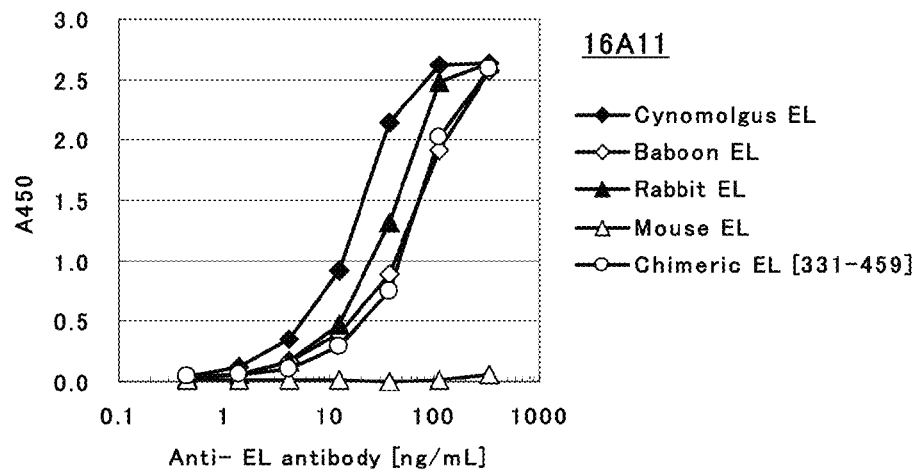
FIG. 9D shows results of measurements of the binding activity of 16A11 antibody against cynomolgus EL, baboon EL, rabbit EL, mouse EL and human-mouse chimera EL. It is shown that 16A11 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.
Figure 9E:
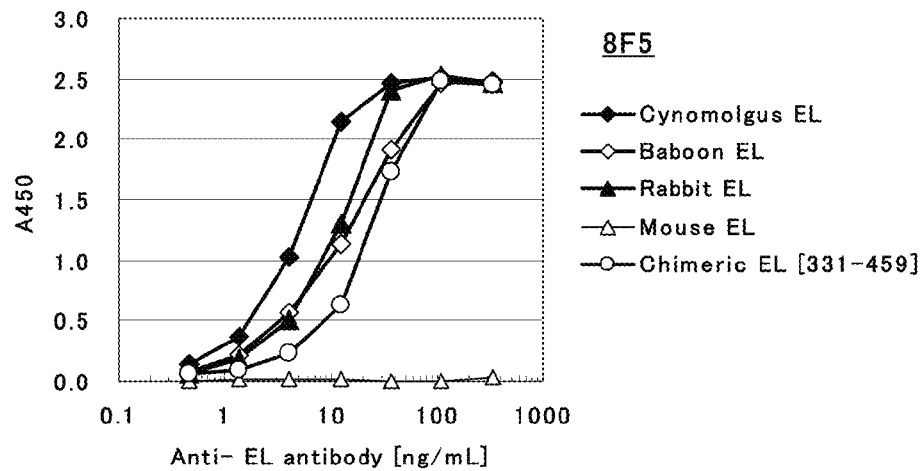
FIG. 9E shows results of measurements of the binding activity of 8F5 antibody against cynomolgus EL, baboon EL, rabbit EL, mouse EL and human-mouse chimera EL. It is shown that 8F5 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.
Figure 9F:
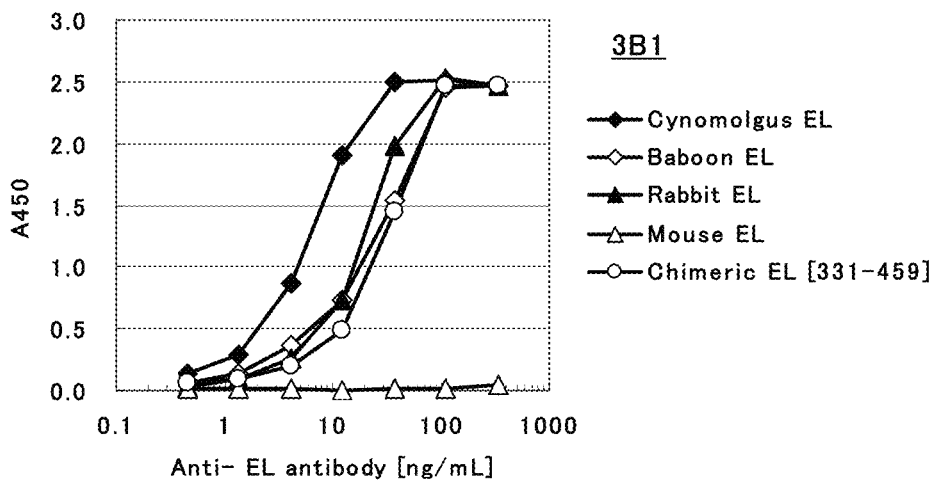
FIG. 9F shows results of measurements of the binding activity of 3B1 antibody against cynomolgus EL, baboon EL, rabbit EL, mouse EL and human-mouse chimera EL. It is shown that 3B1 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.
Figure 9G:
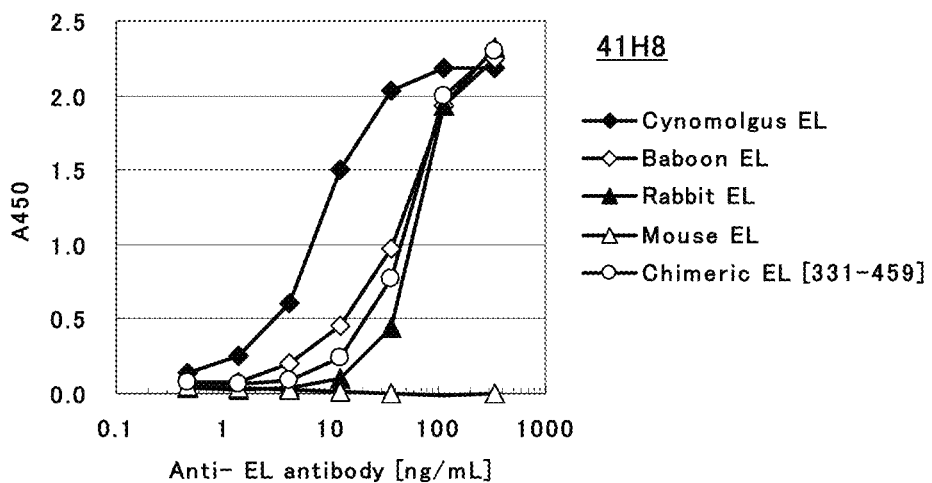
FIG. 9G shows results of measurements of the binding activity of 41H8 antibody against cynomolgus EL, baboon EL, rabbit EL, mouse EL and human-mouse chimera EL. It is shown that 41H8 antibody binds cynomolgus EL, baboon EL, rabbit EL, mouse EL and human-mouse chimera EL. Vertical axis of the graph shows absorbance, and horizontal axis of the graph shows concentration (ng/mL) of antibody.

Rabbit HL and Rabbit LPL enzyme solution was prepared by using the same method. Enzyme activity in the case of adding no anti-EL antibody was determined as control value and the specific activity was calculated against the control value at each concentration of the antibody. For comparison, the result was described side by side inhibition curve of rabbit EL (FIG. 8H~I).

As a result, it was shown that 8F5 and 47B2 antibodies didn't inhibit neither HL nor LPL enzyme activity.

EXAMPLE 20

The Epitope Mapping of Anti-EL Antibody

The epitope mapping of 47B2, 25E4, 16A11, 8F5, 3B1 and 41H8 antibodies was conducted by the same method as described Example 10.

Because 47B2, 16A11, 8F5 and 3B1 antibodies were shown to bind human EL 411-459 the same as 12B10, we concluded that the epitope of these antibodies was the same epitope as 12B10.

Because 25E4 and 41H8 antibodies were shown not to bind human EL 411-459, but were only shown to bind human EL [331-459]-mouse EL, we concluded that the epitope of these antibodies was 331-459 of EL.

Based on the above results, the present invention was concluded to bind 331-459 region of human EL and this was indicated in FIG. 5B.

In FIG. 5B, the region which monoclonal antibodies relating to the present invention bind was surrounded by the dashed lines. Because the homology of amino acids of this region was not high among human EL, human LPL and human HL, it was supposed that these antibodies showed EL selective inhibition as discussed in example 19.

Anti-EL antibodies obtained by Example were summarized in Table. 1.

TABLE 1

| | | | | Neutralizing activity IC50 [nM] | | | |
|---|---|---|---|---|---|---|---|
| No. | Clone name | subclass | Baboon EL | Human-Mouse chimeric EL | Cynomolgus monkey EL | Rabbit EL | Epitope |
| 1 | 12B10 | IgG2a | 7.1 | 15 | 6.2 | 201 | 411-459 |
| 2 | 47B2 | IgG2a | 4.6 | 5.3 | 4.7 | 37 | 411-459 |
| 3 | 25E4 | IgG2b | 5.7 | 6.9 | 4.2 | 85 | 331-459 |
| 4 | 16A11 | IgG1 | 6.2 | 6.1 | 6.2 | 69 | 411-459 |
| 5 | 8F5 | IgG2a | 4.8 | 13 | 3.0 | 98 | 411-459 |
| 6 | 3B1 | IgG1 | 6.6 | 18 | 6.2 | 207 | 441-459 |
| 7 | 41H8 | IgG1 | 7.2 | 15 | 5.9 | 391 | 331-459 |

EXAMPLE 21

Binding Affinities of Anti-EL Antibodies

The binding affinities of anti-EL antibodies were measured using Biacore. Anti-C2-tag antibody was immobilized on a sensor chip CM5 (GE HealthCare) using amine-coupling and baboon EL heparin extract or cynomolgus monkey heparin extract diluted with HBS-P (GE Healthcare) was added and EL were captured on the sensor chip. Then anti-EL antibodies diluted with HBS-P were added and the binding affinities were calculated by bivalent fitting of BIAevaluation software (FIG. 9A-G). The results of binding affinities of each anti-EL antibodies were summarized in Table 2 and Table 3.

TABLE 2

Binding affinity against cynomolgus monkey EL
Affinity for Cynomolgus monkey EL

| No. | clone name | ka[1/Ms] | kd[1/s] | $K_D$ [nM] |
|---|---|---|---|---|
| 1 | 12B10 | $8.8 \times 10^5$ | $1.8 \times 10^{-4}$ | $2.0 \times 10^{-10}$ |
| 2 | 47B2 | $2.5 \times 10^5$ | $3.3 \times 10^{-4}$ | $1.3 \times 10^{-9}$ |
| 3 | 25E4 | $1.6 \times 10^5$ | $9.4 \times 10^{-5}$ | $5.9 \times 10^{-10}$ |
| 4 | 16A11 | $1.4 \times 10^5$ | $3.9 \times 10^{-4}$ | $2.8 \times 10^{-9}$ |
| 5 | 8F5 | $1.4 \times 10^5$ | $1.4 \times 10^{-4}$ | $1.0 \times 10^{-9}$ |
| 6 | 3B1 | $1.8 \times 10^5$ | $9.9 \times 10^{-5}$ | $5.5 \times 10^{-10}$ |
| 7 | 41H8 | $1.6 \times 10^5$ | $1.0 \times 10^{-4}$ | $6.3 \times 10^{-10}$ |

TABLE 3

Binding affinity against baboon EL
Affinity for Baboon EL

| No. | clone name | ka[1/Ms] | kd[1/s] | $K_D$ [nM] |
|---|---|---|---|---|
| 1 | 12B10 | $3.5 \times 10^5$ | $2.1 \times 10^{-4}$ | $6.0 \times 10^{-10}$ |
| 2 | 47B2 | $1.4 \times 10^5$ | $5.6 \times 10^{-4}$ | $4.0 \times 10^{-9}$ |
| 3 | 25E4 | $2.5 \times 10^5$ | $1.6 \times 10^{-4}$ | $6.4 \times 10^{-10}$ |
| 4 | 16A11 | $1.2 \times 10^5$ | $1.2 \times 10^{-4}$ | $1.0 \times 10^{-9}$ |
| 5 | 8F5 | $1.4 \times 10^5$ | $2.1 \times 10^{-4}$ | $4.0 \times 10^{-9}$ |
| 6 | 3B1 | $9.3 \times 10^4$ | $1.4 \times 10^{-4}$ | $1.5 \times 10^{-9}$ |
| 7 | 41H8 | $1.1 \times 10^5$ | $2.9 \times 10^{-4}$ | $2.6 \times 10^{-9}$ |

EXAMPLE 22

Effect of Anti-EL Antibodies on Plasma HDL-c in Rabbit

Figure 10A:
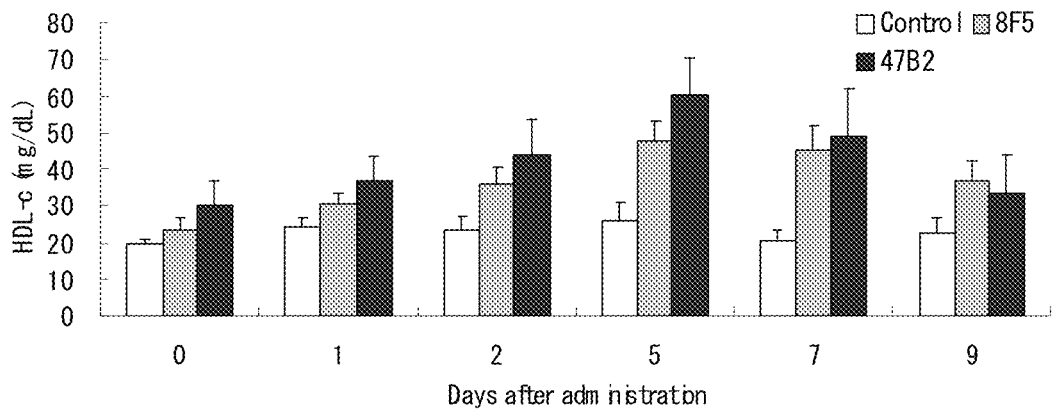
FIG. 10A shows results of measurements of HDL-c blood concentration after we administer to rabbit 47B2 and 8F5 antibody. Vertical axis of the graph shows concentration (ng/mL) of blood HDL-c, and horizontal axis of the graph shows number of days after antibody administration.

47B2 or 8F5 antibody diluted with PBS was administrated to auricular vein at a dose of 10 mg/kg. Three rabbits were administrated with anti-EL antibody and two rabbits were administrated with control antibody. Blood was taken on the Day 1, 2, 5, 7 and 9. HDL-c was measured using a Cholestest N HDL (Sekisui medical). The results were indicated at FIGS. 10A and 10B.

EXAMPLE 23

Analysis of Amino Acid Sequence of Variable Region of Anti-EL Antibodies

The amino acid sequence of variable region of 47B2, 25E4, 16A11, 8F5, 3B1 and 41H8 antibodies were determined using the same method as Example 11.

The amino acid sequence of heavy chain variable region of 47B2 antibody was shown in SEQ ID No: 18, the amino acid sequence of CDR1 of variable region was shown in SEQ ID No: 19, the amino acid sequence of CDR2 of variable region was shown in SEQ ID No: 20 and the amino acid sequence of CDR3 of variable region was shown in SEQ ID No: 21. The amino acid sequence of light chain variable region of 47B2 antibody was shown in SEQ ID No: 22, the amino acid sequence of CDR1 of variable region was shown in SEQ ID No: 23, the amino acid sequence of CDR2 of variable region was shown in SEQ ID No: 24 and the amino acid sequence of CDR3 of variable region was shown in SEQ ID No: 25 (FIG. 6B).

The amino acid sequence of heavy chain variable region of 25E4 antibody was shown in SEQ ID No: 26, the amino acid sequence of CDR1 of variable region was shown in SEQ ID No: 27, the amino acid sequence of CDR2 of variable region was shown in SEQ ID No: 28 and the amino acid sequence of CDR3 of variable region was shown in SEQ ID No: 29. The amino acid sequence of light chain variable region of 25E4 antibody was shown in SEQ ID No: 30, the amino acid sequence of CDR1 of variable region was shown in SEQ ID No: 31, the amino acid sequence of CDR2 of variable region was shown in SEQ ID No: 32 and the amino acid sequence of CDR3 of variable region was shown in SEQ ID No: 33 (FIG. 6C).

The amino acid sequence of heavy chain variable region of 16A11 antibody was shown in SEQ ID No: 34, the amino acid sequence of CDR1 of variable region was shown in SEQ ID No: 35, the amino acid sequence of CDR2 of variable region was shown in SEQ ID No: 36 and the amino acid sequence of CDR3 of variable region was shown in SEQ ID No: 37. The amino acid sequence of light chain variable region of 16A11 antibody was shown in SEQ ID No: 38, the amino acid sequence of CDR1 of variable region was shown in SEQ ID No: 39, the amino acid sequence of CDR2 of variable region was shown in SEQ ID No: 40 and the amino acid sequence of CDR3 of variable region was shown in SEQ ID No: 41 (FIG. 6D).

The amino acid sequence of heavy chain variable region of 8F5 antibody was shown in SEQ ID No: 42, the amino acid sequence of CDR1 of variable region was shown in SEQ ID No: 43, the amino acid sequence of CDR2 of variable region was shown in SEQ ID No: 44 and the amino acid sequence of CDR3 of variable region was shown in SEQ ID No: 45. The amino acid sequence of light chain variable region of 8F5 antibody was shown in SEQ ID No: 46, the amino acid sequence of CDR1 of variable region was shown in SEQ ID No: 47, the amino acid sequence of CDR2 of variable region was shown in SEQ ID No: 48 and the amino acid sequence of CDR3 of variable region was shown in SEQ ID No: 49 (FIG. 6E).

The amino acid sequence of heavy chain variable region of 3B1 antibody was shown in SEQ ID No: 50, the amino acid sequence of CDR1 of variable region was shown in SEQ ID No: 51, the amino acid sequence of CDR2 of variable region was shown in SEQ ID No: 52 and the amino acid sequence of CDR3 of variable region was shown in SEQ ID No: 53. The amino acid sequence of light chain variable region of 3B1 antibody was shown in SEQ ID No: 54, the amino acid sequence of CDR1 of variable region was shown in SEQ ID No: 55, the amino acid sequence of CDR2 of variable region was shown in SEQ ID No: 56 and the amino acid sequence of CDR3 of variable region was shown in SEQ ID No: 57 (FIG. 6F).

The amino acid sequence of heavy chain variable region of 41H8 antibody was shown in SEQ ID No: 58, the amino acid sequence of CDR1 of variable region was shown in SEQ ID No: 59, the amino acid sequence of CDR2 of variable region was shown in SEQ ID No: 60 and the amino acid sequence of CDR3 of variable region was shown in SEQ ID No: 61. The amino acid sequence of light chain variable region of 41H8 antibody was shown in SEQ ID No: 62, the amino acid sequence of CDR1 of variable region was shown in SEQ ID No: 63, the amino acid sequence of CDR2 of variable region was shown in SEQ ID No: 64 and the amino acid sequence of CDR3 of variable region was shown in SEQ ID No: 65 (FIG. 6G).

EXAMPLE 24

Alignment of Amino Acids of Variable Region of Antgi-EL Antibodies

The amino acid sequences of variable region of 12B10, 47B2, 25E4, 16A11, 8F5, 3B1 and 41H8 were aligned (FIGS. 11A and 11B).

The analysis of CDRs of heavy and light chain revealed the following things.

The amino acids sequence of heavy chain CDR1 was consisted of 7 amino acids, T (S or Y) (G or N) (M or V) GVG.

The amino acid sequence of heavy chain CDR2 was consisted of 16 amino acids, HIWW (N or H) (D or E or G) (E or N or Y) (K or Y) YY (K or N or S) (P or T) (A or D or G or S) LKS.

The amino acids sequence of heavy chain CDR3 was consisted of 9 amino acids, (S or M) (A or Y) (D or P) G (S or T) PFPS, or (I or S) (G or S or Y) (A or D or G or P) G (T or V or Y) P (F or L) DY The amino acids sequence of light chain CDR1 was consisted of 11 amino acids, KASQDI (H or N) (K or R or T) (F or Y) I (A or V).

The amino acids sequence of light chain CDR2 was comprised of 7 amino acids, (H or Y) (P or T) (F or S) TLQP.

The amino acids sequence of light chain CDR3 was comprised of 9 amino acids, LQYD (D or I or N or T) L (L or T) WT.

From above-mentioned facts, it was concluded that heavy and light chains of 7 antibodies have a commonality.

Industrial Applicability

The monoclonal antibody of the present invention is useful as a drug for prevention and/or treatment of dyslipidemia, hyperlipidemia, arteriosclerosis, atherosclerosis, hypercholesterolemia, hypertriglyceridemia, diabetes, obesity and/or syndrome X because the monoclonal antibody of the invention has the activity for selectively inhibiting enzyme activity of EL.

Sequence list

The invention claimed is:

1. A monoclonal antibody or a fragment thereof, selected from the group consisting of:
   1) a monoclonal antibody or a fragment thereof, having a heavy chain variable region including three CDRs comprising the amino acid sequence of SEQ ID NO: 7, the amino acid sequence of SEQ ID NO: 8 and the amino acid sequence of SEQ ID NO: 9, and a light chain variable region including three CDRs comprising the amino acid sequence of SEQ ID NO: 11, the amino acid sequence of SEQ ID NO: 12 and the amino acid sequence of SEQ ID NO: 13;
   2) a monoclonal antibody or a fragment thereof, having a heavy chain variable region including three CDRs comprising the amino acid sequence of SEQ ID NO: 19, the amino acid sequence of SEQ ID NO: 20 and the amino acid sequence of SEQ ID NO: 21, and a light chain variable region including three CDRs comprising the amino acid sequence of SEQ ID NO: 23, the amino acid sequence of SEQ ID NO: 24 and the amino acid sequence of SEQ ID NO: 25;

3) a monoclonal antibody or a fragment thereof, having a heavy chain variable region including three CDRs comprising the amino acid sequence of SEQ ID NO: 27, the amino acid sequence of SEQ ID NO: 28 and the amino acid sequence of SEQ ID NO: 29, and a light chain variable region including three CDRs comprising the amino acid sequence of SEQ ID NO: 31, the amino acid sequence of SEQ ID NO: 32 and the amino acid sequence of SEQ ID NO: 33;

4) a monoclonal antibody or a fragment thereof, having a heavy chain variable region including three CDRs comprising the amino acid sequence of SEQ ID NO: 35, the amino acid sequence of SEQ ID NO: 36 and the amino acid sequence of SEQ ID NO: 37, and a light chain variable region including three CDRs comprising the amino acid sequence of SEQ ID NO: 39, the amino acid sequence of SEQ ID NO: 40 and the amino acid sequence of SEQ ID NO: 41;

5) a monoclonal antibody or a fragment thereof, having a heavy chain variable region including three CDRs comprising the amino acid sequence of SEQ ID NO: 43, the amino acid sequence of SEQ ID NO: 44 and the amino acid sequence of SEQ ID NO: 45, and a light chain variable region including three CDRs comprising the amino acid sequence of SEQ ID NO: 47, the amino acid sequence of SEQ ID NO: 48 and the amino acid sequence of SEQ ID NO: 49;

6) a monoclonal antibody or a fragment thereof, having a heavy chain variable region including three CDRs comprising the amino acid sequence of SEQ ID NO: 51, the amino acid sequence of SEQ ID NO: 52 and the amino acid sequence of SEQ ID NO: 53, and a light chain variable region including three CDRs comprising the amino acid sequence of SEQ ID NO: 55, the amino acid sequence of SEQ ID NO: 56 and the amino acid sequence of SEQ ID NO: 57; and 7) a monoclonal antibody or a fragment thereof, having a heavy chain variable region including three CDRs comprising the amino acid sequence of SEQ ID NO: 59, the amino acid sequence of SEQ ID NO: 60 and the amino acid sequence of SEQ ID NO: 61, and a light chain variable region including three CDRs comprising the amino acid sequence of SEQ ID NO: 63, the amino acid sequence of SEQ ID NO: 64 and the amino acid sequence of SEQ ID NO: 65.

2. A monoclonal antibody or a fragment thereof, selected from the group consisting of:

1) a monoclonal antibody or a fragment thereof, having a heavy chain variable region comprising the amino acid sequence of SEQ ID NO: 6, and a light chain variable region comprising the amino acid sequence of SEQ ID NO: 10;

2) a monoclonal antibody or a fragment thereof, having a heavy chain variable region comprising the amino acid sequence of SEQ ID NO: 18, and a light chain variable region comprising amino the acid sequence of SEQ ID NO: 22;

3) a monoclonal antibody or a fragment thereof, having a heavy chain variable region comprising the amino acid sequence of SEQ ID NO: 26, and a light chain variable region comprising the amino acid sequence of SEQ ID NO: 30;

4) a monoclonal antibody or a fragment thereof, having a heavy chain variable region comprising the amino acid sequence of SEQ ID NO: 34, and a light chain variable region comprising the amino acid sequence of SEQ ID NO: 38;

5) a monoclonal antibody or a fragment thereof, having a heavy chain variable region comprising the amino acid sequence of SEQ ID NO: 42, and a light chain variable region comprising the amino acid sequence of SEQ ID NO: 46;

6) a monoclonal antibody or a fragment thereof, having a heavy chain variable region comprising the amino acid sequence of SEQ ID NO: 50, and a light chain variable region comprising the amino acid sequence of SEQ ID NO: 54; and 7) a monoclonal antibody or a fragment thereof, having a heavy chain variable region comprising the amino acid sequence of SEQ ID NO: 58, and a light chain variable region comprising the amino acid sequence of SEQ ID NO: 62.

3. A pharmaceutical composition for treatment of arteriosclerosis comprising the antibody or the fragment thereof according to claim 1, as an active ingredient.

4. A pharmaceutical composition for treatment of arteriosclerosis comprising the antibody or the fragment thereof according to claim 2, as an active ingredient.

5. A method for treatment of arteriosclerosis comprising: administering the antibody or the fragment thereof according to claim 1 in an effective amount.

6. A method for treatment of arteriosclerosis comprising: administering the antibody or the fragment thereof according to claim 2 in an effective amount.

* * * * *

SEQUENCE LISTING

<160> NUMBER OF SEQ ID NOS: 95

<210> SEQ ID NO 1
<211> LENGTH: 500
<212> TYPE: PRT
<213> ORGANISM: Homo sapiens

<400> SEQUENCE: 1

```
Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
            20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
            85                  90                  95

Ile Phe Glu Asn Trp Leu His Lys Leu Val Ser Ala Leu His Thr Arg
            100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
            130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
            165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
            210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
            245                 250                 255

Val Leu Gly Ser Ile Ala Tyr Gly Thr Ile Thr Glu Val Val Lys Cys
            260                 265                 270

Glu His Glu Arg Ala Val His Leu Phe Val Asp Ser Leu Val Asn Gln
            275                 280                 285

Asp Lys Pro Ser Phe Ala Phe Gln Cys Thr Asp Ser Asn Arg Phe Lys
            290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
            325                 330                 335

Lys Thr Arg Ala Gly Met Pro Phe Arg Val Tyr His Tyr Gln Met Lys
            340                 345                 350

Ile His Val Phe Ser Tyr Lys Asn Met Gly Glu Ile Glu Pro Thr Phe
```

```
            355                 360                 365
Tyr Val Thr Leu Tyr Gly Thr Asn Ala Asp Ser Gln Thr Leu Pro Leu
        370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
        435                 440                 445

Ile Arg Val Lys Ser Gly Glu Thr Gln Arg Lys Leu Thr Phe Cys Thr
    450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro
            500

<210> SEQ ID NO 2
<211> LENGTH: 500
<212> TYPE: PRT
<213> ORGANISM: Oryctolagus cuniculus

<400> SEQUENCE: 2

Met Arg Arg Ser Ile Pro Leu Leu Cys Leu Trp Ser Ala Cys Tyr Cys
1               5                   10                  15

Leu Ala Ala Gly Ser Pro Ala Ala Leu Gly Ala Glu Glu Gln Leu Glu
            20                  25                  30

Gly Gly Leu Arg Thr Ala Lys Asp Gly Pro Ala Ala Ala Lys Ala Ala
        35                  40                  45

Val Arg Phe His Leu Arg Thr Ser Lys Gly Pro Glu Arg Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Met Leu Glu Asn Trp Leu His Lys Leu Val Ser Ala Leu Gln Met Arg
            100                 105                 110

Glu Lys Asp Ala Asn Val Val Val Asp Trp Leu Pro Leu Ala His
        115                 120                 125

Gln Leu Tyr Thr Asp Ala Val Asn Ser Thr Arg Val Val Gly Leu Ser
    130                 135                 140

Val Ala Lys Met Leu Asp Trp Leu Gln Gly Lys Asp Gly Phe Ser Leu
145                 150                 155                 160

Gly Asn Val His Leu Ile Gly Tyr Ser Leu Gly Ala His Val Ala Gly
                165                 170                 175

Phe Ala Gly Asn Phe Val Lys Gly Thr Val Gly Arg Ile Thr Gly Leu
            180                 185                 190

Asp Pro Ala Gly Pro Met Phe Glu Gly Val Asp Ile His Arg Arg Leu
        195                 200                 205

Ser Pro Asp Asp Ala Asp Phe Val Asp Val Leu His Thr Tyr Thr Arg
    210                 215                 220
```

```
Ser Phe Gly Ile Ser Gly Ile Gln Met Pro Val Gly His Ile Asp
225                 230                 235                 240

Ile Tyr Pro Asn Gly Asp Phe Gln Pro Gly Cys Gly Leu Asn Asp
            245                 250                 255

Val Leu Gly Ser Ile Ala Tyr Gly Thr Ile Ala Glu Val Lys Cys
        260                 265                 270

Glu His Glu Arg Ala Val His Leu Phe Val Asp Ser Leu Val Asn Gln
    275                 280                 285

Asp Lys Pro Ser Phe Ala Phe Gln Cys Thr Asp Ser Asn Arg Phe Lys
290                 295                 300

Lys Gly Ile Cys Leu Ser Cys Arg Lys Asn Arg Cys Asn Gly Ile Gly
305                 310                 315                 320

Tyr Asn Ala Lys Lys Thr Arg Asn Lys Arg Asn Thr Lys Met Tyr Leu
                325                 330                 335

Lys Thr Arg Ala Gly Met Pro Phe Arg Val Tyr His Tyr Gln Met Lys
            340                 345                 350

Ile His Phe Phe Ser Tyr Lys Ser Val Gly Ala Ile Glu Pro Thr Phe
        355                 360                 365

Tyr Val Thr Leu Tyr Gly Thr Asn Ala Glu Ser Gln Val Leu Ser Leu
370                 375                 380

Glu Ile Val Glu Gln Ile Gly Leu Asn Ala Thr Asn Thr Phe Leu Val
385                 390                 395                 400

Tyr Thr Glu Glu Asp Leu Gly Asp Leu Leu Lys Ile Lys Leu Thr Trp
                405                 410                 415

Glu Gly Thr Ser Arg Ser Trp Tyr Asp Leu Trp Arg Glu Phe Arg Ser
            420                 425                 430

Tyr Leu Ser Gln Pro His Arg Pro Glu Arg Glu Leu Ser Ile Arg Arg
        435                 440                 445

Ile Arg Val Lys Ser Gly Glu Thr Gln Arg Arg Leu Thr Phe Cys Val
450                 455                 460

Glu Asp Pro Glu Lys Thr Ser Ile Ala Pro Gly Gln Glu Leu Trp Phe
465                 470                 475                 480

Tyr Lys Cys Arg Asp Gly Trp Arg Met Lys Asn Glu Thr Ser Pro Thr
                485                 490                 495

Val Glu Leu Ser
            500

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Gly Glu Pro Gly Asp Asp Gly Pro Ser Gly Ala Glu Gly Pro Pro Gly
1               5                   10                  15

Pro Gln Gly

<210> SEQ ID NO 4
<211> LENGTH: 121
<212> TYPE: PRT
<213> ORGANISM: Artificial Sequence
<220> FEATURE:
<223> OTHER INFORMATION: Synthetic

<400> SEQUENCE: 4
```

```
Met Gly His His His His His Ser Lys Ile Gln Leu Thr Trp Glu
1               5                   10                  15

Gly Ala Ser Gln Ser Trp Tyr Asn Leu Trp Lys Glu Phe Arg Ser Tyr
                20                  25                  30

Leu Ser Gln Pro Arg Asn Pro Gly Arg Glu Leu Asn Ile Arg Arg Ile
            35                  40                  45

Arg Val Lys Ser Gly Glu Thr Gln Arg Lys Leu Thr Phe Cys Thr Glu
    50                  55                  60

Asp Pro Glu Asn Thr Ser Ile Ser Pro Gly Arg Glu Leu Trp Phe Arg
65                  70                  75                  80

Lys Cys Arg Asp Gly Trp Arg Met Lys Asn Glu Thr Ser Pro Thr Val
                85                  90                  95

Glu Leu Pro Val Asn Asp Gly Glu Pro Gly Asp Asp Gly Pro Ser Gly
            100                 105                 110

Ala Glu Gly Pro Pro Gly Pro Gln Gly
            115                 120
```

<210> SEQ ID NO 5
<211> LENGTH: 80
<212> TYPE: PRT
<213> ORGANISM: Artificial Sequence
<220> FEATURE:
<223> OTHER INFORMATION: Synthetic

<400> SEQUENCE: 5

```
Met Gly His His His His His Ser Lys Ile Gln Leu Thr Trp Glu
1               5                   10                  15

Gly Ala Ser Gln Ser Trp Tyr Asn Leu Trp Lys Glu Phe Arg Ser Tyr
                20                  25                  30

Leu Ser Gln Pro Arg Asn Pro Gly Arg Glu Leu Asn Ile Arg Arg Ile
            35                  40                  45

Arg Val Lys Ser Gly Glu Thr Gln Arg Lys Val Asn Asp Gly Glu Pro
    50                  55                  60

Gly Asp Asp Gly Pro Ser Gly Ala Glu Gly Pro Pro Gly Pro Gln Gly
65                  70                  75                  80
```

<210> SEQ ID NO 6
<211> LENGTH: 119
<212> TYPE: PRT
<213> ORGANISM: Artificial Sequence
<220> FEATURE:
<223> OTHER INFORMATION: Synthetic

<400> SEQUENCE: 6

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asn Asp Glu Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Tyr Asp Gly Ser Pro Phe Pro Ser Trp Gly Gln Gly
            100                 105                 110
```

```
Thr Leu Val Thr Val Ser Ala
        115

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Thr Ser Gly Met Gly Val Gly
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

His Ile Trp Trp Asn Asp Glu Lys Tyr Tyr Asn Pro Ser Leu Lys Ser
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ser Tyr Asp Gly Ser Pro Phe Pro Ser
1               5

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Phe Gln His Lys Pro Gly Lys Gly Pro Arg Leu Leu Met
        35                  40                  45

Ala Tyr Pro Phe Thr Leu Gln Pro Gly Ile Pro Ser Arg Phe Ser Gly
    50                  55                  60

Asn Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Arg Leu Glu Ile Lys
            100                 105

<210> SEQ ID NO 11
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 11

Lys Ala Ser Gln Asp Ile Asn Lys Tyr Ile Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Tyr Pro Phe Thr Leu Gln Pro
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Leu Gln Tyr Asp Asn Leu Leu Trp Thr
1               5

<210> SEQ ID NO 14
<211> LENGTH: 519
<212> TYPE: PRT
<213> ORGANISM: Artificial Sequence
<220> FEATURE:
<223> OTHER INFORMATION: Synthetic

<400> SEQUENCE: 14

Met Ser Asn Ser Val Pro Leu Leu Cys Phe Trp Ser Leu Cys Cys
1               5                   10                  15

Phe Ala Ala Gly Ser Pro Thr Pro Phe Gly Pro Glu Gly Gln Leu Glu
                20                  25                  30

Asp Glu Leu His Lys Pro Lys Ala Ile Gln Thr Glu Val Lys Pro Ser
            35                  40                  45

Val Arg Phe Asn Leu Arg Thr Ser Lys Asp Pro Glu His Glu Gly Cys
        50                  55                  60

Tyr Leu Ser Leu Gly His Ser Gln Pro Leu Glu Asp Cys Gly Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140

Ile Ala Arg Met Leu Asp Trp Leu Gln Glu Lys Asp Asp Phe Ser Leu
145                 150                 155                 160

Glu Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190
```

```
Asp Pro Ala Gly Pro Met Phe Glu Gly Ala Asp Ile His Lys Arg Leu
        195                 200                 205

Ser Pro Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Met Ala Tyr Gly Thr Ile Thr Glu Val Val Lys Cys
            260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
    290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr His Tyr Gln Met Lys
            340                 345                 350

Ile His Val Phe Ser Tyr Lys Asn Met Gly Glu Ile Glu Pro Thr Phe
        355                 360                 365

Tyr Val Thr Leu Tyr Gly Thr Asn Ala Asp Ser Gln Thr Leu Pro Leu
    370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Leu Arg Ser
            420                 425                 430

Tyr Leu Ser Gln Pro His Asn Pro Gly Arg Glu Leu Asn Ile Arg Arg
        435                 440                 445

Ile Arg Val Lys Ser Gly Glu Thr Gln Arg Lys Leu Thr Phe Cys Ala
    450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro Gly Glu Pro Gly Asp Asp Gly Pro Ser Gly Ala Glu
            500                 505                 510

Gly Pro Pro Gly Pro Gln Gly
        515

<210> SEQ ID NO 15
<211> LENGTH: 519
<212> TYPE: PRT
<213> ORGANISM: Artificial Sequence
<220> FEATURE:
<223> OTHER INFORMATION: Synthetic

<400> SEQUENCE: 15

Met Ser Asn Ser Val Pro Leu Leu Cys Phe Trp Ser Leu Cys Cys Cys
1               5                   10                  15

Phe Ala Ala Gly Ser Pro Thr Pro Phe Gly Pro Glu Gly Gln Leu Ala
            20                  25                  30
```

```
Asp Glu Leu His Lys Pro Lys Ala Ile Gln Thr Glu Val Lys Pro Ser
         35                  40                  45

Val Arg Phe Asn Leu Arg Thr Ser Lys Asp Pro Glu His Glu Gly Cys
 50                  55                  60

Tyr Leu Ser Leu Gly His Ser Gln Pro Leu Glu Asp Cys Gly Phe Asn
 65                  70                  75                  80

Met Thr Ala Lys Thr Phe Phe Ile Ile His Gly Trp Thr Met Ser Gly
                 85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
                115                 120                 125

Gln Leu Tyr Thr Asp Ala Val Asn Asn Thr Arg Val Val Gly His Ser
        130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
        195                 200                 205

Ser Pro Asp Asp Ala Asp Phe Val Asp Val Leu His Thr Tyr Thr Arg
        210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Met Ala Tyr Gly Thr Ile Thr Glu Val Val Lys Cys
                260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
        290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr His Tyr Gln Met Lys
                340                 345                 350

Ile His Val Phe Ser Tyr Lys Asn Met Gly Glu Ile Glu Pro Thr Phe
                355                 360                 365

Tyr Val Thr Leu Tyr Gly Thr Asn Ala Asp Ser Gln Thr Leu Pro Leu
        370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Leu Arg Ser
                420                 425                 430

Tyr Leu Ser Gln Pro His Asn Pro Gly Arg Glu Leu Asn Ile Arg Arg
        435                 440                 445
```

```
Ile Arg Val Lys Ser Gly Glu Thr Gln Arg Lys Leu Thr Phe Cys Ala
    450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro Gly Glu Pro Asp Asp Gly Pro Ser Gly Ala Glu
            500                 505                 510

Gly Pro Pro Gly Pro Gln Gly
            515

<210> SEQ ID NO 16
<211> LENGTH: 519
<212> TYPE: PRT
<213> ORGANISM: Artificial Sequence
<220> FEATURE:
<223> OTHER INFORMATION: Synthetic

<400> SEQUENCE: 16

Met Arg Asn Thr Val Phe Leu Leu Gly Phe Trp Ser Val Tyr Cys Tyr
1               5                   10                  15

Phe Pro Ala Gly Ser Ile Thr Thr Leu Arg Pro Gln Gly Ser Leu Arg
            20                  25                  30

Asp Glu His His Lys Pro Thr Gly Val Pro Ala Thr Ala Arg Pro Ser
        35                  40                  45

Val Ala Phe Asn Ile Arg Thr Ser Lys Asp Pro Glu Gln Glu Gly Cys
50                  55                  60

Asn Leu Ser Leu Gly Asp Ser Lys Leu Leu Glu Asn Cys Gly Phe Asn
65                  70                  75                  80

Met Thr Ala Lys Thr Phe Phe Ile Ile His Gly Trp Thr Met Ser Gly
                85                  90                  95

Met Phe Glu Ser Trp Leu His Lys Leu Val Ser Ala Leu Gln Met Arg
            100                 105                 110

Glu Lys Asp Ala Asn Val Val Val Asp Trp Leu Pro Leu Ala His
        115                 120                 125

Gln Leu Tyr Thr Asp Ala Val Asn Asn Thr Arg Val Val Gly Gln Arg
    130                 135                 140

Val Ala Gly Met Leu Asp Trp Leu Gln Glu Lys Glu Glu Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Val Asp Ile Asn Arg Arg Leu
        195                 200                 205

Ser Pro Asp Asp Ala Asp Phe Val Asp Val Leu His Thr Tyr Thr Leu
    210                 215                 220

Ser Phe Gly Leu Ser Ile Gly Ile Arg Met Pro Val Gly His Ile Asp
225                 230                 235                 240

Ile Tyr Pro Asn Gly Gly Asp Phe Gln Pro Gly Cys Gly Phe Asn Asp
                245                 250                 255

Val Ile Gly Ser Phe Ala Tyr Gly Thr Ile Ser Glu Met Val Lys Cys
            260                 265                 270

Glu His Glu Arg Ala Val His Leu Phe Val Asp Ser Leu Val Asn Gln
        275                 280                 285
```

```
Asp Lys Pro Ser Phe Ala Phe Gln Cys Thr Asp Ser Ser Arg Phe Lys
    290                 295                 300

Arg Gly Ile Cys Leu Ser Cys Arg Lys Asn Arg Cys Asn Asn Ile Gly
305                 310                 315                 320

Tyr Asn Ala Lys Lys Met Arg Lys Lys Arg Asn Ser Lys Met Tyr Leu
                325                 330                 335

Lys Thr Arg Ala Gly Met Pro Phe Lys Val Tyr His Tyr Gln Leu Lys
                340                 345                 350

Val His Met Phe Ser Tyr Asn Ser Gly Asp Thr Gln Pro Thr Leu
                355                 360                 365

Tyr Ile Thr Leu Tyr Gly Ser Asn Ala Asp Ser Gln Asn Leu Pro Leu
            370                 375                 380

Glu Ile Val Glu Lys Ile Glu Leu Asn Ala Thr Asn Thr Phe Leu Val
385                 390                 395                 400

Tyr Thr Glu Glu Asp Leu Gly Asp Leu Leu Lys Met Arg Leu Thr Trp
                405                 410                 415

Glu Gly Val Ala His Ser Trp Tyr Asn Leu Trp Asn Glu Phe Arg Asn
                420                 425                 430

Tyr Leu Ser Gln Pro Ser Asn Pro Ser Arg Glu Leu Tyr Ile Arg Arg
            435                 440                 445

Ile Arg Val Lys Ser Gly Glu Thr Gln Arg Lys Val Thr Phe Cys Thr
        450                 455                 460

Gln Asp Pro Thr Lys Ser Ser Ile Ser Pro Gly Gln Glu Leu Trp Phe
465                 470                 475                 480

His Lys Cys Gln Asp Gly Trp Lys Met Lys Asn Lys Thr Ser Pro Phe
                485                 490                 495

Val Asn Leu Ala Gly Glu Pro Gly Asp Asp Gly Pro Ser Gly Ala Glu
                500                 505                 510

Gly Pro Pro Gly Pro Gln Gly
            515

<210> SEQ ID NO 17
<211> LENGTH: 519
<212> TYPE: PRT
<213> ORGANISM: Artificial Sequence
<220> FEATURE:
<223> OTHER INFORMATION: Synthetic

<400> SEQUENCE: 17

Met Arg Asn Thr Val Phe Leu Leu Gly Phe Trp Ser Val Tyr Cys Tyr
1               5                   10                  15

Phe Pro Ala Gly Ser Ile Thr Thr Leu Arg Pro Gln Gly Ser Leu Arg
                20                  25                  30

Asp Glu His His Lys Pro Thr Gly Val Pro Ala Thr Ala Arg Pro Ser
            35                  40                  45

Val Ala Phe Asn Ile Arg Thr Ser Lys Asp Pro Glu Gln Glu Gly Cys
        50                  55                  60

Asn Leu Ser Leu Gly Asp Ser Lys Leu Leu Glu Asn Cys Gly Phe Asn
65                  70                  75                  80

Met Thr Ala Lys Thr Phe Phe Ile Ile His Gly Trp Thr Met Ser Gly
                85                  90                  95

Met Phe Glu Ser Trp Leu His Lys Leu Val Ser Ala Leu Gln Met Arg
                100                 105                 110

Glu Lys Asp Ala Asn Val Val Val Val Asp Trp Leu Pro Leu Ala His
            115                 120                 125
```

```
Gln Leu Tyr Thr Asp Ala Val Asn Asn Thr Arg Val Val Gly Gln Arg
    130                 135                 140

Val Ala Gly Met Leu Asp Trp Leu Gln Glu Lys Glu Glu Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Val Asp Ile Asn Arg Arg Leu
            195                 200                 205

Ser Pro Asp Asp Ala Asp Phe Val Asp Val Leu His Thr Tyr Thr Leu
    210                 215                 220

Ser Phe Gly Leu Ser Ile Gly Ile Arg Met Pro Val Gly His Ile Asp
225                 230                 235                 240

Ile Tyr Pro Asn Gly Gly Asp Phe Gln Pro Gly Cys Gly Phe Asn Asp
                245                 250                 255

Val Ile Gly Ser Phe Ala Tyr Gly Thr Ile Ser Glu Met Val Lys Cys
                260                 265                 270

Glu His Glu Arg Ala Val His Leu Phe Val Asp Ser Leu Val Asn Gln
            275                 280                 285

Asp Lys Pro Ser Phe Ala Phe Gln Cys Thr Asp Ser Ser Arg Phe Lys
    290                 295                 300

Arg Gly Ile Cys Leu Ser Cys Arg Lys Asn Arg Cys Asn Asn Ile Gly
305                 310                 315                 320

Tyr Asn Ala Lys Lys Met Arg Lys Lys Arg Asn Ser Lys Met Tyr Leu
                325                 330                 335

Lys Thr Arg Ala Gly Met Pro Phe Arg Val Tyr His Tyr Gln Met Lys
            340                 345                 350

Ile His Val Phe Ser Tyr Lys Asn Met Gly Glu Ile Glu Pro Thr Phe
    355                 360                 365

Tyr Val Thr Leu Tyr Gly Thr Asn Ala Asp Ser Gln Thr Leu Pro Leu
370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
    435                 440                 445

Ile Arg Val Lys Ser Gly Glu Thr Gln Arg Lys Val Thr Phe Cys Thr
450                 455                 460

Gln Asp Pro Thr Lys Ser Ser Ile Ser Pro Gly Gln Glu Leu Trp Phe
465                 470                 475                 480

His Lys Cys Gln Asp Gly Trp Lys Met Lys Asn Lys Thr Ser Pro Phe
                485                 490                 495

Val Asn Leu Ala Gly Glu Pro Gly Asp Asp Gly Pro Ser Gly Ala Glu
            500                 505                 510

Gly Pro Pro Gly Pro Gln Gly
            515

<210> SEQ ID NO 18
<211> LENGTH: 119
<212> TYPE: PRT
```

<213> ORGANISM: Artificial Sequence
<220> FEATURE:
<223> OTHER INFORMATION: Synthetic

<400> SEQUENCE: 18

```
Gln Val Ala Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Ser Thr Ser
            20                  25                  30
Gly Met Gly Val Gly Trp Ile Arg Gln Pro Ser Gly Lys Gly Leu Glu
        35                  40                  45
Trp Leu Ala His Ile Trp Trp His Gly Asn Lys Tyr Tyr Ser Thr Gly
    50                  55                  60
Leu Lys Ser Arg Leu Thr Ile Ser Lys Asp Thr Ser Asn Asn Gln Val
65                  70                  75                  80
Phe Leu Lys Ile Ala Ser Val Asp Thr Ala Asp Ala Thr Tyr Tyr
                85                  90                  95
Cys Ala Arg Ile Ser Ala Gly Tyr Pro Leu Asp Tyr Trp Gly Gln Gly
            100                 105                 110
Thr Ser Val Thr Val Ser Ser
        115
```

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

```
Thr Ser Gly Met Gly Val Gly
1               5
```

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

```
His Ile Trp Trp His Gly Asn Lys Tyr Tyr Ser Thr Gly Leu Lys Ser
1               5                   10                  15
```

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

```
Ile Ser Ala Gly Tyr Pro Leu Asp Tyr
1               5
```

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln His Lys Pro Gly Lys Gly Pro Arg Leu Leu Ile
        35                  40                  45

His Tyr Thr Ser Thr Leu Gln Pro Gly Phe Pro Ser Arg Phe Ser Gly
    50                  55                  60

Ser Gly Ser Gly Arg Asp Tyr Ser Leu Ser Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105
```

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

```
Lys Ala Ser Gln Asp Ile Asn Lys Tyr Ile Val
1               5                   10
```

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

```
Tyr Thr Ser Thr Leu Gln Pro
1               5
```

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

```
Leu Gln Tyr Asp Asn Leu Leu Trp Thr
1               5
```

<210> SEQ ID NO 26
<211> LENGTH: 119
<212> TYPE: PRT
<213> ORGANISM: Artificial Sequence
<220> FEATURE:
<223> OTHER INFORMATION: Synthetic

<400> SEQUENCE: 26

```
Gln Val Ala Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45
```

```
Trp Leu Ala His Ile Trp Trp His Gly Asn Lys Tyr Tyr Ser Thr Ala
 50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Ala Asp Thr Ala Thr Tyr Tyr
                 85                  90                  95

Cys Ala Arg Ile Ser Asp Gly Tyr Pro Leu Asp Tyr Trp Gly Gln Gly
             100                 105                 110

Thr Ser Val Thr Val Ser Ser
            115

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Thr Ser Gly Met Gly Val Gly
 1               5

<210> SEQ ID NO 28
<211> LENGTH: 16
<212> TYPE: PRT
<213> ORGANISM: Artificial Sequence
<220> FEATURE:
<223> OTHER INFORMATION: Synthetic

<400> SEQUENCE: 28

His Ile Trp Trp His Gly Asn Lys Tyr Tyr Ser Thr Ala Leu Lys Ser
 1               5                  10                  15

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Ile Ser Asp Gly Tyr Pro Leu Asp Tyr
 1               5

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
                 20                  25                  30

Ile Val Trp Tyr Gln Gln Lys Pro Gly Lys Gly Pro Arg Leu Leu Ile
             35                  40                  45

His Tyr Thr Ser Thr Leu Gln Pro Gly Phe Pro Ser Arg Phe Ser Gly
         50                  55                  60

Ser Gly Ser Gly Arg Asp Tyr Ser Leu Ser Ile Thr Asn Leu Glu Pro
 65                  70                  75                  80
```

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Lys Ala Ser Gln Asp Ile Asn Lys Tyr Ile Val
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Tyr Thr Ser Thr Leu Gln Pro
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Leu Gln Tyr Asp Asn Leu Leu Trp Thr
1               5

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Val Arg Gln Pro Ser Gly Lys Gly Leu Glu
        35                  40                  45

Trp Leu Ala His Ile Trp Trp Asn Asp Tyr Tyr Tyr Lys Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Val Asp Thr Ala Thr Tyr Tyr
                85                  90                  95

Cys Ala Arg Met Ala Pro Gly Thr Pro Phe Pro Ser Trp Gly Gln Gly
            100                 105                 110

Thr Leu Val Thr Val Ser Ala
        115

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Thr Ser Gly Met Gly Val Gly
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

His Ile Trp Trp Asn Asp Tyr Tyr Tyr Lys Thr Ala Leu Lys Ser
1               5                   10                  15

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Met Ala Pro Gly Thr Pro Phe Pro Ser
1               5

<210> SEQ ID NO 38
<211> LENGTH: 107
<212> TYPE: PRT
<213> ORGANISM: Artificial Sequence
<220> FEATURE:
<223> OTHER INFORMATION: Synthetic

<400> SEQUENCE: 38

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Ile Leu Leu Trp
                85                  90                  95

Thr Phe Gly Gly Gly Thr Lys Leu Glu Ile Lys
            100                 105

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Lys Ala Ser Gln Asp Ile Asn Arg Tyr Ile Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Tyr Thr Ser Thr Leu Gln Pro
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Leu Gln Tyr Asp Ile Leu Leu Trp Thr
1               5

<210> SEQ ID NO 42
<211> LENGTH: 119
<212> TYPE: PRT
<213> ORGANISM: Artificial Sequence
<220> FEATURE:
<223> OTHER INFORMATION: Synthetic

<400> SEQUENCE: 42

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Asn Met Gly Val Gly Trp Ile Arg Gln Pro Ser Gly Lys Gly Leu Glu
            35                  40                  45

Trp Leu Ala His Ile Trp Trp Asn Asp Tyr Lys Tyr Tyr Asn Thr Ala
        50                  55                  60

Leu Lys Ser Arg Leu Thr Ile Ser Lys Asp Thr Ser Asn Asn Gln Val
65                  70                  75                  80

Phe Leu Lys Ile Ala Ser Leu Asp Thr Ala Asp Thr Ala Thr Tyr Tyr
                85                  90                  95

Cys Ala Arg Ile Gly Gly Gly Thr Pro Leu Asp Tyr Trp Gly Gln Gly
            100                 105                 110

Thr Ser Leu Thr Val Ser Ser
        115

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Thr Ser Asn Met Gly Val Gly
1               5

<210> SEQ ID NO 44

```
<211> LENGTH: 16
<212> TYPE: PRT
<213> ORGANISM: Artificial Sequence
<220> FEATURE:
<223> OTHER INFORMATION: Synthetic

<400> SEQUENCE: 44

His Ile Trp Trp Asn Asp Tyr Lys Tyr Tyr Asn Thr Ala Leu Lys Ser
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Ile Gly Gly Gly Thr Pro Leu Asp Tyr
1               5

<210> SEQ ID NO 46
<211> LENGTH: 107
<212> TYPE: PRT
<213> ORGANISM: Artificial Sequence
<220> FEATURE:
<223> OTHER INFORMATION: Synthetic

<400> SEQUENCE: 46

Asp Ile Gln Met Ala Gln Ser Pro Ser Ser Leu Ser Ala Ser Leu Gly
1               5                   10                  15

Gly Lys Val Thr Ile Thr Cys Lys Ala Ser Gln Asp Ile His Thr Tyr
            20                  25                  30

Ile Ala Trp Tyr Gln His Lys Pro Gly Lys Pro Arg Leu Leu Met
        35                  40                  45

Leu Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asp Leu Leu Trp
                85                  90                  95

Thr Phe Gly Gly Gly Thr Lys Leu Glu Ile Lys
            100                 105

<210> SEQ ID NO 47
<211> LENGTH: 11
<212> TYPE: PRT
<213> ORGANISM: Artificial Sequence
<220> FEATURE:
<223> OTHER INFORMATION: Synthetic

<400> SEQUENCE: 47

Lys Ala Ser Gln Asp Ile His Thr Tyr Ile Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Tyr Thr Ser Thr Leu Gln Pro
```

```
<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Leu Gln Tyr Asp Asp Leu Leu Trp Thr
1               5

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Val Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Phe
                85                  90                  95

Cys Ala Arg Ser Tyr Asp Gly Tyr Pro Phe Asp Tyr Trp Gly Gln Gly
            100                 105                 110

Thr Leu Val Thr Val Ser Ala
        115

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Thr Ser Gly Val Gly Val Gly
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic

<400> SEQUENCE: 52

His Ile Trp Trp Asn Asp Asn Lys Tyr Tyr Asn Thr Ala Leu Lys Ser
1               5                   10                  15

<210> SEQ ID NO 53
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 53

Ser Tyr Asp Gly Tyr Pro Phe Asp Tyr
1               5

<210> SEQ ID NO 54
<211> LENGTH: 107
<212> TYPE: PRT
<213> ORGANISM: Artificial Sequence
<220> FEATURE:
<223> OTHER INFORMATION: Synthetic

<400> SEQUENCE: 54

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln His Lys Pro Gly Lys Pro Arg Leu Leu Ile
        35                  40                  45

His His Thr Ser Thr Leu Gln Pro Gly Ile Pro Ser Arg Phe Ser Glu
    50                  55                  60

Ser Gly Ser Gly Arg Asp Tyr Ser Phe Ser Ile Ser Asn Leu Glu Pro
65                  70                  75                  80

Glu Asp Ile Ala Ser Tyr Tyr Cys Leu Gln Tyr Asp Thr Leu Leu Trp
                85                  90                  95

Thr Phe Gly Gly Gly Thr Lys Leu Glu Ile Arg
            100                 105

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

Lys Ala Ser Gln Asp Ile Asn Lys Tyr Ile Val
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

His Thr Ser Thr Leu Gln Pro
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Leu Gln Tyr Asp Thr Leu Leu Trp Thr
1               5
```

```
<210> SEQ ID NO 58
<211> LENGTH: 119
<212> TYPE: PRT
<213> ORGANISM: Artificial Sequence
<220> FEATURE:
<223> OTHER INFORMATION: Synthetic

<400> SEQUENCE: 58

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala His Ile Trp Trp Asn Glu Asn Lys Tyr Tyr Asn Thr Asp
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Gly Pro Gly Val Pro Phe Asp Tyr Trp Gly Gln Gly
            100                 105                 110

Thr Thr Ile Thr Val Ser Ser
        115

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59

Thr Tyr Gly Met Gly Val Gly
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

His Ile Trp Trp Asn Glu Asn Lys Tyr Tyr Asn Thr Asp Leu Lys Ser
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Ile Gly Pro Gly Val Pro Phe Asp Tyr
1               5

<210> SEQ ID NO 62
<211> LENGTH: 107
<212> TYPE: PRT
<213> ORGANISM: Artificial Sequence
<220> FEATURE:
```

<223> OTHER INFORMATION: Synthetic

<400> SEQUENCE: 62

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Asn Gly
    50                  55                  60

Ser Gly Ser Gly Arg Asp Tyr Ser Phe Thr Ile Ser Asn Leu Glu Pro
65                  70                  75                  80

Glu Asp Ile Ala Thr Tyr Tyr Cys Leu Gln Tyr Asp Ile Leu Thr Trp
                85                  90                  95

Thr Phe Gly Gly Gly Thr Lys Leu Glu Ile Lys
            100                 105

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Lys Ala Ser Gln Asp Ile Asn Lys Phe Ile Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Tyr Thr Ser Thr Leu Gln Pro
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Leu Gln Tyr Asp Ile Leu Thr Trp Thr
1               5

<210> SEQ ID NO 66
<211> LENGTH: 475
<212> TYPE: PRT
<213> ORGANISM: Homo sapiens

<400> SEQUENCE: 66

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp

```
              35                  40                  45
Thr Ala Glu Asp Thr Cys His Leu Ile Pro Gly Val Ala Glu Ser Val
 50                  55                  60

Ala Thr Cys His Phe Asn His Ser Ser Lys Thr Phe Met Val Ile His
 65                  70                  75                  80

Gly Trp Thr Val Thr Gly Met Tyr Glu Ser Trp Val Pro Lys Leu Val
                     85                  90                  95

Ala Ala Leu Tyr Lys Arg Glu Pro Asp Ser Asn Val Ile Val Val Asp
                    100                 105                 110

Trp Leu Ser Arg Ala Gln Glu His Tyr Pro Val Ser Ala Gly Tyr Thr
                    115                 120                 125

Lys Leu Val Gly Gln Asp Val Ala Arg Phe Ile Asn Trp Met Glu Glu
130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                    165                 170                 175

Asn Arg Ile Thr Gly Leu Asp Pro Ala Gly Pro Asn Phe Glu Tyr Ala
                    180                 185                 190

Glu Ala Pro Ser Arg Leu Ser Pro Asp Asp Ala Asp Phe Val Asp Val
                    195                 200                 205

Leu His Thr Phe Thr Arg Gly Ser Pro Gly Arg Ser Ile Gly Ile Gln
                    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                    245                 250                 255

Leu Gly Asp Val Asp Gln Leu Val Lys Cys Ser His Glu Arg Ser Ile
                    260                 265                 270

His Leu Phe Ile Asp Ser Leu Leu Asn Glu Glu Asn Pro Ser Lys Ala
                    275                 280                 285

Tyr Arg Cys Ser Ser Lys Glu Ala Phe Glu Lys Gly Leu Cys Leu Ser
                    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                    325                 330                 335

Pro Tyr Lys Val Phe His Tyr Gln Val Lys Ile His Phe Ser Gly Thr
                    340                 345                 350

Glu Ser Glu Thr His Thr Asn Gln Ala Phe Glu Ile Ser Leu Tyr Gly
                    355                 360                 365

Thr Val Ala Glu Ser Glu Asn Ile Pro Phe Thr Leu Pro Glu Val Ser
                    370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                    405                 410                 415

Trp Ser Asp Trp Trp Ser Ser Pro Gly Phe Ala Ile Gln Lys Ile Arg
                    420                 425                 430

Val Lys Ala Gly Glu Thr Gln Lys Lys Val Ile Phe Cys Ser Arg Glu
                    435                 440                 445

Lys Val Ser His Leu Gln Lys Gly Lys Ala Pro Ala Val Phe Val Lys
                    450                 455                 460
```

```
Cys His Asp Lys Ser Leu Asn Lys Lys Ser Gly
465                 470                 475

<210> SEQ ID NO 67
<211> LENGTH: 499
<212> TYPE: PRT
<213> ORGANISM: Homo sapiens

<400> SEQUENCE: 67

Met Asp Thr Ser Pro Leu Cys Phe Ser Ile Leu Leu Val Leu Cys Ile
1               5                   10                  15

Phe Ile Gln Ser Ser Ala Leu Gly Gln Ser Leu Lys Pro Glu Pro Phe
                20                  25                  30

Gly Arg Arg Ala Gln Ala Val Glu Thr Asn Lys Thr Leu His Glu Met
            35                  40                  45

Lys Thr Arg Phe Leu Leu Phe Gly Glu Thr Asn Gln Gly Cys Gln Ile
        50                  55                  60

Arg Ile Asn His Pro Asp Thr Leu Gln Glu Cys Gly Phe Asn Ser Ser
65                  70                  75                  80

Leu Pro Leu Val Met Ile Ile His Gly Trp Ser Val Asp Gly Val Leu
                85                  90                  95

Glu Asn Trp Ile Trp Gln Met Val Ala Ala Leu Lys Ser Gln Pro Ala
                100                 105                 110

Gln Pro Val Asn Val Gly Leu Val Asp Trp Ile Thr Leu Ala His Asp
            115                 120                 125

His Tyr Thr Ile Ala Val Arg Asn Thr Arg Leu Val Gly Lys Glu Val
        130                 135                 140

Ala Ala Leu Leu Arg Trp Leu Glu Glu Ser Val Gln Leu Ser Arg Ser
145                 150                 155                 160

His Val His Leu Ile Gly Tyr Ser Leu Gly Ala His Val Ser Gly Phe
                165                 170                 175

Ala Gly Ser Ser Ile Gly Gly Thr His Lys Ile Gly Arg Ile Thr Gly
                180                 185                 190

Leu Asp Ala Ala Gly Pro Leu Phe Glu Gly Ser Ala Pro Ser Asn Arg
            195                 200                 205

Leu Ser Pro Asp Asp Ala Asn Phe Val Asp Ala Ile His Thr Phe Thr
        210                 215                 220

Arg Glu His Met Gly Leu Ser Val Gly Ile Lys Gln Pro Ile Gly His
225                 230                 235                 240

Tyr Asp Phe Tyr Pro Asn Gly Gly Ser Phe Gln Pro Gly Cys His Phe
                245                 250                 255

Leu Glu Leu Tyr Arg His Ile Ala Gln His Gly Phe Asn Ala Ile Thr
                260                 265                 270

Gln Thr Ile Lys Cys Ser His Glu Arg Ser Val His Leu Phe Ile Asp
            275                 280                 285

Ser Leu Leu His Ala Gly Thr Gln Ser Met Ala Tyr Pro Cys Gly Asp
        290                 295                 300

Met Asn Ser Phe Ser Gln Gly Leu Cys Leu Ser Cys Lys Lys Gly Arg
305                 310                 315                 320

Cys Asn Thr Leu Gly Tyr His Val Arg Gln Glu Pro Arg Ser Lys Ser
                325                 330                 335

Lys Arg Leu Phe Leu Val Thr Arg Ala Gln Ser Pro Phe Lys Val Tyr
                340                 345                 350

His Tyr Gln Phe Lys Ile Gln Phe Ile Asn Gln Thr Glu Thr Pro Ile
```

```
                355                 360                 365
Gln Thr Thr Phe Thr Met Ser Leu Leu Gly Thr Lys Glu Lys Met Gln
        370                 375                 380

Lys Ile Pro Ile Thr Leu Gly Lys Gly Ile Ala Ser Asn Lys Thr Tyr
385                 390                 395                 400

Ser Phe Leu Ile Thr Leu Asp Val Asp Ile Gly Glu Leu Ile Met Ile
                405                 410                 415

Lys Phe Lys Trp Glu Asn Ser Ala Val Trp Ala Asn Val Trp Asp Thr
                420                 425                 430

Val Gln Thr Ile Ile Pro Trp Ser Thr Gly Pro Arg His Ser Gly Leu
            435                 440                 445

Val Leu Lys Thr Ile Arg Val Lys Ala Gly Glu Thr Gln Gln Arg Met
        450                 455                 460

Thr Phe Cys Ser Glu Asn Thr Asp Asp Leu Leu Leu Arg Pro Thr Gln
465                 470                 475                 480

Glu Lys Ile Phe Val Lys Cys Glu Ile Lys Ser Lys Thr Ser Lys Arg
                485                 490                 495

Lys Ile Arg

<210> SEQ ID NO 68
<211> LENGTH: 119
<212> TYPE: PRT
<213> ORGANISM: Artificial Sequence
<220> FEATURE:
<223> OTHER INFORMATION: Synthetic

<400> SEQUENCE: 68

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asn Asp Glu Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Tyr Asp Gly Ser Pro Phe Pro Ser Trp Gly Gln Gly
            100                 105                 110

Thr Leu Val Thr Val Ser Ala
        115

<210> SEQ ID NO 69
<211> LENGTH: 107
<212> TYPE: PRT
<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Phe Gln His Lys Pro Gly Lys Gly Pro Arg Leu Leu Met
```

```
                35                  40                  45
Ala Tyr Pro Phe Thr Leu Gln Pro Gly Ile Pro Ser Arg Phe Ser Gly
 50                  55                  60

Asn Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Leu Trp
                 85                  90                  95

Thr Phe Gly Gly Gly Thr Arg Leu Glu Ile Lys
                100                 105

<210> SEQ ID NO 70
<211> LENGTH: 119
<212> TYPE: PRT
<213> ORGANISM: Artificial Sequence
<220> FEATURE:
<223> OTHER INFORMATION: Synthetic

<400> SEQUENCE: 70

Gln Val Ala Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp His Gly Asn Lys Tyr Tyr Ser Thr Gly
 50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Ala Asp Thr Ala Thr Tyr Tyr
                 85                  90                  95

Cys Ala Arg Ile Ser Ala Gly Tyr Pro Leu Asp Tyr Trp Gly Gln Gly
                100                 105                 110

Thr Ser Val Thr Val Ser Ser
            115

<210> SEQ ID NO 71
<211> LENGTH: 107
<212> TYPE: PRT
<213> ORGANISM: Artificial Sequence
<220> FEATURE:
<223> OTHER INFORMATION: Synthetic

<400> SEQUENCE: 71

Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
                20                  25                  30

Ile Val Trp Tyr Gln His Lys Pro Gly Lys Gly Pro Arg Leu Leu Ile
            35                  40                  45

His Tyr Thr Ser Thr Leu Gln Pro Gly Phe Pro Ser Arg Phe Ser Gly
 50                  55                  60

Ser Gly Ser Gly Arg Asp Tyr Ser Leu Ser Ile Thr Asn Leu Glu Pro
 65                  70                  75                  80

Glu Asp Ile Ala Thr Tyr Tyr Cys Leu Gln Tyr Asp Asn Leu Leu Trp
                 85                  90                  95

Thr Phe Gly Gly Gly Thr Lys Leu Glu Ile Lys
                100                 105
```

<210> SEQ ID NO 72
<211> LENGTH: 119
<212> TYPE: PRT
<213> ORGANISM: Artificial Sequence
<220> FEATURE:
<223> OTHER INFORMATION: Synthetic

<400> SEQUENCE: 72

```
Gln Val Ala Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp His Gly Asn Lys Tyr Tyr Ser Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Asp Gly Tyr Pro Leu Asp Tyr Trp Gly Gln Gly
            100                 105                 110

Thr Ser Val Thr Val Ser Ser
        115
```

<210> SEQ ID NO 73
<211> LENGTH: 107
<212> TYPE: PRT
<213> ORGANISM: Artificial Sequence
<220> FEATURE:
<223> OTHER INFORMATION: Synthetic

<400> SEQUENCE: 73

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln Gln Lys Pro Gly Lys Gly Pro Arg Leu Leu Ile
        35                  40                  45

His Tyr Thr Ser Thr Leu Gln Pro Gly Phe Pro Ser Arg Phe Ser Gly
    50                  55                  60

Ser Gly Ser Gly Arg Asp Tyr Ser Leu Ser Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105
```

<210> SEQ ID NO 74
<211> LENGTH: 119
<212> TYPE: PRT
<213> ORGANISM: Artificial Sequence
<220> FEATURE:
<223> OTHER INFORMATION: Synthetic

<400> SEQUENCE: 74

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
```

```
                    20                  25                  30
Gly Met Gly Val Gly Trp Val Arg Gln Pro Ser Gly Lys Gly Leu Glu
            35                  40                  45

Trp Leu Ala His Ile Trp Trp Asn Asp Tyr Tyr Tyr Lys Thr Ala
 50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Val Asp Thr Ala Thr Tyr Tyr
                85                  90                  95

Cys Ala Arg Met Ala Pro Gly Thr Pro Phe Pro Ser Trp Gly Gln Gly
                100                 105                 110

Thr Leu Val Thr Val Ser Ala
            115

<210> SEQ ID NO 75
<211> LENGTH: 107
<212> TYPE: PRT
<213> ORGANISM: Artificial Sequence
<220> FEATURE:
<223> OTHER INFORMATION: Synthetic

<400> SEQUENCE: 75

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Ile Leu Leu Trp
                85                  90                  95

Thr Phe Gly Gly Gly Thr Lys Leu Glu Ile Lys
                100                 105

<210> SEQ ID NO 76
<211> LENGTH: 119
<212> TYPE: PRT
<213> ORGANISM: Artificial Sequence
<220> FEATURE:
<223> OTHER INFORMATION: Synthetic

<400> SEQUENCE: 76

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Asn Met Gly Val Gly Trp Ile Arg Gln Pro Ser Gly Lys Gly Leu Glu
            35                  40                  45

Trp Leu Ala His Ile Trp Trp Asn Asp Tyr Lys Tyr Tyr Asn Thr Ala
        50                  55                  60

Leu Lys Ser Arg Leu Thr Ile Ser Lys Asp Thr Ser Asn Asn Gln Val
65                  70                  75                  80

Phe Leu Lys Ile Ala Ser Leu Asp Thr Ala Asp Thr Ala Thr Tyr Tyr
                85                  90                  95
```

```
Cys Ala Arg Ile Gly Gly Gly Thr Pro Leu Asp Tyr Trp Gly Gln Gly
                100                 105                 110

Thr Ser Leu Thr Val Ser Ser
        115
```

<210> SEQ ID NO 77
<211> LENGTH: 107
<212> TYPE: PRT
<213> ORGANISM: Artificial Sequence
<220> FEATURE:
<223> OTHER INFORMATION: Synthetic

<400> SEQUENCE: 77

```
Asp Ile Gln Met Ala Gln Ser Pro Ser Ser Leu Ser Ala Ser Leu Gly
1               5                   10                  15

Gly Lys Val Thr Ile Thr Cys Lys Ala Ser Gln Asp Ile His Thr Tyr
            20                  25                  30

Ile Ala Trp Tyr Gln His Lys Pro Gly Lys Gly Pro Arg Leu Leu Met
        35                  40                  45

Leu Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asp Leu Leu Trp
                85                  90                  95

Thr Phe Gly Gly Gly Thr Lys Leu Glu Ile Lys
            100                 105
```

<210> SEQ ID NO 78
<211> LENGTH: 119
<212> TYPE: PRT
<213> ORGANISM: Artificial Sequence
<220> FEATURE:
<223> OTHER INFORMATION: Synthetic

<400> SEQUENCE: 78

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Val Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Phe
                85                  90                  95

Cys Ala Arg Ser Tyr Asp Gly Tyr Pro Phe Asp Tyr Trp Gly Gln Gly
                100                 105                 110

Thr Leu Val Thr Val Ser Ala
        115
```

<210> SEQ ID NO 79
<211> LENGTH: 107
<212> TYPE: PRT
<213> ORGANISM: Artificial Sequence
<220> FEATURE:
<223> OTHER INFORMATION: Synthetic

<400> SEQUENCE: 79

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln His Lys Pro Gly Lys Gly Pro Arg Leu Leu Ile
        35                  40                  45

His His Thr Ser Thr Leu Gln Pro Gly Ile Pro Ser Arg Phe Ser Glu
    50                  55                  60

Ser Gly Ser Gly Arg Asp Tyr Ser Phe Ser Ile Ser Asn Leu Glu Pro
65                  70                  75                  80

Glu Asp Ile Ala Ser Tyr Tyr Cys Leu Gln Tyr Asp Thr Leu Leu Trp
                85                  90                  95

Thr Phe Gly Gly Gly Thr Lys Leu Glu Ile Arg
            100                 105

<210> SEQ ID NO 80
<211> LENGTH: 119
<212> TYPE: PRT
<213> ORGANISM: Artificial Sequence
<220> FEATURE:
<223> OTHER INFORMATION: Synthetic

<400> SEQUENCE: 80

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala His Ile Trp Trp Asn Glu Asn Lys Tyr Tyr Asn Thr Asp
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Gly Pro Gly Val Pro Phe Asp Tyr Trp Gly Gln Gly
            100                 105                 110

Thr Thr Ile Thr Val Ser Ser
        115

<210> SEQ ID NO 81
<211> LENGTH: 107
<212> TYPE: PRT
<213> ORGANISM: Artificial Sequence
<220> FEATURE:
<223> OTHER INFORMATION: Synthetic

<400> SEQUENCE: 81

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Asn Gly
    50                  55                  60

```
Ser Gly Ser Gly Arg Asp Tyr Ser Phe Thr Ile Ser Asn Leu Glu Pro
 65                  70                  75                  80

Glu Asp Ile Ala Thr Tyr Tyr Cys Leu Gln Tyr Asp Ile Leu Thr Trp
                 85                  90                  95

Thr Phe Gly Gly Gly Thr Lys Leu Glu Ile Lys
                100                 105

<210> SEQ ID NO 82
<211> LENGTH: 119
<212> TYPE: PRT
<213> ORGANISM: Artificial Sequence
<220> FEATURE:
<223> OTHER INFORMATION: Synthetic

<400> SEQUENCE: 82

Gln Val Thr Leu Lys Glu Ser Gly Pro Gly Ile Leu Lys Pro Ser Gln
  1               5                  10                  15

Thr Leu Ser Leu Thr Cys Ser Phe Ser Gly Phe Ser Leu Ser Thr Ser
                 20                  25                  30

Gly Met Gly Val Gly Trp Ile Arg Gln Pro Ser Gly Lys Gly Leu Glu
             35                  40                  45

Trp Leu Ala His Ile Trp Trp Asn Asp Glu Lys Tyr Tyr Asn Pro Ser
 50                  55                  60

Leu Lys Ser Gln Leu Thr Ile Ser Lys Asp Thr Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Ser Tyr Asp Gly Ser Pro Phe Pro Ser Trp Gly Gln Gly
                100                 105                 110

Thr Leu Val Thr Val Ser Ala
            115

<210> SEQ ID NO 83
<211> LENGTH: 119
<212> TYPE: PRT
<213> ORGANISM: Artificial Sequence
<220> FEATURE:
<223> OTHER INFORMATION: Synthetic

<400> SEQUENCE: 83

Gln Val Ala Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
                 20                  25                  30

Gly Met Gly Val Gly Trp Ile Arg Gln Pro Ser Gly Lys Gly Leu Glu
             35                  40                  45

Trp Leu Ala His Ile Trp Trp His Gly Asn Lys Tyr Tyr Ser Thr Gly
 50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Ala Asp Thr Ala Thr Tyr Tyr
                 85                  90                  95

Cys Ala Arg Ile Ser Ala Gly Tyr Pro Leu Asp Tyr Trp Gly Gln Gly
                100                 105                 110

Thr Ser Val Thr Val Ser Ser
            115

<210> SEQ ID NO 84
```

<211> LENGTH: 119
<212> TYPE: PRT
<213> ORGANISM: Artificial Sequence
<220> FEATURE:
<223> OTHER INFORMATION: Synthetic

<400> SEQUENCE: 84

Gln Val Ala Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp His Gly Asn Lys Tyr Tyr Ser Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Ser Asp Gly Tyr Pro Leu Asp Tyr Trp Gly Gln Gly
            100                 105                 110

Thr Ser Val Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: Synthetic

<400> SEQUENCE: 85

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Val Arg Gln Pro Ser Gly Lys Gly Leu Glu
        35                  40                  45

Trp Leu Ala His Ile Trp Trp Asn Asp Tyr Tyr Tyr Lys Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Val Asp Thr Ala Thr Tyr Tyr
                85                  90                  95

Cys Ala Arg Met Ala Pro Gly Thr Pro Phe Pro Ser Trp Gly Gln Gly
            100                 105                 110

Thr Leu Val Thr Val Ser Ala
        115

<210> SEQ ID NO 86
<211> LENGTH: 119
<212> TYPE: PRT
<213> ORGANISM: Artificial Sequence
<220> FEATURE:
<223> OTHER INFORMATION: Synthetic

<400> SEQUENCE: 86

Gln Val Thr Leu Lys Glu Ser Gly Pro Gly Ile Leu Gln Pro Ser Gln
1               5                   10                  15

```
Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Ala His Ile Trp Trp Asn Asp Tyr Lys Tyr Tyr Asn Thr Ala
50                  55                  60

Leu Lys Ser Arg Leu Thr Ile Ser Lys Asp Thr Ser Asn Asn Gln Val
65                  70                  75                  80

Phe Leu Lys Ile Ala Ser Leu Asp Thr Ala Asp Thr Ala Thr Tyr Tyr
                85                  90                  95

Cys Ala Arg Ile Gly Gly Gly Thr Pro Leu Asp Tyr Trp Gly Gln Gly
                100                 105                 110

Thr Ser Leu Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: Synthetic

<400> SEQUENCE: 87

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Val Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Phe
                85                  90                  95

Cys Ala Arg Ser Tyr Asp Gly Tyr Pro Phe Asp Tyr Trp Gly Gln Gly
                100                 105                 110

Thr Leu Val Thr Val Ser Ala
        115

<210> SEQ ID NO 88
<211> LENGTH: 119
<212> TYPE: PRT
<213> ORGANISM: Artificial Sequence
<220> FEATURE:
<223> OTHER INFORMATION: Synthetic

<400> SEQUENCE: 88

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala His Ile Trp Trp Asn Glu Asn Lys Tyr Tyr Asn Thr Asp
50                  55                  60

Leu Lys Ser Arg Leu Thr Ile Ser Lys Asp Thr Ser Asn Asn Gln Val
65                  70                  75                  80
```

-continued

```
Phe Leu Lys Ile Ala Ser Val Asp Thr Ala Asp Thr Ala Thr Tyr Tyr
                85                  90                  95

Cys Ala Arg Ile Gly Pro Gly Val Pro Phe Asp Tyr Trp Gly Gln Gly
            100                 105                 110

Thr Thr Ile Thr Val Ser Ser
        115

<210> SEQ ID NO 89
<211> LENGTH: 107
<212> TYPE: PRT
<213> ORGANISM: Artificial Sequence
<220> FEATURE:
<223> OTHER INFORMATION: Synthetic

<400> SEQUENCE: 89

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Phe Gln His Lys Pro Gly Lys Gly Pro Arg Leu Leu Met
        35                  40                  45

Ala Tyr Pro Phe Thr Leu Gln Pro Gly Ile Pro Ser Arg Phe Ser Gly
    50                  55                  60

Asn Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Arg Leu Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln His Lys Pro Gly Lys Gly Pro Arg Leu Leu Ile
        35                  40                  45

His Tyr Thr Ser Thr Leu Gln Pro Gly Phe Pro Ser Arg Phe Ser Gly
    50                  55                  60

Ser Gly Ser Gly Arg Asp Tyr Ser Leu Ser Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Synthetic
```

<400> SEQUENCE: 91

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Val Trp Tyr Gln Gln Lys Pro Gly Lys Gly Pro Arg Leu Leu Ile
            35                  40                  45

His Tyr Thr Ser Thr Leu Gln Pro Gly Phe Pro Ser Arg Phe Ser Gly
        50                  55                  60

Ser Gly Ser Gly Arg Asp Tyr Ser Leu Ser Ile Thr Asn Leu Glu Pro
65                  70                  75                  80

Glu Asp Ile Ala Thr Tyr Tyr Cys Leu Gln Tyr Asp Asn Leu Leu Trp
                85                  90                  95

Thr Phe Gly Gly Gly Thr Lys Leu Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
            20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Ile Leu Leu Trp
                85                  90                  95

Thr Phe Gly Gly Gly Thr Lys Leu Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Synthetic

<400> SEQUENCE: 93

Asp Ile Gln Met Ala Gln Ser Pro Ser Ser Leu Ser Ala Ser Leu Gly
1               5                   10                  15

Gly Lys Val Thr Ile Thr Cys Lys Ala Ser Gln Asp Ile His Thr Tyr
            20                  25                  30

Ile Ala Trp Tyr Gln His Lys Pro Gly Lys Gly Pro Arg Leu Leu Met
            35                  40                  45

Leu Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

```
Glu Asp Ile Ala Thr Tyr Tyr Cys Leu Gln Tyr Asp Leu Leu Trp
                85              90              95

Thr Phe Gly Gly Gly Thr Lys Leu Glu Ile Lys
            100             105

<210> SEQ ID NO 94
<211> LENGTH: 107
<212> TYPE: PRT
<213> ORGANISM: Artificial Sequence
<220> FEATURE:
<223> OTHER INFORMATION: Synthetic

<400> SEQUENCE: 94

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Val Trp Tyr Gln His Lys Pro Gly Lys Gly Pro Arg Leu Leu Ile
            35                  40                  45

His His Thr Ser Thr Leu Gln Pro Gly Ile Pro Ser Arg Phe Ser Glu
        50                  55                  60

Ser Gly Ser Gly Arg Asp Tyr Ser Phe Ser Ile Ser Asn Leu Glu Pro
65                  70                  75                  80

Glu Asp Ile Ala Ser Tyr Tyr Cys Leu Gln Tyr Asp Thr Leu Leu Trp
                85              90              95

Thr Phe Gly Gly Gly Thr Lys Leu Glu Ile Arg
            100             105

<210> SEQ ID NO 95
<211> LENGTH: 107
<212> TYPE: PRT
<213> ORGANISM: Artificial Sequence
<220> FEATURE:
<223> OTHER INFORMATION: Synthetic

<400> SEQUENCE: 95

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Phe
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Asn Gly
        50                  55                  60

Ser Gly Ser Gly Arg Asp Tyr Ser Phe Thr Ile Ser Asn Leu Glu Pro
65                  70                  75                  80

Glu Asp Ile Ala Thr Tyr Tyr Cys Leu Gln Tyr Asp Ile Leu Thr Trp
                85              90              95

Thr Phe Gly Gly Gly Thr Lys Leu Glu Ile Lys
            100             105
```